(12) United States Patent
Giovangrandi

(10) Patent No.: US 10,945,671 B2
(45) Date of Patent: Mar. 16, 2021

(54) DETERMINING PHYSIOLOGICAL PARAMETERS USING MOVEMENT DETECTION

(71) Applicant: PhysioWave, Inc., Santa Clara, CA (US)

(72) Inventor: Laurent B. Giovangrandi, Palo Alto, CA (US)

(73) Assignee: Physiowave, Inc., Menlo Park, CA (US)

( * ) Notice: Subject to any disclaimer, the term of this patent is extended or adjusted under 35 U.S.C. 154(b) by 1352 days.

(21) Appl. No.: 14/747,986

(22) Filed: Jun. 23, 2015

(65) Prior Publication Data

US 2016/0374618 A1 Dec. 29, 2016

(51) Int. Cl.
 *A61B 5/00* (2006.01)
 *A61B 5/02* (2006.01)
 (Continued)

(52) U.S. Cl.
 CPC ............ *A61B 5/6887* (2013.01); *A61B 5/024* (2013.01); *A61B 5/02028* (2013.01);
 (Continued)

(58) Field of Classification Search
 CPC .................................................. A61B 5/6887
 See application file for complete search history.

(56) References Cited

U.S. PATENT DOCUMENTS

| | | |
|---|---|---|
| 3,702,113 A | 11/1972 | Blockley et al. |
| 4,195,643 A | 4/1980 | Pratt, Jr. |

(Continued)

FOREIGN PATENT DOCUMENTS

| | | |
|---|---|---|
| DE | 202009012748 | 12/2009 |
| EP | 0329306 A1 | 2/1989 |

(Continued)

OTHER PUBLICATIONS

Luna-Lozano, Pablo S., and Carlos Alvarado-Serrano. "Time and amplitude relationships of the ballistocardiogram in vertical and horizontal direction." 2012 9th International Conference on Electrical Engineering, Computing Science and Automatic Control (CCE). IEEE, 2012 (Year: 2012).*

(Continued)

*Primary Examiner* — Daniel L Cerioni
*Assistant Examiner* — Yasmeen S Warsi
(74) *Attorney, Agent, or Firm* — Crawford Maunu PLLC

(57) ABSTRACT

Certain aspects of the disclosure are directed to determining cardiac physiological parameters. Specific embodiments concern an arrangement of apparatuses including a platform region configured and arranged with an area for the user to stand, a plurality of force sensors including sensor circuitry, and a processor circuitry. The force sensors provide a plurality of analog signals while the user is standing on the platform region. The processor circuitry is configured and arranged to determine cardiac physiological parameters of the user corresponding to a graphical representation of cardiac movements, by processing the analog signals, mitigating at least some effect on the analog signals attributable to postural sway of the user, and generating data indicative of the physiological parameters based on said processing of the analog signals and the mitigating of at least some of the effect on the analog signals attributable to postural sway of the user.

17 Claims, 31 Drawing Sheets

(51) Int. Cl.
*A61B 5/024* (2006.01)
*A61B 5/11* (2006.01)
*A61B 5/0408* (2006.01)

(52) U.S. Cl.
CPC ........ *A61B 5/04085* (2013.01); *A61B 5/1102* (2013.01); *A61B 5/70* (2013.01); *A61B 5/7207* (2013.01); *A61B 5/7225* (2013.01); *A61B 5/742* (2013.01)

(56) References Cited

U.S. PATENT DOCUMENTS

| | | | |
|---|---|---|---|
| 4,362,164 A | 12/1982 | Little et al. | |
| 4,557,271 A | 12/1985 | Stoller et al. | |
| 4,657,025 A | 4/1987 | Orlando | |
| 4,679,569 A | 7/1987 | Lee | |
| 4,765,321 A | 8/1988 | Mohri | |
| 4,836,215 A | 6/1989 | Lee | |
| 4,947,857 A | 8/1990 | Albert et al. | |
| 4,958,638 A | 9/1990 | Sharpe et al. | |
| 5,314,389 A | 5/1994 | Dotan | |
| 5,431,170 A | 7/1995 | Mathews | |
| 5,620,003 A | 4/1997 | Sepponen | |
| 5,678,562 A | 10/1997 | Sellers | |
| 5,682,902 A | 11/1997 | Herleikson | |
| 5,701,894 A | 12/1997 | Cherry et al. | |
| 5,750,937 A | 5/1998 | Johnson et al. | |
| 5,782,238 A | 7/1998 | Beitler | |
| 5,833,623 A | 11/1998 | Mann et al. | |
| 6,047,203 A | 4/2000 | Sackner et al. | |
| 6,080,110 A | 6/2000 | Thorgersen | |
| 6,168,563 B1 | 1/2001 | Brown | |
| 6,198,394 B1 | 3/2001 | Jacobsen et al. | |
| 6,205,547 B1 | 3/2001 | Davis | |
| 6,228,033 B1 | 5/2001 | Koobi et al. | |
| 6,292,690 B1 | 9/2001 | Petrucelli | |
| 6,331,162 B1 | 12/2001 | Mitchell | |
| 6,454,708 B1 | 9/2002 | Ferguson et al. | |
| 6,454,719 B1 | 9/2002 | Greenhut | |
| 6,516,221 B1 | 2/2003 | Hirouchi et al. | |
| 6,551,252 B2 | 4/2003 | Sackner et al. | |
| 6,594,759 B1 | 7/2003 | Wang | |
| 6,640,134 B2 | 10/2003 | Raymond et al. | |
| 6,685,634 B1 | 2/2004 | Fry | |
| 6,702,754 B2 | 3/2004 | Ogura et al. | |
| 6,705,990 B1 | 3/2004 | Gallant | |
| 6,734,856 B2 | 5/2004 | Ishikawa et al. | |
| 6,755,783 B2 | 6/2004 | Cosentino et al. | |
| 6,783,498 B2 | 8/2004 | Sackner et al. | |
| 6,790,178 B1 | 9/2004 | Mault et al. | |
| 6,814,705 B2 | 11/2004 | Kawaguchi | |
| 6,847,892 B2 | 1/2005 | Zhou et al. | |
| 6,875,174 B2 | 4/2005 | Braun et al. | |
| 6,898,299 B1 | 5/2005 | Brooks | |
| 6,962,566 B2 | 11/2005 | Quistgaard et al. | |
| 6,963,035 B2 | 11/2005 | Honda et al. | |
| 7,137,955 B2 | 11/2006 | Bartels et al. | |
| 7,257,438 B2 | 8/2007 | Kinast | |
| 7,313,435 B2 | 12/2007 | Nakada et al. | |
| 7,316,648 B2 | 1/2008 | Kelly et al. | |
| 7,382,247 B2 | 6/2008 | Welch et al. | |
| 7,384,410 B2 | 6/2008 | Eggers et al. | |
| 7,417,536 B2 | 8/2008 | Lakshmanan et al. | |
| 7,459,644 B2 | 12/2008 | Kenmochi | |
| 7,502,643 B2 | 3/2009 | Farringdon et al. | |
| 7,668,588 B2 | 2/2010 | Kovacs | |
| 7,787,946 B2 | 8/2010 | Stahmann et al. | |
| 7,796,013 B2 | 9/2010 | Murakami et al. | |
| 7,846,104 B2 | 12/2010 | MacQuarrie et al. | |
| 7,899,522 B1 | 3/2011 | Koh et al. | |
| 8,200,320 B2 | 6/2012 | Kovacs | |
| 8,369,936 B2 | 2/2013 | Farringdon et al. | |
| 8,452,390 B2 | 5/2013 | Jensen | |
| 8,473,041 B2 | 6/2013 | Bartnik et al. | |
| 8,475,367 B1 | 7/2013 | Yuen et al. | |
| 8,529,409 B1 | 9/2013 | Lesea-Ames | |
| 8,548,556 B2 | 10/2013 | Jensen | |
| 8,639,226 B2 | 1/2014 | Hutchings et al. | |
| 8,682,424 B2 | 3/2014 | Tsoglin et al. | |
| 8,698,014 B1 | 4/2014 | Walstad | |
| 8,858,449 B2 | 10/2014 | Inan et al. | |
| 8,870,780 B2 | 10/2014 | Inan et al. | |
| 9,011,346 B2 | 4/2015 | Wiard et al. | |
| 9,055,871 B2 | 6/2015 | Inan et al. | |
| 9,215,991 B2 | 12/2015 | Inan et al. | |
| 9,241,637 B2 | 1/2016 | Wiard et al. | |
| 2001/0030546 A1 | 10/2001 | Yamada et al. | |
| 2001/0044588 A1 | 11/2001 | Mault | |
| 2002/0002326 A1 | 1/2002 | Causey, III et al. | |
| 2002/0062090 A1* | 5/2002 | Chai | A61B 5/05 600/547 |
| 2002/0188205 A1 | 12/2002 | Mills | |
| 2003/0050537 A1 | 3/2003 | Wessel | |
| 2003/0088196 A1 | 5/2003 | Steve | |
| 2003/0126593 A1 | 7/2003 | Mault | |
| 2003/0130567 A1 | 7/2003 | Mault et al. | |
| 2003/0130595 A1 | 7/2003 | Mault | |
| 2003/0149349 A1 | 8/2003 | Jensen | |
| 2003/0197614 A1 | 10/2003 | Smith et al. | |
| 2003/0233034 A1 | 12/2003 | Varri et al. | |
| 2004/0068379 A1 | 4/2004 | Morgan et al. | |
| 2004/0073127 A1 | 4/2004 | Istvan et al. | |
| 2004/0097802 A1 | 5/2004 | Cohen | |
| 2004/0138517 A1 | 7/2004 | Osorio et al. | |
| 2004/0211599 A1 | 10/2004 | Kasinoff | |
| 2004/0249258 A1 | 12/2004 | Tupin, Jr. et al. | |
| 2005/0004483 A1 | 1/2005 | Lin | |
| 2005/0017602 A1 | 1/2005 | Arms et al. | |
| 2005/0033124 A1 | 2/2005 | Kelly et al. | |
| 2005/0043645 A1 | 2/2005 | Ono et al. | |
| 2005/0113703 A1 | 5/2005 | Farringdon et al. | |
| 2005/0119711 A1 | 6/2005 | Cho et al. | |
| 2005/0171451 A1 | 8/2005 | Yeo et al. | |
| 2005/0203349 A1 | 9/2005 | Nanikashvili | |
| 2005/0206518 A1 | 9/2005 | Welch et al. | |
| 2005/0247494 A1 | 11/2005 | Montagnino | |
| 2005/0283198 A1 | 12/2005 | Haubrich et al. | |
| 2006/0049955 A1 | 3/2006 | Blum et al. | |
| 2006/0079942 A1 | 4/2006 | Deno et al. | |
| 2006/0106646 A1 | 5/2006 | Squilla et al. | |
| 2006/0111641 A1 | 5/2006 | Manera et al. | |
| 2006/0116589 A1 | 6/2006 | Park | |
| 2006/0122525 A1 | 6/2006 | Shusterman | |
| 2006/0149139 A1 | 7/2006 | Bonmassar et al. | |
| 2006/0154642 A1 | 7/2006 | Scannell | |
| 2006/0155589 A1 | 7/2006 | Lane et al. | |
| 2007/0055324 A1 | 3/2007 | Thompson et al. | |
| 2007/0069887 A1 | 3/2007 | Welch et al. | |
| 2007/0161913 A1 | 7/2007 | Farrell et al. | |
| 2007/0197878 A1 | 8/2007 | Shklarski | |
| 2007/0208232 A1 | 9/2007 | Kovacs | |
| 2007/0293770 A1 | 12/2007 | Bour et al. | |
| 2008/0027679 A1 | 1/2008 | Shklarski | |
| 2008/0073128 A1 | 3/2008 | Umemoto | |
| 2008/0154645 A1 | 6/2008 | Takehara | |
| 2008/0161700 A1 | 7/2008 | Sachanandani et al. | |
| 2008/0183090 A1 | 7/2008 | Farringdon et al. | |
| 2008/0194975 A1 | 8/2008 | MacQuarrie et al. | |
| 2008/0208009 A1 | 8/2008 | Shklarski | |
| 2008/0221404 A1 | 9/2008 | Tso | |
| 2008/0246629 A1 | 10/2008 | Tsui et al. | |
| 2008/0281222 A1 | 11/2008 | Fukada | |
| 2008/0306393 A1 | 12/2008 | Ting et al. | |
| 2009/0024044 A1 | 1/2009 | Virtanen et al. | |
| 2009/0102296 A1 | 4/2009 | Greene et al. | |
| 2009/0182204 A1 | 7/2009 | Semler et al. | |
| 2009/0203972 A1 | 8/2009 | Heneghan et al. | |
| 2009/0284496 A1 | 11/2009 | Oki | |
| 2009/0315733 A1 | 12/2009 | Bischoff | |
| 2010/0004715 A1 | 1/2010 | Fahey | |
| 2010/0016685 A1 | 1/2010 | Muehlsteff et al. | |
| 2010/0094147 A1 | 4/2010 | Inan et al. | |
| 2010/0210921 A1 | 8/2010 | Park et al. | |
| 2010/0262044 A1 | 10/2010 | Siegler | |

(56) References Cited

U.S. PATENT DOCUMENTS

| | | | |
|---|---|---|---|
| 2011/0040352 | A1 | 2/2011 | Gerber et al. |
| 2011/0054359 | A1 | 3/2011 | Sazonov et al. |
| 2011/0240379 | A1 | 10/2011 | Forshaw et al. |
| 2011/0245710 | A1 | 10/2011 | Jensen |
| 2011/0310005 | A1 | 12/2011 | Chen |
| 2012/0003933 | A1 | 1/2012 | Baker et al. |
| 2012/0065895 | A1 | 3/2012 | Saul |
| 2012/0071792 | A1* | 3/2012 | Pfeffer ............... A61B 5/11 600/587 |
| 2012/0123219 | A1 | 5/2012 | Georgiev et al. |
| 2012/0165622 | A1 | 6/2012 | Rodriguez et al. |
| 2012/0245476 | A1* | 9/2012 | Skerl ............... A61B 5/1102 600/485 |
| 2012/0283587 | A1 | 11/2012 | Gosh et al. |
| 2012/0302843 | A1 | 11/2012 | Otsubo et al. |
| 2012/0318869 | A1 | 12/2012 | Edmonds |
| 2013/0056285 | A1 | 3/2013 | Meagher |
| 2013/0113506 | A1 | 5/2013 | Poupyrev et al. |
| 2013/0289889 | A1 | 10/2013 | Yuen et al. |
| 2013/0310700 | A1 | 11/2013 | Wiard et al. |
| 2014/0089836 | A1 | 3/2014 | Damani et al. |
| 2014/0094707 | A1 | 4/2014 | Farringdon et al. |
| 2014/0121540 | A1 | 5/2014 | Raskin |
| 2014/0142396 | A1 | 5/2014 | Ricks et al. |
| 2014/0142437 | A1* | 5/2014 | Inan ............... A61B 5/1102 600/479 |
| 2014/0172314 | A1 | 6/2014 | Baarman |
| 2014/0221849 | A1 | 8/2014 | Farringdon et al. |
| 2014/0221850 | A1 | 8/2014 | Farringdon et al. |
| 2015/0107910 | A1 | 4/2015 | Villard et al. |
| 2015/0112209 | A1* | 4/2015 | Blaber ............... A61B 5/7246 600/483 |
| 2015/0160068 | A1 | 6/2015 | Carreel et al. |
| 2015/0168205 | A1 | 6/2015 | Lee |
| 2015/0201844 | A1 | 7/2015 | Nakagawa |
| 2015/0289802 | A1 | 10/2015 | Thomas et al. |
| 2015/0331491 | A1 | 11/2015 | Rumreich |
| 2015/0335291 | A1 | 11/2015 | Saadi et al. |
| 2015/0338265 | A1 | 11/2015 | Carreel et al. |
| 2016/0029905 | A1 | 2/2016 | Kovacs |
| 2016/0116326 | A1 | 4/2016 | Sharma |
| 2016/0317043 | A1 | 11/2016 | Campo et al. |

FOREIGN PATENT DOCUMENTS

| | | |
|---|---|---|
| ES | 2296474 A1 | 4/2008 |
| ES | 2328205 B1 | 8/2010 |
| ES | 2385898 A1 | 8/2012 |
| ES | 2398439 A2 | 3/2013 |
| ES | 2398542 A2 | 3/2013 |
| GB | 2225459 | 5/1990 |
| GB | 2367896 A | 4/2002 |
| JP | 2001198096 | 7/2001 |
| JP | 2001309893 | 11/2001 |
| JP | 2002119488 | 4/2002 |
| JP | 2006212155 | 8/2006 |
| JP | 2007283071 A | 11/2007 |
| JP | 2009050508 A | 3/2009 |
| KR | 0137272 B1 | 4/1998 |
| KR | 20050079235 A | 8/2005 |
| WO | 2005074379 A2 | 8/2005 |
| WO | 2006088280 A1 | 8/2006 |
| WO | 2007103835 A2 | 9/2007 |
| WO | 2008102298 A1 | 8/2008 |
| WO | 2010004502 A1 | 1/2010 |
| WO | WO2010004502 | 1/2010 |
| WO | 2010045455 A1 | 4/2010 |
| WO | 2011075767 A1 | 6/2011 |
| WO | WO2012103296 | 8/2012 |
| WO | 2013017717 A2 | 2/2013 |
| WO | 2013066642 A1 | 5/2013 |

OTHER PUBLICATIONS

J. Alametsä et al. "Ballistocardiogaphic studies with acceleration and electromechanical film sensors." Medical Engineering & Physics 31 (2009), p. 1154-1165.

J. Alametsä et al. "Arterial Elasticity Measurements with Ankle Pulse Width Velocity and Ballistocardiography." ECIFMBE 2008, IFMBE Proceedings 22, p. 1636-1641.

J. Allen. "Photoplethysmography and its application in clinical physiological measurement." Physiol. Meas. 28, 2007, p. R1-R39.

A. Avolio et al. "Role of Pulse Pressure Amplification I Arterial Hpertension: Experts' Opinion and Review of the Data." Hypertension, vol. 54, Aug. 1, 2009, p. 375-383.

J. Blacher et al. "Aortic Pulse Wave Velocity as a Marker of Cardiovascular Risk in Hypertensive Patients," Hypertension, vol. 33, 1999, p. 1111-1117.

Davis, S; B. van den Bogaard et al. "Active standing reduces wave reflection in the presence of increased peripheral resistance in young and old healthy individuals." J Hypertension (4) Apr. 29, 2011, p. 682-689 (Abstract); and B. van den Bogaard. "Chapter 12: Active standing reduces wave reflection in the presence of increased peripheral resistance in young and old healthy individuals." Dissertation, Univ. Amsterdam, 2012, p. 180-193.

G. Kim et al. "Vascular Variation of PTT and the Vascular Characteristic Index According to the Posture Change." In Proceedings of the 2007 International Conference on Convergence Information Technology (ICCIT '07). IEEE Computer Society, Nov. 2007, p. 2426-2425. Abstract Only.

E. Pinheiro et al. "Non-Intrusive Device for Real-Time Circulatory System Assessment with Advanced Signal Processing Capabilities." Measurement Science Review, vol. 10, No. 5, 2010, p. 167-175.

E. Pinheiro et al. "Pulse arrival time and ballistocardiogram application to blood pressure variability estimation." Medical Measurements and Applications, 2009. IEEE Workshop, May 29-30, 2009. Abstract only.

M Safar."Arterial aging—hemodynamic changes and therapeutic options." Nat Rev Cardiol, vol. 7, 207, p. 442-449. Abstract / Introduction Only.

R. Wiard et al. "Estimation of Central Aortic Forces in the Ballistocardiogram under Rest and Exercise Conditions." 31st Annual International Conference of the IEEE EMBS, Sep. 2-6, 2009, p. 2831-2834.

R. Wiard et al. "Automatic detection of motion artifacts in the ballistocardiogram measured on a modified bathroom scale." Med Biol Eng Comput (2011) 49:213-220. Published online Dec. 9, 2010.

B. Williams et al. "Differential Impact of Blood Pressure-Lowering Drugs on Central Aortic Pressure and Clinical Outcomes: Principal Results of the Conduit Artery Function Evaluation (CAFE) Study," Circulation, vol. 113, Feb. 13, 2006, p. 1213-1225.

O.T. Inan M. Etemadi, R.M. Wiard, L. Giovangrandi, and G. T. A. Kovacs, "Robust Ballistocardiogram Acquisition for Home Monitoring," Phys. Meas., vol. 30, No. 2, pp. 169-185 (2009).

Inan OT, Etemadi M, Paloma A, Giovangrandi L, Kovacs GTA (2009) Non-invasive cardiac output trending during exercise recovery on a bathroom-scale-based ballistocardiograph. Physiol Meas 30:261-274 Abstract / Introduction Only.

Inan OT, Etemadi M, Wiard RM, Kovacs GTA, Giovangrandi L (2009) Novel methods for estimating the ballistocardiogram signal using a simultaneously acquired electrocardiogram. In: 31st annual IEEE engineers in medicine and biology conference. IEEE, Minneapolis, MN Abstract / Introduction Only.

Inan OT, Kovacs GTA, Giovangrandi L (2010) Evaluating the lower-body electromyogram signal acquired from the feet as a noise reference for standing ballistocardiogram measurements. IEEE Trans Inf Technol Biomed 14:1188-1196 Abstract / Introduction Only.

DeLoach SS, Twonsend RR, "Vascular Stiffness: Its Measurement and Significance for Epidemiologic and Outcome Studies", Clin J Am Soc Nephrol, 3: 184-192, 2008. Abstract / Introduction Only.

Webster's Ninth New Collegiate Dictionary, Meriam-Webster Inc., 1990, p. 1152.

(56) References Cited

OTHER PUBLICATIONS

Alan Fang et al., "Using a Geophone for Vibration Cancellation in a STM," abstract, Bulletin of the American Physical Society, 2008 APS March Meeting, vol. 53, No. 2, Mar. 10, 2008.

De Vries, S. O. et al., "Prediction of the Left Ventricular Mass from the Electrogram in Systemic Hypertension," American Journal of Cardiology, May 1, 1996;777(11):974-8. (Abstract Only).

A.Akhbardeh, M. Koivuluoma, T. Koivistoinen and A. Varri, "Ballistocardiogram Diagnosis Using Neural Networks and Shift-Invariant Daubechies Wavelet Transform," Researchers at Institute of Signal Processing, Tampere University of Technololgy, Tampere 33101, Finland.

O. Inan, et al., "Evaluating the Foot Electromyogram Signal as a Noise Reference for a Bathroom Scale Ballistocardiogram Recorder," Stanford University, Department of EE, Department of Bioengineering.

0. Inan and G. Kovacs, "An 11 µW, Two-Electrode Transimpedance Biosignal Amplifier with Active Current Feedback Stabilization," IEEE Transactions on Biomedical Circuits and Systems (2009).

0. Inan, M. Etemadi, B. Widrow and G. Kovacs, "Adaptive cancellation of floor vibrations in standing ballistocardiogram measurements using a seismic sensor as a noise reference," IEEE (2009).

R. F. Yazicioglu, P. Merken, R. Puers and C. Van Hoof, "A 60 µW 60 nV/..JHz Readout Front-End for Portable Biopotential Acquisition Systems," IEEE Journ. of Solid-State Circuits, vol. 42, No. 5 (May 2007).

W. Rosamond et al., "Heart Disease and Stroke Statistics—2007 Update: A Report from the American Heart Association Statistics Committee and Stroke Statistics Subcommittee," Circ., v. 115, pp. 69-171 (2007).

R. R. Harrison, "A Versatile Integrated Circuit for the Acquisition of Biopotentials," IEEE CICC, pp. 115-122 (2007).

T. Denison, K. Consoer, W. Santa, A.-T. Avestruz, J. Cooley, and A. Kelly, "A 2µW JOO nV/rtHz, Chopper-Stabilized Instrumentation Amplifier for Chronic Measurement of Neural Field Potentials," IEEE Jour. Solid-State Circuits, v. 42, No. 12, DD. 2934-2945 (2007).

A.Akhbardeh, S. Junnila, M. Koivuluoma, T. Koivistoinen, V. Turjanmaa, T. Koobi, and A. Viirri, "Towards a heart disease diagnosing system based on force sensitive chair's measurement, biorthogonal wavelets and neural networks," ScienceDirect, Engineering Applications for Artificial Intelligence, pp. 1-10 (2006).

D. Corrado, C. Basso, A. Pavel, P. Michieli, M. Schiavon, and G. Thiene, "Trends in Sudden Cardiovascular Death in Young Competitive Athletes After Implementation of a Preparticipation Screening Program," JAMA, vol. 296, No. 13, pp. 1593-1601 (Oct. 4, 2006).

C.N. Chien and F.S. Jaw, "Miniature ultra-low-power biopotential amplifier for potable [sic} applications," Biomedical Engineering-Applications, Basis & Communications, vol. 17, No. 2, pp. 11-49 (Apr. 2005).

C.W. Mundt, K.N. Montgomery, U.E. Udoh, V.N. Barker, G.C. Thonier, A.M. Tellier, R.D. Ricks, R.B. Darling, Y.D. Cagle, N.A. Cabrol, S.J. Ruoss, J.L. Swain, J.W. Hines, and G.T.A. Kovacs, "A Multiparameter Wearable Physiologic Monitoring System for Space and Terrestrial Applications," IEEE Trans. Inform. Tech. in Biomed., vol. 9, No. 3, pp. 382-391 (Sep. 2005).

M. Shojaei-Baghini, R.K. Lal, and D.K. Sharma, "A Low-Power and Compact Analog CMOS Processing Chip for Portable ECG Recorders," Proc. IEEE A.S.S.C.C., DD. 473-476 (2005).

J. Alametsii, A. Viirri, M. Koivuluoma, and L. Barna, "The Potential of EMFi Sensors in Heart Activity Monitoring," 2nd OpenECG Workshop "Integration of the ECG into the EHR & Interoperability of ECG Device Systems," Apr. 1-3, 2004 Berlin, Germany.

E. Company-Bosch and E. Hartmann, "ECG Front-End Design is Simplified with MicroConverter," Analog Dialogue, 37-11, pp. 1-5 (Nov. 2003).

D.M. Linton and u. Giion, "Advances in noninvasive cardiac output monitoring," Annals of cardiac Anaesthesia, vol. 5, pp. 141-148 (2002).

M. Watanabe, J. Marine, R. Sheldon, and 1\1. Josephson, "Effects of Ventricular Premature Stimulus Coupling Interval on Blood Pressure and Heart Rate Turbulence," Circ., vol. 106, pp. 325-330 (2002).

K. Lu, J. W. Clark, Jr. F. H. Ghorbel, D. L. Ware, and A. Bidani, "A human cardiopulmonary system model applied to the analysis of the Valsalva maneuver," Am. J Physiol. Heart Circ. Physiol., vol. 281, pp. H2661-H2679 (2001).

J. Rapoport, D. Teres, J. Steingrub, T. Higgins, W. McGee, and S. Lemeshow, "Patient characteristics and ICU organizational factors that influence frequency of pulmonary artery catheterization," JAMA, vol. 283, No. 19, pp. 2559-2567 (2000).

B.D. Johnson, K.C. Beck, D.N. Proctor, J. Miller, N.M. Dietz, and M.J. Joyner, "Cardiac output during exercise by the open circuit acetylene washin method: comparison with direct Fick," J. Appl Physiol, vol. 88, pp. 1650-1658 (2000).

W. Klimesch, "EEG alpha and theta oscillations reflect cognitive and memory performance: a review and analysis," Brain Research Reviews, vol. 29, DD. 169-195 (1999).

D. Corrado, C. Basso, M. Schiavon, and G. Thiene, "Screening for Hypertrophic Cardiomyopathy in Young Athletes," NEJM, vol. 339, pp. 364-369 (Aug. 6, 1998).

A.C. MettingVanRijn, A. Peper and C.A. Grimbergen, "Amplifiers for bioelectric events: a design with a minimal number of parts," Med. & Biol. Eng. & Comput., vol. 32, DD. 305-310 (1994).

R. Moore, R. Sansores, V. Guimond, and R. Abboud, "Evaluation of cardiac output by thoracic electrical bioimpedance during exercise in normal subjects," American College of Chest Physicans, vol. 102, DD. 448-455 (1992).

J. Christie, L.M. Sheldahl, F.E. Tristani, K.B. Sagar, M.J. Ptacin, and S. Wann, "Determination of stroke volume and cardiac output during exercise: comparison of two-dimensional and Doppler echocardiography, Fick oximetry, and thermodilution," Circ., vol. 76, DD. 539-547 (1987).

H. Benjelloun, R. Itti, L. Philippe, J.M. Lorgeron and M. Brochier, "Beat-to-Beat Assessment of Left Ventricular Ejection in Atrial Fibrillation," European Journal Nuclear Medicine, vol. 8, pp. 206-210 (1983).

S. Grimnes, "Impedance measurement of individual skin surface electrodes," Med. & Biol. Eng. & Comput., vol. 21, DD. 750-755 (1983).

Y. Miyamoto, M. Takahashi, T. Tamura, T. Nakamura, T. Hiura, and M. Mikami, "Continuous determination of cardiac output during exercise by the use of impedance plethysmogrphy," Med. Biol. Eng. Comp., vol. 19, DD. 638-644, (1981).

R.P. Lewis, S.E. Rittogers, W.F. Froester, and H. Boudoulas, "A critical review of the systolic time intervals," Circulation, vol. 56, DD. 146-158 (1977).

Laurent S et al., "Expert consensus document on arterial stiffness: methodological issues and clinical applications", European Heart Journal (2006) 27, 2588-2605.

Boutouyrie P et al., "Assessment of arterial stiffness for clinical and epidemiological studies: methodological considerations for validation and entry into the European Renal and Cardiovascular Medicine registry", Nephrol Dial Transplant (2014) 29: 232-239.

Stewart A D. et al., "Acute Reduction of Blood Pressure by Nitroglycerin Does Not Normalize Large Artery Stiffness in Essential Hypertension", Hypertension 2006, 48: 404-410.

Stewart A D. et al., "Effects of Inhibition of Basal Nitric Oxide Synthesis on Carotid-Femoral Pulse Wave Velocity and Augmentation Index in Humans", Hypertension 2003, 42: 915-918.

Avolio A P., et al., "Effects of aging on changing arterial compliance and left ventricular load in a northern Chinese urban community", Circulation 68, No. 1, 50-58, 1983.

Wilkinson, I B. et al., "Artery Society guidelines for validation of non-invasive haemodynamic measurement devices: Part 1, arterial pulse wave velocity" Artery Research (2010) 4, 34-40.

Avolio A P., et al. "Improved Arterial Distensibility in Normotensive Subjuects on a Low Salt Diet", Arteriosclerosis 6: 166-169, 1986.

(56) References Cited

OTHER PUBLICATIONS

Balkestein E J., et al., "The effect of weight loss with or without exercise training on large artery compliance in healthy obese men", J. Hypertens 1999, 17: 1831-1835.

Laurent S, et al., "Mesure de la Rigidite Arterielle" Dec. 2013.

Wiard, Richard M., et al. "Preliminary results from standing ballistocardiography measurements in microgravity." 2013 35th Annual International Conference of the IEEE Engineering in Medicine and Biology Society (EMBC). IEEE, 2013. Abstract only.

Inan, Omer T., et al. "Noninvasive measurement of physiological signals on a modified home bathroom scale." IEEE Transactions on Biomedical Engineering 59.8 (2012): 2137-2143. Abstract only.

Giovangrandi, Laurent, et al. "Preliminary results from BCG and ECG measurements in the heart failure clinic." 2012 Annual International Conference of the IEEE Engineering in Medicine and Biology Society. IEEE, 2012. Abstract only.

Park, Dookun, Omer T. Inan, and Laurent Giovangrandi. "A combined heartbeat detector based on individual BCG and IPG heartbeat detectors." 2012 Annual International Conference of the IEEE Engineering in Medicine and Biology Society. IEEE, 2012. Abstract only.

Etemadi, Mozziyar, et al. "Rapid assessment of cardiac contractility on a home bathroom scale." IEEE transactions on information technology in biomedicine 15.6 (2011): 864-869. Abstract only.

Giovangrandi, L., et al. "Ballistocardiography—a method worth revisiting." Conference proceedings: . . . Annual International Conference of the IEEE Engineering in Medicine and Biology Society. IEEE Engineering in Medicine and Biology Society. Annual Conference. vol. 2011. NIH Public Access, 2010.

Inan, Omer T., et al. "Multi-signal electromechanical cardiovascular monitoring on a modified home bathroom scale." 2011 Annual International Conference of the IEEE Engineering in Medicine and Biology Society. IEEE, 2011. Abstract only.

Wiard, R. M., et al. "Estimation of central aortic forces in the ballistocardiogram under rest and exercise conditions." Conference proceedings: . . . Annual International Conference of the IEEE Engineering in Medicine and Biology Society. IEEE Engineering in Medicine and Biology Society. Annual Conference. vol. 2009. NIH Public Access, 2008.

Etemadi, Mozziyar, et al. "Non-invasive assessment of cardiac contractility on a weighing scale." 2009 Annual International Conference of the IEEE Engineering in Medicine and Biology Society. IEEE, 2009. Abstract only.

Inan, Omer T., et al. "Non-invasive measurement of valsalva-induced hemodynamic changes on a bathroom scale ballistocardiograph." 2008 30th Annual International Conference of the IEEE Engineering in Medicine and Biology Society. IEEE, 2008. Abstract only.

Inan, Omer T., et al. "Unobtrusive Monitoring of Cardiovascular Health at Home Using a Modified Weighing Scale." 6th European Conference of the International Federation for Medical and Biological Engineering. Springer International Publishing, 2015. Abstract only.

McCall, Corey, et al. "Standing ballistocardiography measurements in microgravity." 2014 36th Annual International Conference of the IEEE Engineering in Medicine and Biology Society. IEEE, 2014. Abstract only.

Inan, Omer Tolga. Novel technologies for cardiovascular monitoring using ballistocardiography and electrocardiography. vol. 70. No. 10. 2009. Copy unavailable.

Wiard, Richard Matthew. Validation of Non-invasive Standing Arterial Stiffness Measurements Using Ballistocardriography and Photoplethysmography. 2012. Abstract only.

I. Starr and F.C. Wood, "Twenty-Year Studies with the Ballistocardiograph: The Relation Between the Amplitude of the First Record of 'Healthy' Adults and Eventual Mortality and Morbidity from Heart Disease," Circulation, vol. 36, DD. 714-732 (1961).

D.C. Deuchar, S.A. Talbot, and W.R. Scarborough, "Some Observations on the Relation of the High-Frequency Bed Ballistocardiogram to that Obtained from an Aperiodic Bed," Circulation, vol. 11, pp. 228-239 (1955).

H. Mandelbaum and R.A. Mandelbaum, "Studies Utilizing the Portable Electromagnetic Ballistocardiograph: IV. The Clinical Significance of Serial Ballistocardiograms Following Acute Myocardial Infarction," Circulation, vol. 7, pp. 910-9165 (1953).

R.S. Guber, M. Rodstein and H.E. Ungerleider, "Ballistocardiograph: An Appraisal of Technic, Physiological Principles, and Clinic Value," Circulation, vol. 7, DD. 268-286 (1953).

M.B. Rappaport, H.B. Sprague, and W.B. Thompson, "Ballistocardiography: I. Physical Considerations," Circulation, vol. 7, pp. 229-246 (1953).

0. Tannenbaum, J. Schack and H. Vesell, "Relationship between Ballistocardiographic Forces and Certain Events in the Cardiac Cycle," Circulation, vol. 6, DD. 586-592 (1952).

T.E. Satterthwaite, "Cardiovascular Diseases: Recent Advances in Their Anatomy, Physiology, Pathology, Diagnosis and Treatment," Lemcke and Beuschner, New York, NY (1913).

J.W. Gordon, "On Certain Molar Movements of the Human Body Produced by the Circulation of the Blood," J. of Anat. and Phys., vol. 11, DD. 533-536 (1877).

Gonzalez, et al. "Deteccion of las frecuencias 1-9 cardiaca and respitatoria mediante una bascu the electronica" In: IFMBE Proceedings. vol. 18, pp. 448-451, 2008. Springer-Verlag Berlin Heidelberg. Abstract Only.

Gomez-Clapers J. et al. "Pulse arrival time estimation from the impedance plethysmogram obtained with a handheld device", 33rd Annual International Conference of the IEEE EMBS, Boston, USA, Mar. 8-9, 2011, pp. 516-519. Abstract only.

HeartForce Medical Inc. "Definitions and Terminologies: History of Seismocardiology." www.heartforcemedical.com 4 pages.

Shin et al., "Non-constrained monitoring of systolic blood pressure on a seighing scale", Physiological Measurement, vol. 30, No. 7, pp. 679-693, 2009 Abstract Only.

Pliquett et al., "Front end with offset-free symmetrical current source optimized for time domain impedance spectroscopy", Physiological Measurement, vol. 32, No. 7, 2011.I Abstract Only.

Earbud Ballistocardiogram: HeadSense Israel: http://head-sensemed.com/ http://www.medgadget.com/2013/07/headsense-intracranial-pressure-monitoring-earbuds.html.

Bifrostec & The Kaiteki Institute http://www.psfk.com/2013/11/earbud-heart-monitor.html#IzIKRT.

http://www.endgadget.com/2014/01/06/intel-smart-earbuds/.

Mitchell et al., "Arterial Stiffness and Cardiovascular Events the Framingham Heart Study". Circulation 2010, 121: 505-11.

Blacher et al., "Impact of Aortic Stiffness on Survival in End-Stage Renal Disease" Circulation, 1999: 99.

Blacher et al., "Arterial Calcifications, Arterial Stiffness, and Cardiovascular Risk in End Stage Renal Disease" Hypertension. 38: 938-942 (2001).

Di Micco, et al., "Daily dialysis reduces pulse wave velocity in chronic hemodialysis patients". Hypertension Research. vol. 35, 2012.

Kříž, Jan, and Petr Šeba. "Force plate monitoring of human hemodynamics." Nonlinear biomedical physics 2.1 (2008): 1.

Migeotte, P-F., et al. "Three dimensional ballistocardiography: methodology and results from microgravity and dry immersion." Engineering in Medicine and Biology Society, EMBC, 2011 Annual International Conference of the IEEE. IEEE, 2011.

Prisk, G. K., et al. "Three-dimensional ballistocardiography and respiratory motion in sustained microgravity." Aviation, space, and environmental medicine 72.12 (2001): 1067-1074.

Schwerdt, H., et al. "Design and evaluation of a new computer-based force vectorballistocardiograph." Medical and Biological Engineering and Computing 25.4 (1987): 453-458.

Soames, R. W., and J. Atha. "Three-dimensional ballistocardiographic responses to changes of posture." Clinical Physics and Physiological Measurement 3.3 (1982): 169.

Soames, Roger W. The genesis of postural sway with special reference to cardiovascular dynamics. Diss. © Roger William Soames, 1978.

(56) References Cited

OTHER PUBLICATIONS

European Patent Office, Third Examination Report dated Nov. 26, 2014 for EPO Patent Application No. 07757854.0. which claims priority from PCT Application No. PCT/US2007/063244.
China State Intellectual Property Office, Office Action dated Oct. 13, 2010 for CN Patent Application No. 200780015788.1.
Japan Patent Office, Notice of Reasons for Rejection dated Mar. 6, 2012 for JPO Patent Application No. P2008-558484. which claims priority from PCT Application No. PCT/US2007/063244; Reference 1 cited in the Notice of Reaons for Rejection corresponds to U.S. Appl No. 08/555,546, now U.S. Pat. No. 5,701,894, Cherry et al., which is cited above; Reference 2, US 20030050537, Wessel, is cited above.
European Patent Office, Extended European Search Report dated Feb. 12, 2010 for EPO Application No. 07757854.0.
International Search Report and Written Opinion of the International Searching Authority for PCT International App. No. PCT/US07/63244.
Discera, "Shrinking Wireless Architectures", available for download from www.discera.com prior to Mar. 3, 2006.
GeTeMed GmbH, "Baby Monitoring System Vitaguard VG3000", Teltow, Germany, 1997-1999.
Atmel, "Microcontroller with 16 K Bytes In-System Programmable Flash", Atmel Atmega, document contains notation AVR 06/05.
Kaminska, "Wireless Wearable Biomonitors for Lifetime Wellness Optimization", Proceedings of the 3rd Annual International IEEE EMBS Special Topic Conference on Microtechnologies in Medicine and Biology, Kahuku, Oahu, Hawaii, May 2005. Abstract Only.
NorthEast Monitoring Inc., "Holter LX Pro Software—Operator's Manual", NorthEast Monitoring Inc. Two Clock Tower Suite 360 Maynard Massachusetts 01754, Apr. 2003.
Nguyen et al., "Transceiver Front-End Architectures Using Vibrating Micromechanical Signal Processors", Dig. of Papers, Topical Meeting on Silicon Monolithic Integrated Circuits in RF Systems: 23-32, Sep. 4, 2001.
ANSI/AAMI, EC11:1991/(R) 2001, Diagnostic Electrogardiographic Devices, 2000.
ANSI/MM I, EC38: 1998, Ambulatory Electrocardiographs, 1999.
Nguyen et al., "Frequency-Selective MEMS for Miniaturized Low-Power Communication Devices", IEEE Trans. Microwave Theory Tech 47(8):1486-1503, Aug. 1999.
Nguyen et al., "An Integrated CMOS Micromechanical Resonator High-Q Oscillator", IEEE Journal of Solid-State Circuits 34(4), Apr. 1999.
Nguyen et al., "Micromachined Devices for Wireless Communications," Proc. IEEE 86(8):1756-1768, Aug. 1998.
Kovacs, "Micromachined Transducers-Sourcebook", McGraw-Hill, New York, New York, 1998 944 page book Book Description provided.
Desel et al., "A CMOS Nine Channel ECG Measurement IC", ASIC 1996 2nd International Conference: 115-118, Oct. 1996 Abstract Only.
Fraunhofer, "Medical Technolology", http://www.iis.fraunhofer.de/en/ff/med.html Dec. 26, 2005.
Toumaz "Technology", Nov. 8, 2005 (copy available in U.S. Appl. No. 11/367,155).
Kaminiski, "Wearable Biomonitors With Wireless Network Communication" draft of paper published in Proceedings of the 3rd Annual International IEEE EMBS Special Topic Conference on Microtechnologies in Medicine and Biology, Kahuku, Oahu, Hawaii, May 2005.
Novosense AB, "Company", Apr. 4, 2005.
IMEC, "Sensor Electronics", Mar. 31, 2005.
Novosense, AB, "Technology", available for download at http://www.novosense.se/technology.html Aug. 5, 2015.
Miromico AG, "Sample Projects", available for dowolcad at http://www.miromico.ch/index.php?sec-ad.sa&lang=2, page includes notice of Copyright 2005 Miromico.
Mori, Narumi, et al. "Clinical assessment of a new method for pacing pulse detection using a hybrid circuit in digital Holter monitoring." Japanese circulation journal 64.8 (2000): 583-589.
Pyron, "Pyron Introduces ECG ASIC Monitoring Subsystem", Electronic News, Nov. 29, 1999.
Nguyen, Clark T-C., and Roger T. Howe. "An integrated CMOS micromechanical resonator high-Q oscillator." Solid-State Circuits, IEEE Journal of 34.4 (1999): 440-455.
Grossbach, Wolfgang. "Measuring the ECG Signal with a Mixed Analog-Digital Application-Specific IC." Hewlett-Packard Journal 42.4 (1991): 21-24. Abstract Only.

\* cited by examiner

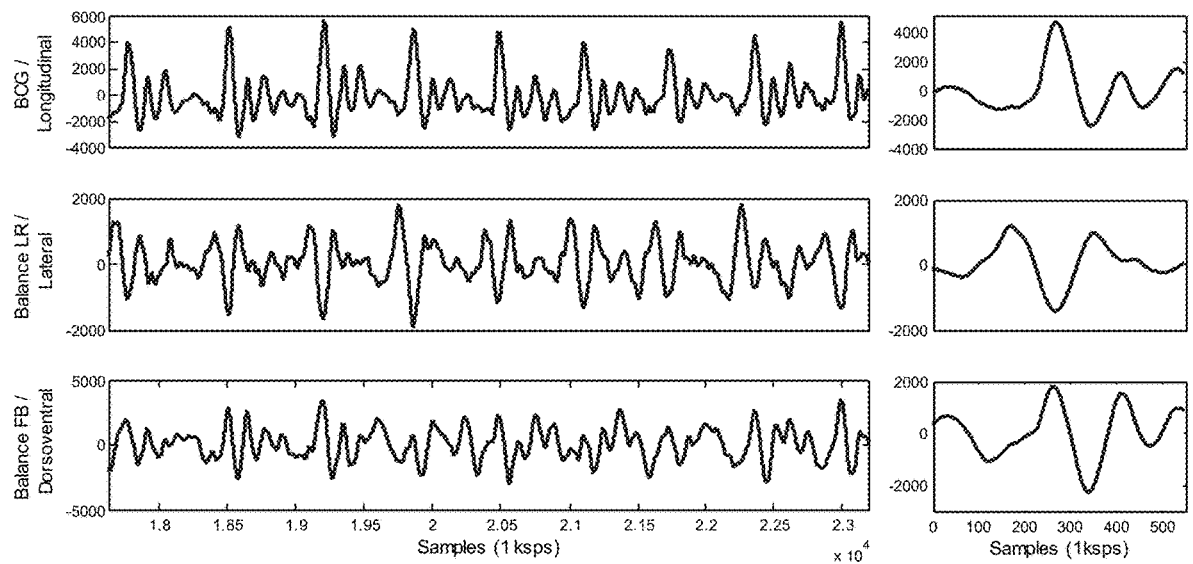
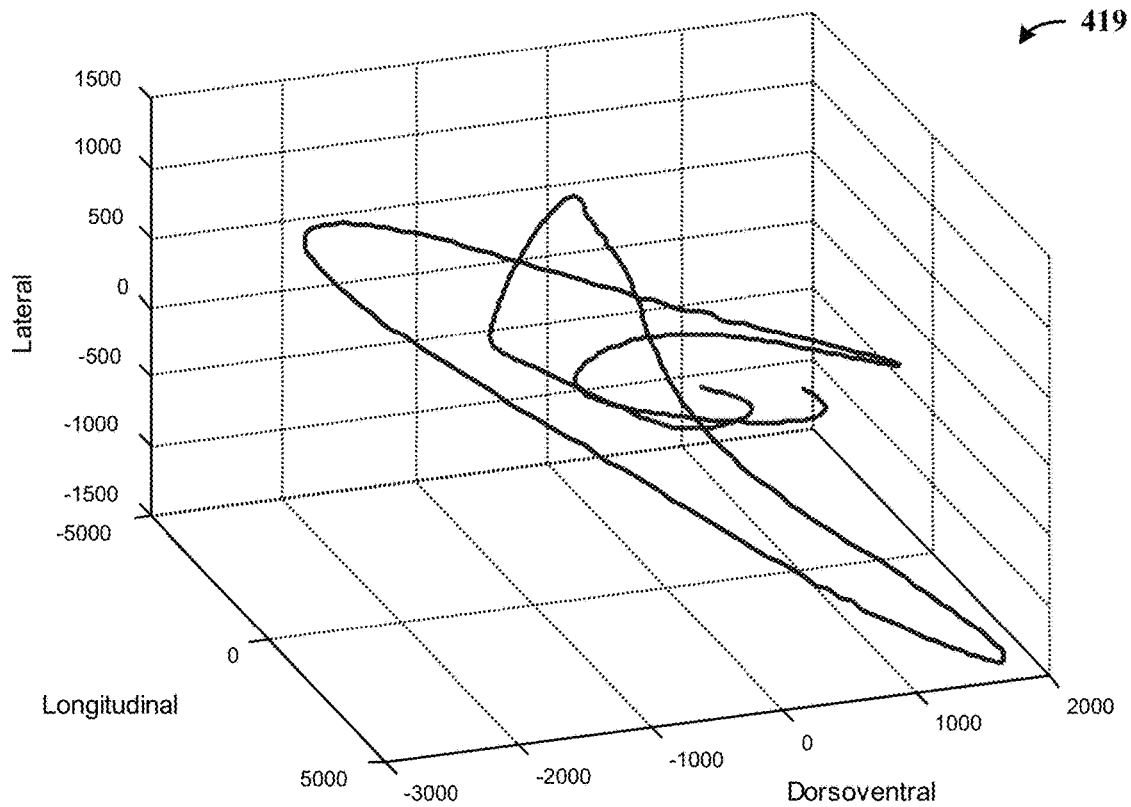
FIG. 4

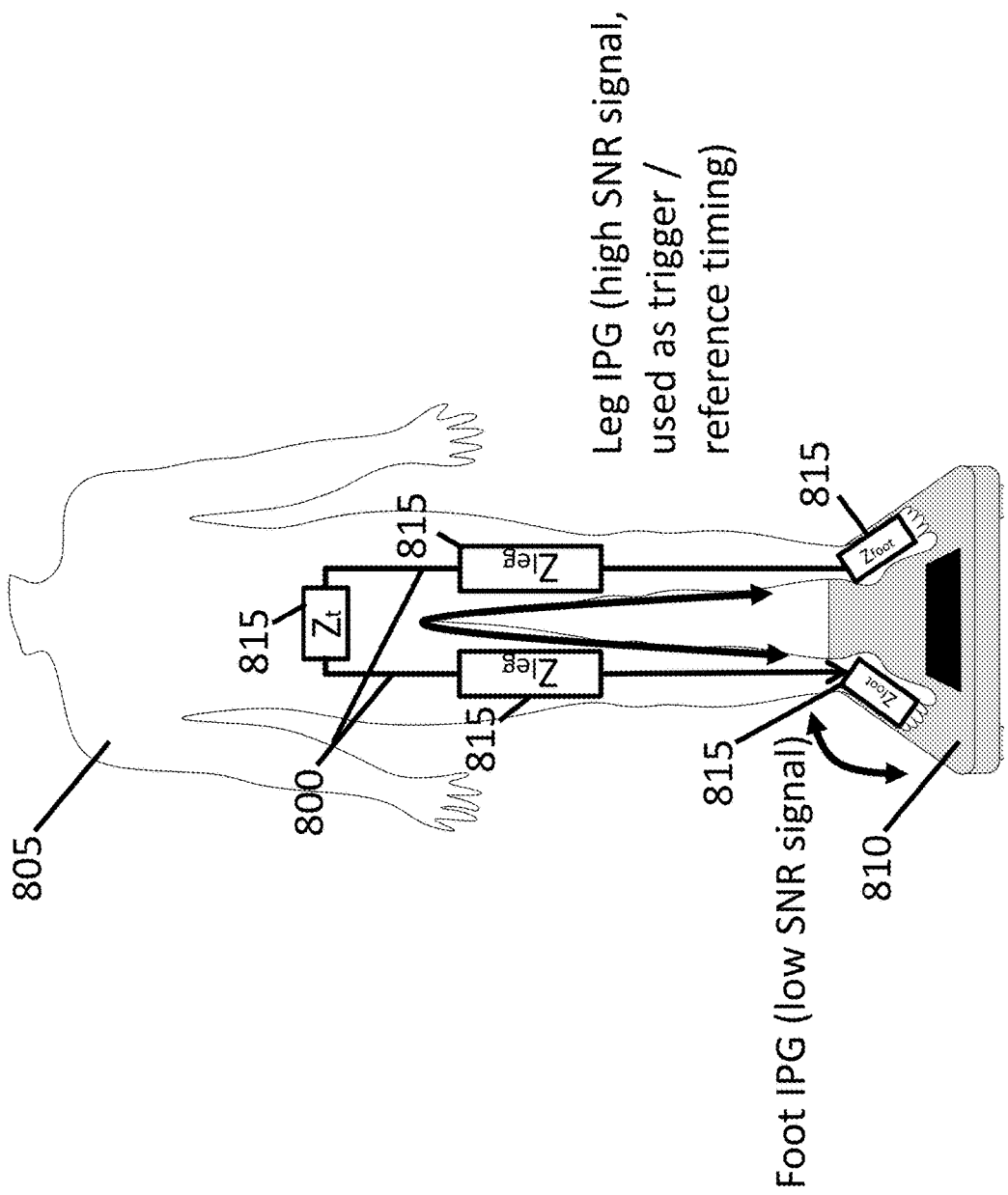

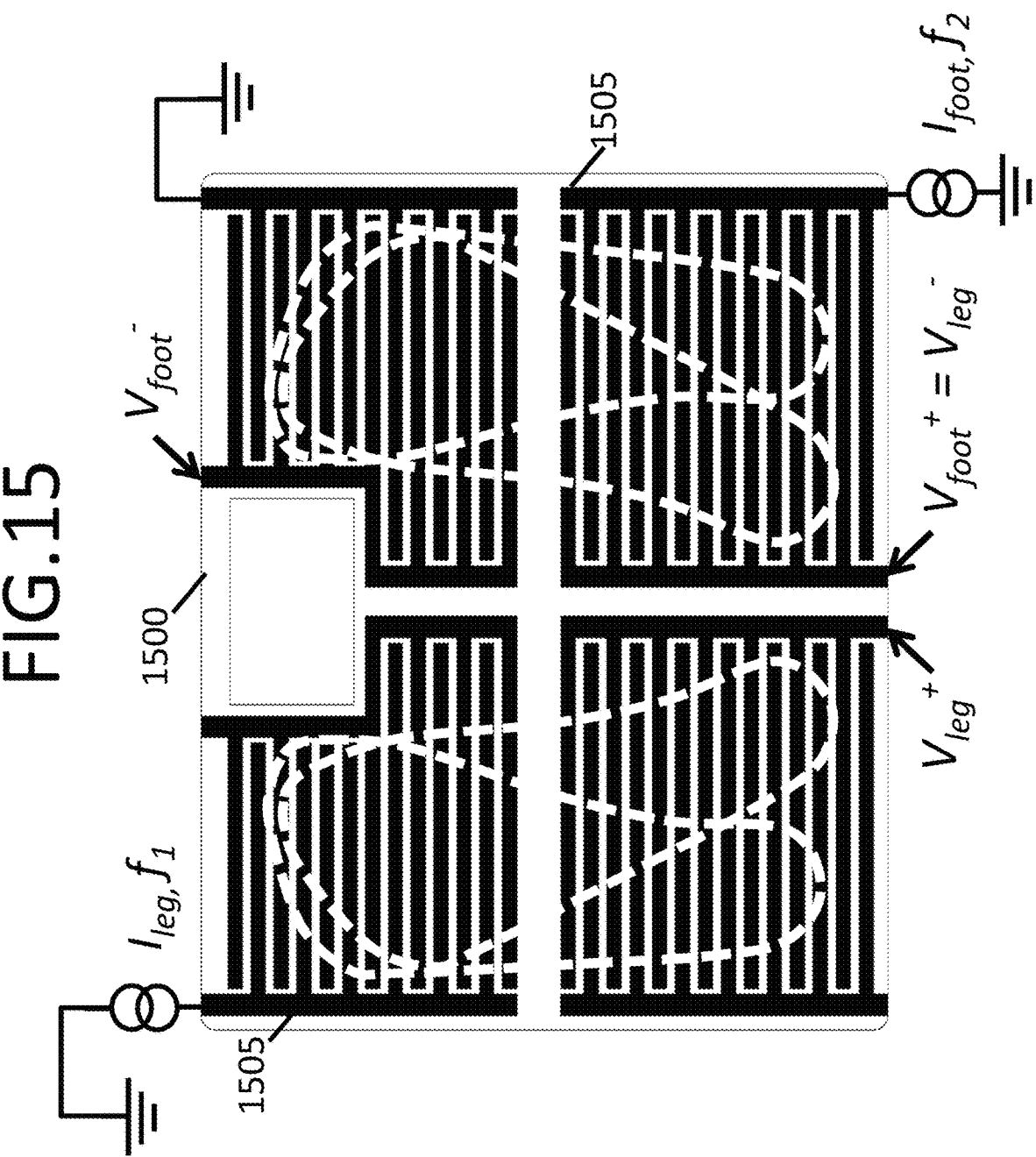

Switched, ground-referenced current source implementation

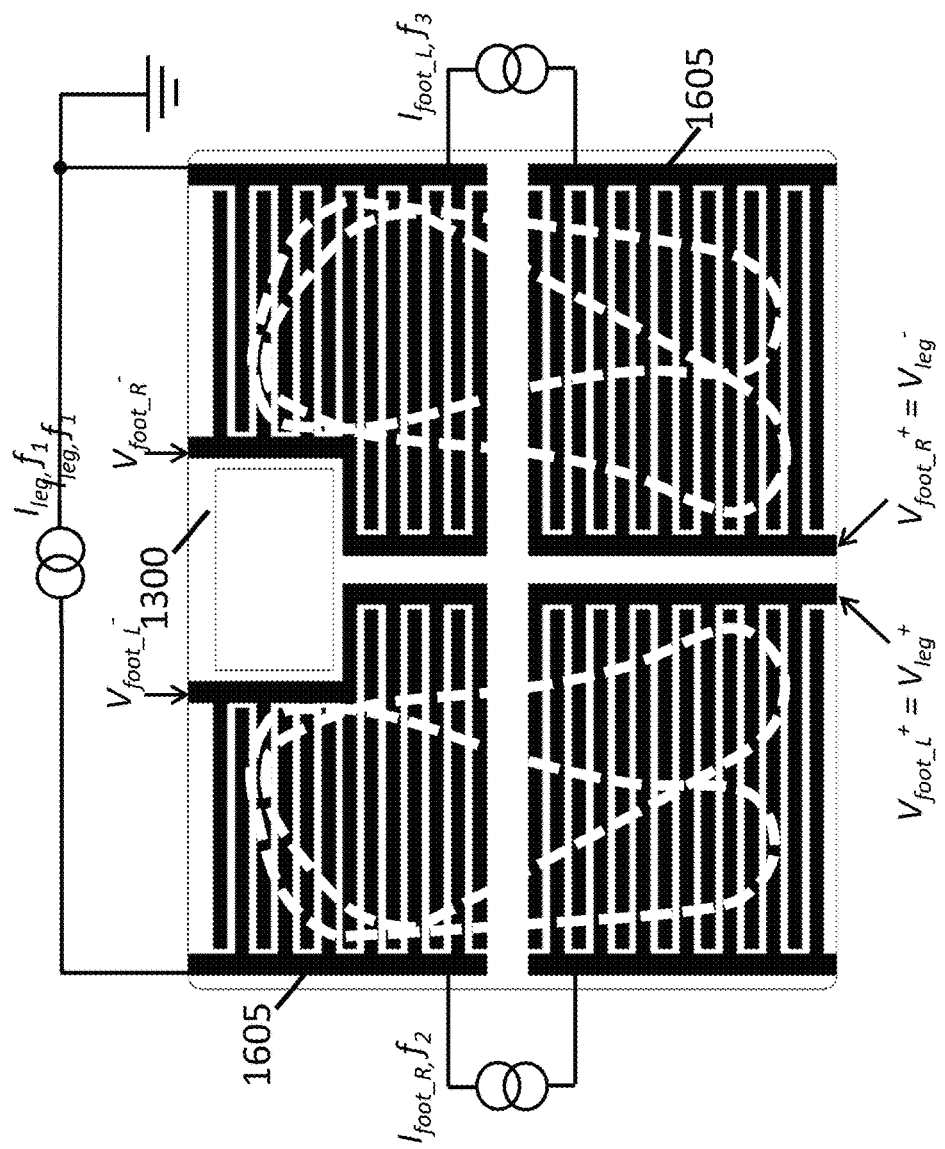

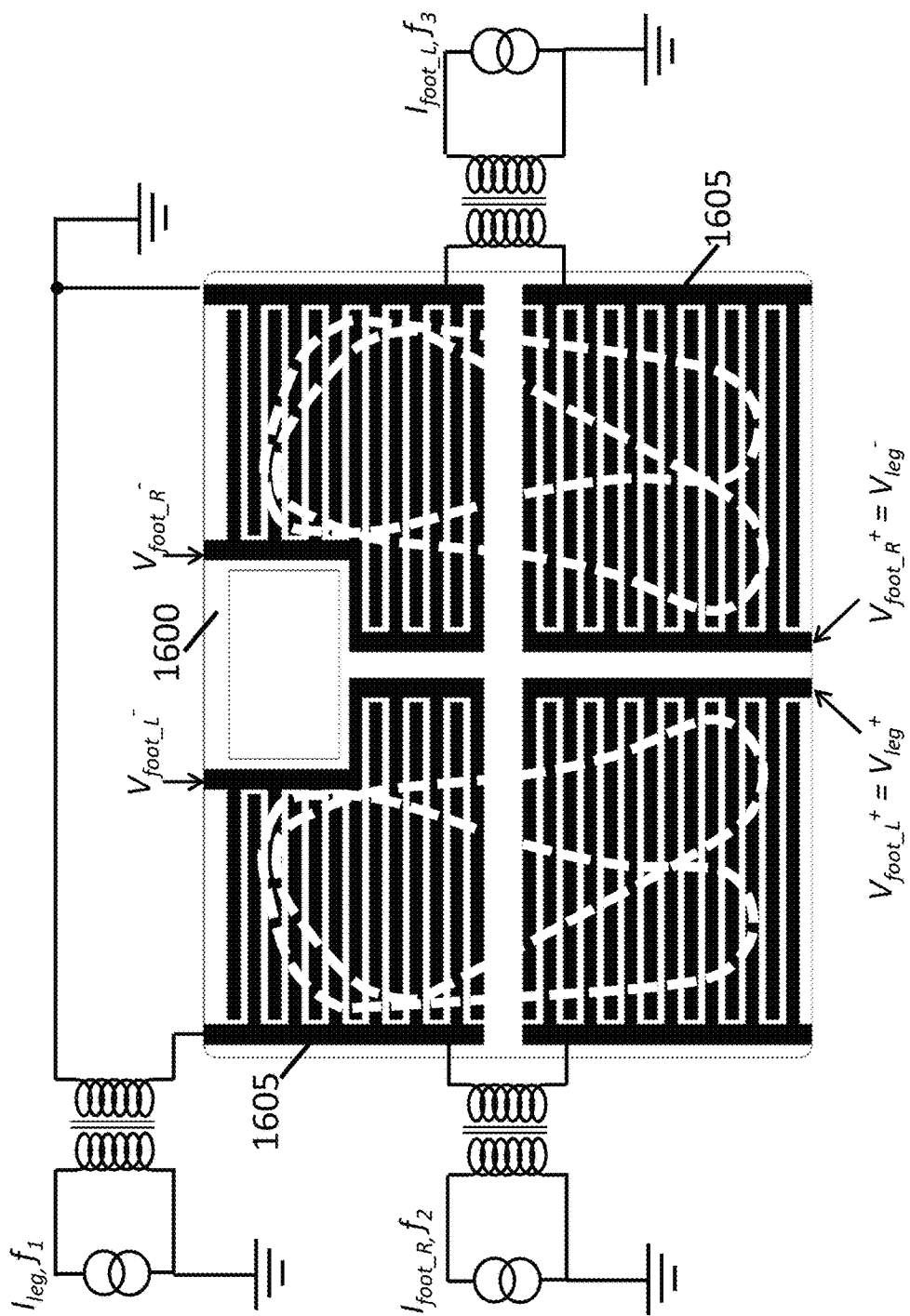

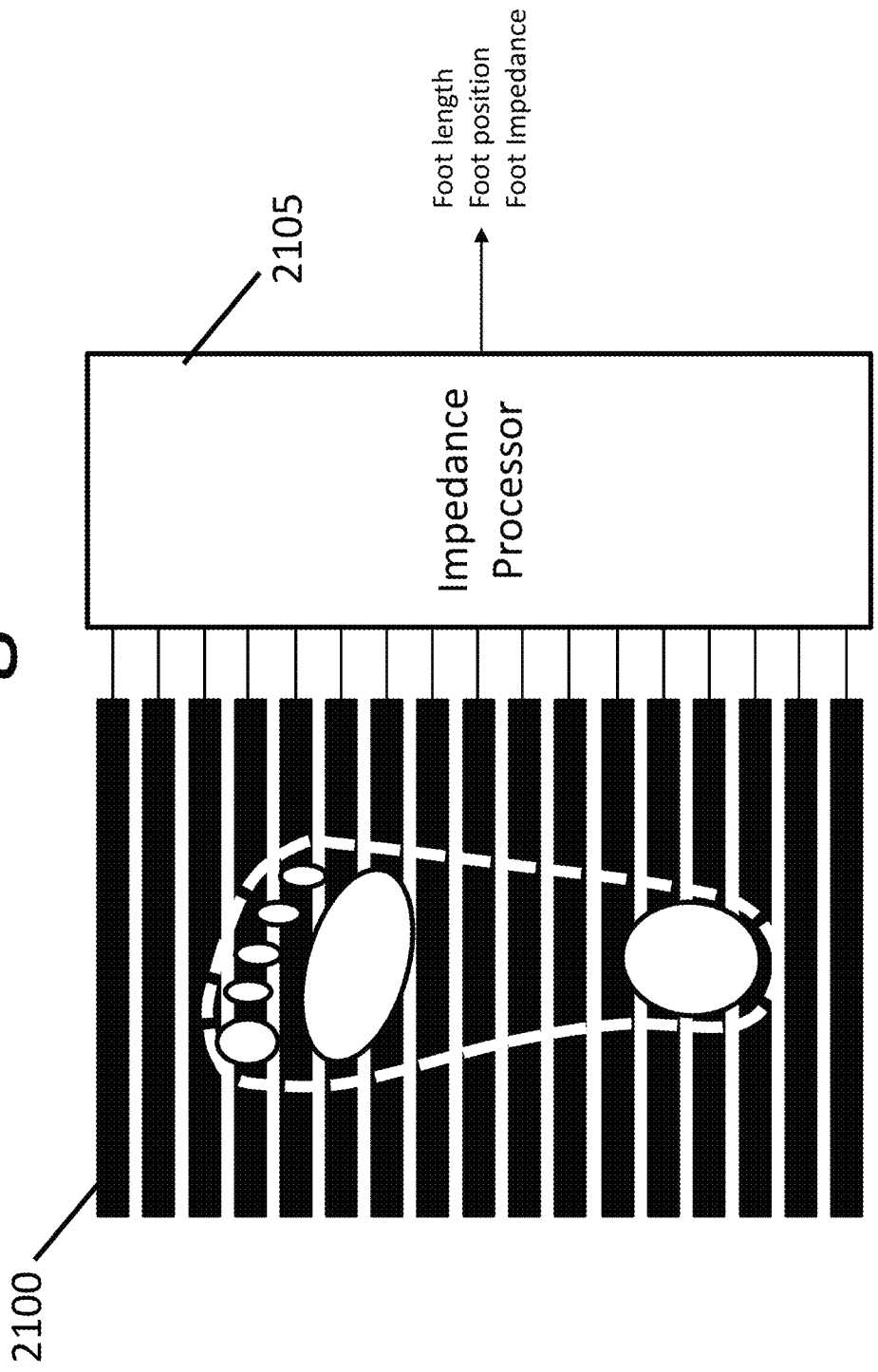

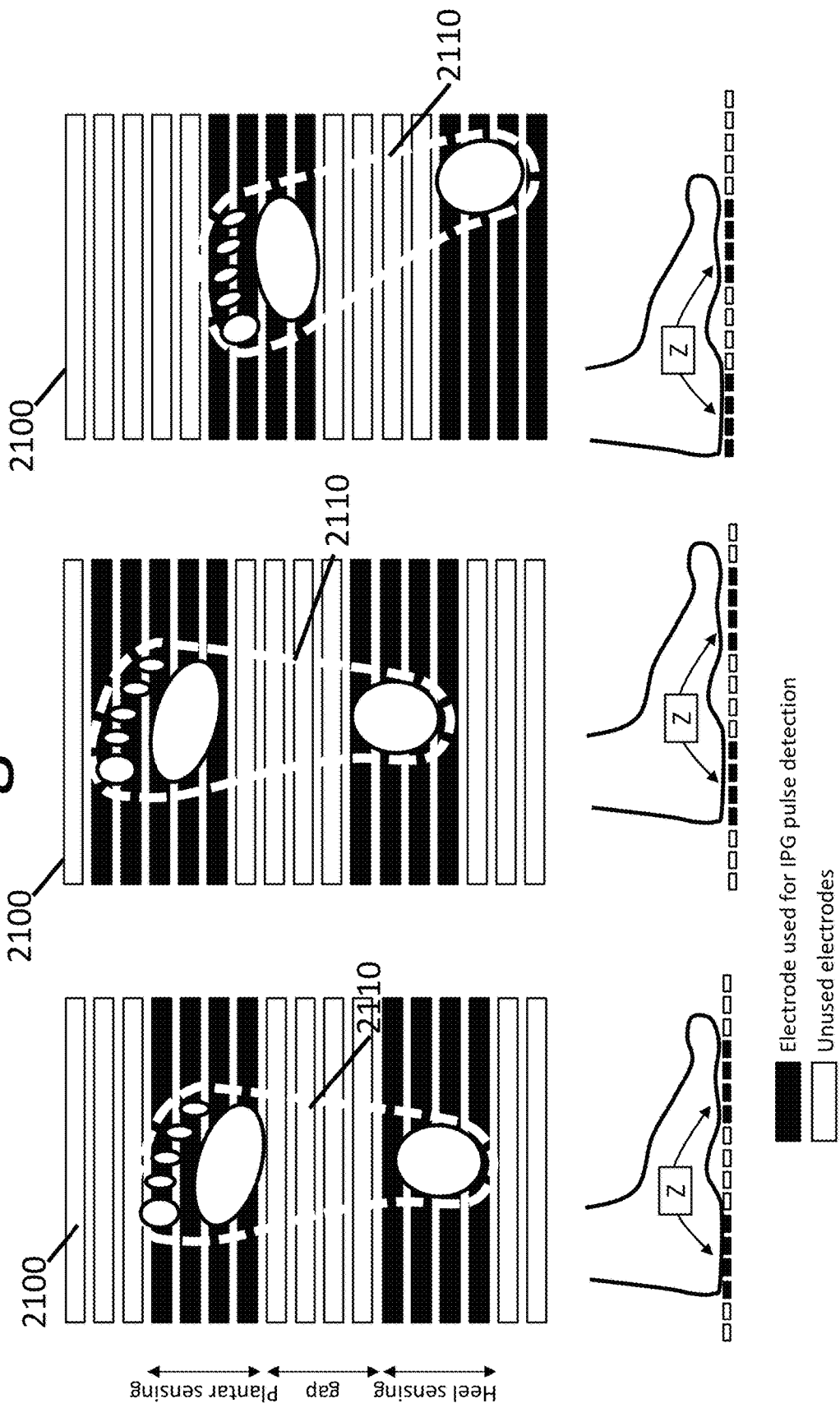

DETERMINING PHYSIOLOGICAL PARAMETERS USING MOVEMENT DETECTION

BACKGROUND

A variety of different physiological characteristics are monitored for many different applications. For instance, physiological monitoring instruments are often used to measure a number of patient vital signs, including blood oxygen level, body temperature, respiration rate and electrical activity for electrocardiogram (ECG) or electroencephalogram (EEG) measurements. For ECG measurements, a number of electrocardiograph leads may be connected to a patient's skin, and are used to obtain a signal from the patient.

Obtaining physiological parameters can often require specialty equipment from, and intervention by medical professionals. For many applications, such requirements may be costly or burdensome. These and other matters have presented challenges to monitoring physiological characteristics.

SUMMARY

Various aspects of the present disclosure are directed toward a user-support platform that can include and/or be implemented as a scale and multisensory biometric weighing scale devices, systems and methods. Biometrics is a broad term wherein this application includes the measurements of body composition and cardiovascular information. Measurements (impedance based and otherwise) can be made through the feet to measure fat percentage, muscle mass percentage, and body water percentage. Additionally, cardiovascular measurements can be made for an electrocardiogram (ECG) and sensing the properties of blood pulsations in the arteries, also known as impedance plethysmography (IPG), where such techniques can be used to quantify heart rate and/or pulse arrival timings (PAT). Cardiovascular IPG measures the change in impedance through the corresponding arteries between the sensing electrode pair segments synchronous to each heartbeat.

Other aspects of the disclosure are directed to a user platform apparatus, such as a weighing (e.g., bathroom) scale specifically designed for monitoring measurements of the user. The scale is equipped to monitor some or all of the following measurements: weight (e.g., bodyweight), body composition, hydration level, ballistocardiogram (BCG), impedance cardiogram (ICG), electrocardiogram (ECG), pulse wave velocity (PWV), photoplethysmogram (PPG) (or others) and from these provide both an instantaneous assessment of fitness as well as feedback for improvement.

A specific example embodiment is directed to an apparatus comprising a platform region configured and arranged with an area for the user to stand, a plurality of force sensors including sensor circuitry, and processor circuitry. The plurality of force sensors including the sensor circuitry are configured and arranged to provide a plurality of analog signals responsive to the user standing on the platform region and while the user is standing on the platform region. Further, the platform region is configured and arranged to engage the user with the plurality of force sensors while the user stands on the platform region. In addition, the processor circuitry is configured and arranged to process the analog signals from the plurality of force sensors, detect movement of the user, corresponding to a graphical representation of cardiac movements including movements between heart beats of the user's heart, using the processed analog signals, and determine cardiac physiological parameters of the user using the detected movement and the analog signals.

For example, the processor circuitry is configured and arranged to determine cardiac physiological parameters of the user corresponding to a graphical representation of cardiac movements including movements between heart beats of the user's heart, by processing the analog signals from the sensor circuitry, mitigating at least some effect on the analog signals attributable to postural sway of the user while the user stands on the platform region, and generating data indicative of the physiological parameters based on said processing of the analog signals from the sensor circuitry and the mitigating of at least some of the effect on the analog signals attributable to postural sway of the user while the user stands on the platform region.

Another example embodiments is directed to an apparatus comprising a platform region configured and arranged with an area for the user to stand. The apparatus includes a base unit and processor circuitry. The base unit is configured and arranged to integrate a support structure. The support structure includes the platform region and a plurality of force sensors therein. The plurality of force sensors including sensor circuitry are configured and arranged to provide a plurality of analog signals responsive to the user standing on the platform region and while the user is standing on the platform region, the platform region being configured and arranged to engage the user with the plurality of force sensors while the user stands on the platform region. The processor circuitry is configured and arranged to determine cardiac physiological parameters of the user corresponding to a graphical representation of cardiac movements including movements between heart beats of the user's heart, by processing the analog signals from the sensor circuitry, mitigating at least some effect on the analog signals attributable to postural sway of the user while the user stands on the platform region, the postural sway including at least one of tilt and lean movement of the user relative to a nominal-still position of the user and generating data indicative of the cardiac physiological parameters based on said processing of the analog signals from the sensor circuitry and the mitigating of at least some of the effect on the analog signals attributable to postural sway of the user while the user stands on the platform region.

The apparatus embodiments can be used to perform a variety of methods. An example method embodiment includes detecting analog signals indicative of movement of a user using an apparatus, the apparatus including circuitry to engage with a user to measure the analog signals and process the measured analog signals. Further, the method includes detecting postural sway of a user standing on the apparatus using the processed analog signals, and determining cardiac physiological signals indicative of a cardiac physiological parameter of the user in at least two of a longitudinal, lateral, and dorsoventral direction using the detected postural sway and the processed analog signals. In various embodiments, the method includes determining a cardiac physiological parameter of the user using the cardiac physiological signals indicative of the cardiac physiological parameter in at least two of the longitudinal, lateral, and dorsoventral directions, and communicating, using the circuitry, the cardiac physiological parameter to the user.

In other related aspects, an apparatus includes a platform region configured and arranged with an area for a user to stand and force-sensor circuitry configured and arranged to provide or generate analog signals responsive to the user standing on the platform region and while the user is standing on the platform region, the platform region being configured and arranged to engage the user with the plurality of force sensors while the user stands on the platform region. The apparatus further includes circuitry configured and arranged to determine cardiac physiological parameters of the user corresponding to a graphical representation of cardiac movements including movements between heart beats of the user's heart, by processing the analog signals from the sensor circuitry, mitigating at least some of the effect on the analog signals attributable to postural sway of the user while the user stands on the platform region, and generating data indicative of the cardiac physiological parameters based on said processing of the analog signals from the sensor circuitry and the mitigating at least some of the effect on the analog signals attributable to postural sway of the user while the user stands on the platform region. In various embodiments, wherein the effect on the analog signals attributable to postural sway of the user corresponds to one of longitudinal, lateral, dorsoventral cardiac physiological signals, and a combination thereof. In some aspects, the circuitry configured and arranged to determine cardiac physiological parameters is further configured and arranged to effectively remove the effect on the analog signals attributable to postural sway of the user. For example, the circuitry is configured and arranged to determine cardiac physiological parameters is further configured and arranged to effectively remove the effect on the analog signals attributable to postural sway of the user as corresponding to at least one of lateral cardiac physiological signals and dorsoventral cardiac physiological signals.

This description is intended to be illustrative of one of many possible embodiments of the invention and not to be limiting.

DESCRIPTION OF THE FIGURES

Various example embodiments may be more completely understood in consideration of this detailed description and in connection with the accompanying drawings, in which:

FIG. 4 shows a graph illustrating a longitudinal cardiac physiological signal, a lateral cardiac physiological signal, and a dorsoventral cardiac physiological signal, and another graph illustrating a three-dimensional cardiac physiological parameter, consistent with various aspects of the present disclosure;

FIG. 7 shows a weighing scale with a large-area display, consistent with various aspects of the present disclosure;

FIG. 8B shows current paths through the body for the IPG trigger pulse and Foot IPG, consistent with various aspects of the present disclosure;

FIG. 15 shows another example of a scale with interleaved foot electrodes to inject and sense current from one foot to another foot, and within one foot, consistent with various aspects of the present disclosure;

FIG. 16B shows another example of a scale with interleaved foot electrodes to inject and sense current from one foot to another foot, and to measure Foot IPG signals in both feet, consistent with various aspects of the present disclosure;

FIG. 16C shows another example approach to floating current sources by using transformer-coupled current sources, consistent with various aspects of the present disclosure;

FIGS. 21A-C show example impedance as measured through different parts of the foot based on the foot position, consistent with various aspects of the present disclosure.

Figure 1A:
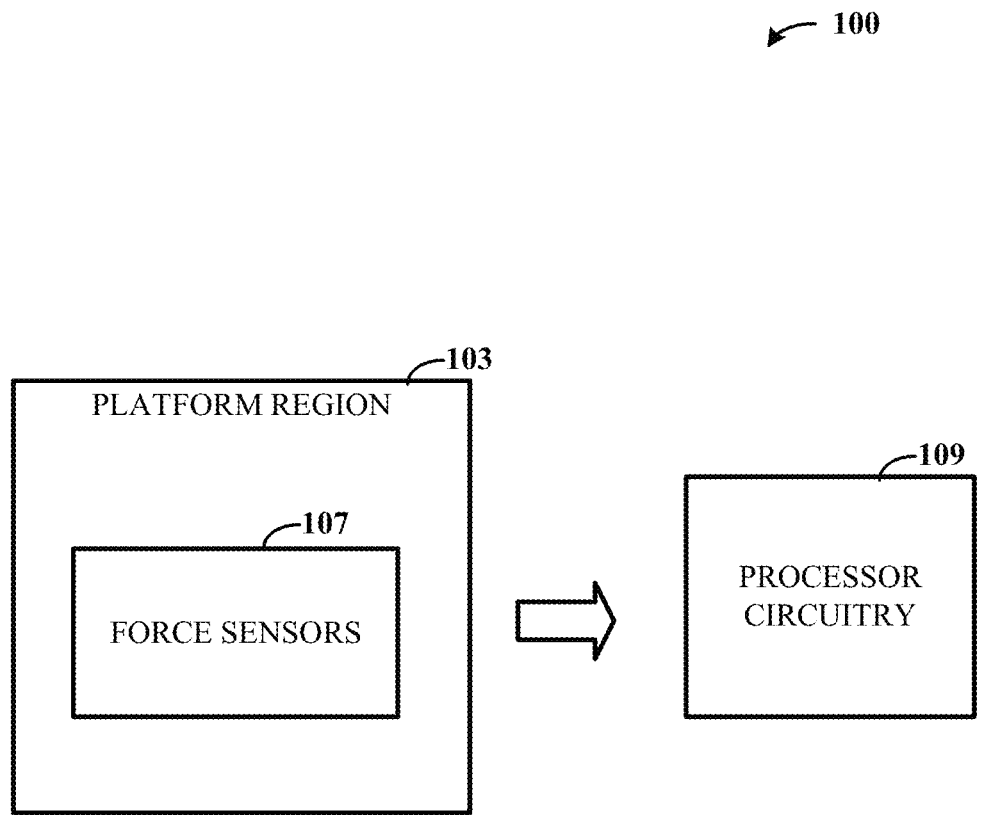
FIG. 1A shows an example apparatus comprising a platform region, force sensors, and a processing circuit, consistent with various aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Various aspects of the present disclosure are directed toward an apparatus, such as a weighing scale, with a large-area display to present results of the apparatus' multiple sensing functionalities, as well as other information pertinent to a user. In many embodiments, a scale is capable of a number of biometric and physiological measurements. Based on the measurements, a physiological condition(s) of the user is displayed on the large-area display between or beneath the user's feet.

In various embodiments a scale including a display is disclosed, the display being effectively the entire top surface of the scale. Support glass above the display transmits the weight of a user to a bezel along the perimeter of the scale (away from the display), while also transmitting touch-capacitive signals indicative of a user's position and movement on the support glass through the display to scale circuitry. The bezel houses load cells equally spaced along the perimeter of the scale. Each load cell outputs an electrical signal indicative of a mass transmitted from the user through the load cell to the scale circuitry. A support frame is attached to the bezel and supports the display within the bezel. A plurality of force sensors are embedded into the support glass to provide analog signals indicative of movement (e.g., balance movement/postural sway) of the user. Further, in some embodiments, a plurality of translucent electrode leads are embedded into the support glass to provide electrical signals, including the analog signals, to the processor circuitry of the scale; and the electrical signals are interpreted by the processor circuitry as being indicative of a condition of a user, such a physiological condition being presented on the display for the user.

The analog signals obtained by the force sensors, in various embodiments, include changes in electrical resistance of the force sensors. For example, when a user shifts weight from their left foot to their right foot, the electrical resistance of one or more of the force sensors changes. The change in electrical resistance of the force sensors can be used to detect movement of the user (e.g., balance movement). Surprisingly, it has been discovered that tilting or leaning (balance) movements of the user can be used to obtain reliable cardiac physiological parameters, such as BCG parameters, from the analog signals obtained by the force sensors. For example, processor circuitry of the scale processes the analog signals to detect the movement of the user while the user is standing on the platform region and determine cardiac physiological parameters of the user using the detected movement and the analog signals. The movement is relative to a person standing in a nominal-still position on the platform region. The determined cardiac physiological parameters, in various embodiments, can be determined using cardiac physiological signals indicative of the cardiac physiological parameter in lateral, dorsoventral, and/or longitudinal directions. The cardiac physiological signals can be extracted from the analog signals, as described further herein. In various embodiments, the various cardiac physiological signals in multiple directions are used to determine a two-dimensional and/or three-dimensional (3D) cardiac physiological parameter (e.g., a 3D BCG parameter) of the user.

For example, using an apparatus with force sensors, left-right (e.g., tilt) and forward-backward (e.g., lean) balancing by the user is detected. The changes in electrical resistance can cause, for example, different analog signals from each of the force sensors. For example, the analog signals contain features that are synchronous with the heartbeat and indicative of forces generated by blood flow in the arteries (e.g., BCG parameter). For example, such features are indicative of two or more orthogonal components of the three-dimensional BCG signal (e.g., vector). Thereby, the analog signals can be used to detect the BCG parameter in multiple directions while a user is standing on the scale, as the scale apparatus is sensitive to the detection of balance movement (e.g., off-axis forces).

In further, more specific, embodiments of the present disclosure, a scale is communicatively coupled with a user's external device, such as portable electronic devices, an internet router, or other home electronic devices. The scale then communicates and exchanges data with these devices for display and control by a user. In various embodiments, while the scale is conducting biometric and physiological measurements of the user, the user (by way of the touch-responsive screen) browses today's news communicated to the scale by the internet router, changes the station on the television or the song playing on a sound system, or reviews their schedule transmitted to the scale by the user's smartphone.

In yet further implementations of the disclosure directed to smart-homes, a scale is used by the user to control (via the touch-screen display) a plurality of other devices throughout the home such as a climate control system, security system, operation of the shower, etc. The electronic communications between the scale and the various devices, in some embodiments, include wireless and/or wired communications.

Aspects of the present disclosure are directed to an apparatus comprising a platform region, a plurality of force sensors, and processor circuitry. The platform region includes an area for the user to stand and engages the user with the plurality of force sensors while the user stands on the platform region. The plurality of force sensors including sensor circuitry are configured and arranged to provide a plurality of analog signals responsive to the user standing on the platform region and while the user is standing on the platform region. The processor circuitry, in various embodiments, processes the analog signals from the plurality of force sensors, detects movement of the user using the processed analog signals, and determines cardiac physiological parameters of the user using the detected movement and the analog signals. For example, the processor circuitry can determine cardiac physiological parameters of the user corresponding to a graphical representation of cardiac movements including movements between heart beats of the user's heart, by processing the analog signals from the sensor circuitry, mitigating at least some effect on the analog signals attributable to postural sway of the user while the user stands on the platform region, and generating data indicative of the physiological parameters based on said processing of the analog signals from the sensor circuitry and the mitigating of at least some of the effect on the analog signals attributable to postural sway of the user while the user stands on the platform region.

Some embodiments are directed to an apparatus comprising a platform region, a base unit and processor circuitry. The platform region is configured and arranged to engage the user with the plurality of force sensors while the user stands on the platform region. The base unit is configured and arranged to integrate a support structure (and in some embodiments, a display). The support structure includes the platform region and the plurality of force sensors therein. The plurality of force sensors including sensor circuitry are configured and arranged to provide a plurality of analog signals responsive to the user standing on the platform region and while the user is standing on the platform region. The processor circuitry, in a number of embodiments, determines cardiac physiological parameters of the user corresponding to a graphical representation of cardiac movements including movements between heart beats of the user's heart, by processing the analog signals from the sensor circuitry, mitigating at least some effect on the analog signals attributable to postural sway of the user while the user stands on the platform region, the postural sway including at least one of tilt and lean movement of the user relative to a nominal-still position of the user, and generating data indicative of the cardiac physiological parameters based on said processing of the analog signals from the sensor circuitry and the mitigating of at least some of the effect on the analog signals attributable to postural sway of the user while the user stands on the platform region.

Various aspects of the disclosure are directed to a scale with a large-area display. The large-area display is programmed to display aesthetically pleasing screen savers, both when in use, or idle. For example, images, animations, and videos, may be presented on the display with overlaid information (as may be selected by the user). In some specific embodiments of the present disclosure, where the scale, and based on its measurements, has determined a physiological condition in the user indicative of increased stress levels (as indicated by high blood pressure, heart rate, etc.), for example; the scale displays images or video, such as waves lapping over sand and play accompanying sounds or music, among other sensory devices, intended to calm and sooth the user. In yet further embodiments, based on an assessed condition, as indicated by the scale measurements, the scale suggests audibly or visually (through the scale's display) activities, dietary restrictions, or in the case where the indicated condition is life-threatening (e.g., measurements indicating an imminent heart attack or stroke, etc.), calls an ambulance for the user.

Example display devices include a touch responsive screen located across the top surface of the apparatus and/or other display devices located underneath the platform structure. In various embodiments, the display structure includes a capacitive matrix on its surface and/or is conductively coupled to the platform structure to prevent excessive weight from being exerted on the display structure.

The base structure including the support structure, in some embodiments, includes a set of electrodes, and a pulse-processing circuitry. The pulse-processing circuitry is communicatively coupled to, and configured with, the set of electrodes to obtain impedance signals while each of the electrodes is concurrently contacting the user, as discussed further herein. The supports structure includes the platform region and sensor circuitry. The support structure is located around the perimeter of the apparatus and transfers the weight of the user on the platform structure through load cells in each corner of the support structure. The platform structure engages with the sensor circuitry while the user stands on the platform structure and physiological data is collected from the user via the sensor circuitry. One way for platform structure to engage with the sensor circuitry while the user stands on the platform structure and for collecting physiological data includes the set of electrodes to contact the platform structure with the sensor circuitry.

The above discussion/summary is not intended to describe each embodiment or every implementation of the present disclosure. The figures and detailed description that follow also exemplify various embodiments.

Turning now to the figures, FIG. 1A shows an example apparatus 100 comprising a platform region 103, force sensors 107, and processor circuitry 109, consistent with various aspects of the present disclosure. The platform region 103 includes an area on which a user may stand. A plurality of force sensors 107, in some embodiments, include sensor circuitry and are arranged within the platform region 103. The force sensors 107 generate and/or provide a plurality of analog signals while the user is standing on the platform region 103. In this manner, the platform region 103 engages the user with the plurality of force sensors 107 while the user stands on the platform region 103.

The force sensors 107, in various embodiments, include strain gauges. The force sensors 107 can be arranged in the four corners of the platform region 103 and are used to detect balance movements of the user. Alternatively, in various embodiments, the force sensors 107 can be arranged in the center of the platform region 103 (e.g., the force sensors 107 can be located/grouped in a single load cell on which the platform in fitted). For example, the user, while balancing, can move in a lateral (e.g., lean or front to back) direction or dorsoventral (e.g., tilt or side to side) direction relative to a nominal-still position of the user. The movement can include postural sway, such as shifting of weight from the front of the feet (e.g., the toes) to the back of the feet (e.g., the heels) and/or between feet. Surprisingly, such movement, as discussed further herein, can be used to determine cardiac physiological parameters of the user. A nominal-still position of the user can include a position of the user, while standing, without balance movement. Such a position, however, can be a hypothetical position and/or may be momentarily achieved by a user. For example, balancing is the ability of the user to maintain the line of gravity of their body with postural sway (e.g., involuntary tilt and lean movement while the user is standing and balancing upright on the platform). A certain amount of (minimal) sway can be inevitable due to small perturbations within the body and/or external triggers.

In some embodiments, the processor circuitry 109 determines cardiac physiological parameters of the user corresponding to a graphical representation of cardiac movements including movements between heart beats of the user's heart. For example, the processor circuitry 109 can processes the analog signals from the force sensors 107 and detects postural sway of the user using the processed analog signals. The postural sway and/or movement can include lateral movement (e.g., lean or left-right balance shifting)

and dorsoventral movement (e.g., lean or front-back balancing shifting). The analog signals include changes in electrical resistance of the force sensors 107. The processor circuitry 109 detects the movement, in various embodiments, by differential sensing of opposed force sensors 107 to detect force differences between the force sensors 107. Further, the processor circuitry 109 determines cardiac physiological parameters of the user using the detected movement and the processed analog signals.

For example, the processor circuitry can determine the cardiac parameters by mitigating at least some effect on the analog signals attributable to postural sway of the user while the user stands on the platform region (e.g., the postural sway including at least one of tilt and lean movement of the user relative to a nominal-still position of the user) and generating data indicative of the cardiac physiological parameters based on said processing of the analog signals from the sensor circuitry and the mitigating of at least some of the effect on the analog signals attributable to postural sway of the user while the user stands on the platform region. The effect on the analog signals attributable to postural sway can be mitigated by estimating a baseline wander and removing the baseline wander from the analog signals, as discussed further herein.

The generated data, in various embodiments, can include at least one of a cardiac physiological signal indicative of the cardiac physiological parameter in a particular direction. For example, a cardiac physiological parameters can be determined using cardiac physiological signals indicative of the cardiac physiological parameter in a number of directions. In some embodiments, the cardiac physiological signals can be extracted from the analog signals using one or more filters. In various embodiments, the cardiac physiological signal can be indicative of a BCG parameter in a direction, such as longitudinal, lateral, and/or dorsoventral directions.

The processor circuitry 109 can extract the cardiac physiological signals indicative of the cardiac physiological parameter in multiple directions (and/or detecting movement) by, in various embodiments, comparing the analog signals of particular force sensors 107. As previously discussed, the force sensors 107 can be arranged in each of the corners of the platform region 103 and/or in the center of the platform region 103. For example, a force sensor can be located in each corner of the platform region 103, for a total of four force sensors. To determine a cardiac physiological signal indicative of a cardiac physiological parameter in a lateral direction, the processor circuitry 109 compares analog signals from force sensors (e.g., a first subset of the plurality of force sensors) associated with a first foot (e.g., left foot) of the user standing on the platform region 103 to analog signals from force sensors (e.g., a second subset of the plurality of force sensors) associated with a second foot (e.g., right foot). To determine a cardiac physiological signal indicative of a cardiac physiological parameter in a dorsoventral direction, the processor circuitry 109 compares analog signals from force sensors (e.g., a first subset of the plurality of force sensors) associated with a first portion of feet of the user (e.g., the toes of the user) to analog signals from force sensors (e.g., a second subset of the plurality of force sensors) associated with a second portion of the feet of the user (e.g., the heels).

In various embodiment, the force sensors 107 detect force differences between sides of the platform region 103, which can be similar to torque. In some embodiments, the apparatus detects differential forces between sides of the apparatus 100 (e.g., front to back/left to right) on an order of 0.05 Newtons (N) applied on the side of the apparatus 100, that can be caused by a movement of the user as may be represented by the equation 1 mN*m. For example, the detection of movement can be performed by direct sampling of individual strain gauges.

By detecting the movement and/or postural sway of the user, in various embodiments, the baseline wander of the cardiac physiological signal can be removed. For example, the baseline wander can be removed from the analog signals to obtain at least one cardiac physiological signal indicative of the cardiac physiological parameter. In some instances, the baseline wander is larger than the cardiac physiological signals indicative of the cardiac physiological parameter (such as a BCG parameter) in the lateral and dorsoventral directions and removal of the baseline wander can result in uncovering the cardiac physiological signal indicative of the cardiac physiological parameter in the particular direction. Example baseline wander techniques include high-pass filtering, moving averages, Savitzky-Golay filtering, Whittaker smoother-based filtering, parametric, non-parametric and adaptive fittings, statistical methods (e.g., principal component analysis, entropy-based, Kalman filtering), and wavelet filtering, among other techniques.

In some embodiments, a second sensor, such as an ECG, IPG, PPG, and accelerometer, is used to further de-noise the cardiac physiological signal, and extract a template for the cardiac physiological signal indicative of the cardiac physiological parameter in all three directions (e.g., lateral, dorsoventral, and longitudinal). Other de-noising techniques, in various embodiments, can be applied.

In accordance with various embodiments, an apparatus can include additional components and/or features not illustrated by FIG. 1A. For example, the apparatus can include a base unit. The base unit integrates a support structure, a display, and/or the processor circuitry. The support structure can include the platform region and sensor circuitry. The sensor circuitry, in various embodiments, includes the plurality of force sensors. The display is configured with the support structure for displaying data through the platform region for view by the user while the user stands on the platform region. Further, as one in the art may appreciate, the various aspects of the present disclosure can be combined in a variety of manners.

In various embodiments, the processor circuitry includes a variety of circuits. For example, the processor circuitry can include user-targeted circuitry configured and arranged to communicate user-specific data between the user and the user-targeted circuitry. Alternatively and/or in addition, the processor circuitry can include an interface circuit. The interface circuit can drive the display and the display can be configured to output signals to the interface circuit. The output signal, in some embodiments, is indicative of the cardiac physiological parameter and the interface circuit, responsive to the output signal, tracks cardiac physiological parameters in multiple directions (e.g., longitudinal, lateral, and dorsoventral) over time. The interface circuit can be a component of the apparatus 100 and/or an external device.

In some embodiments, the sensor circuitry additionally includes electrodes (e.g., current-impedance electrodes) configured and arranged to contact the user and obtain impedance signals, as further discussed herein. For example, the processor circuitry, in such embodiments, determines cardiac physiological parameters using the analog signals and detected movement (e.g., BCG signals in a lateral, dorsoventral, and/or longitudinal direction) and determines cardiac physiological parameters using the impedance signals (e.g., a two-dimensional and/or three-dimensional BCG parameter or other parameters).

Figure 1B:
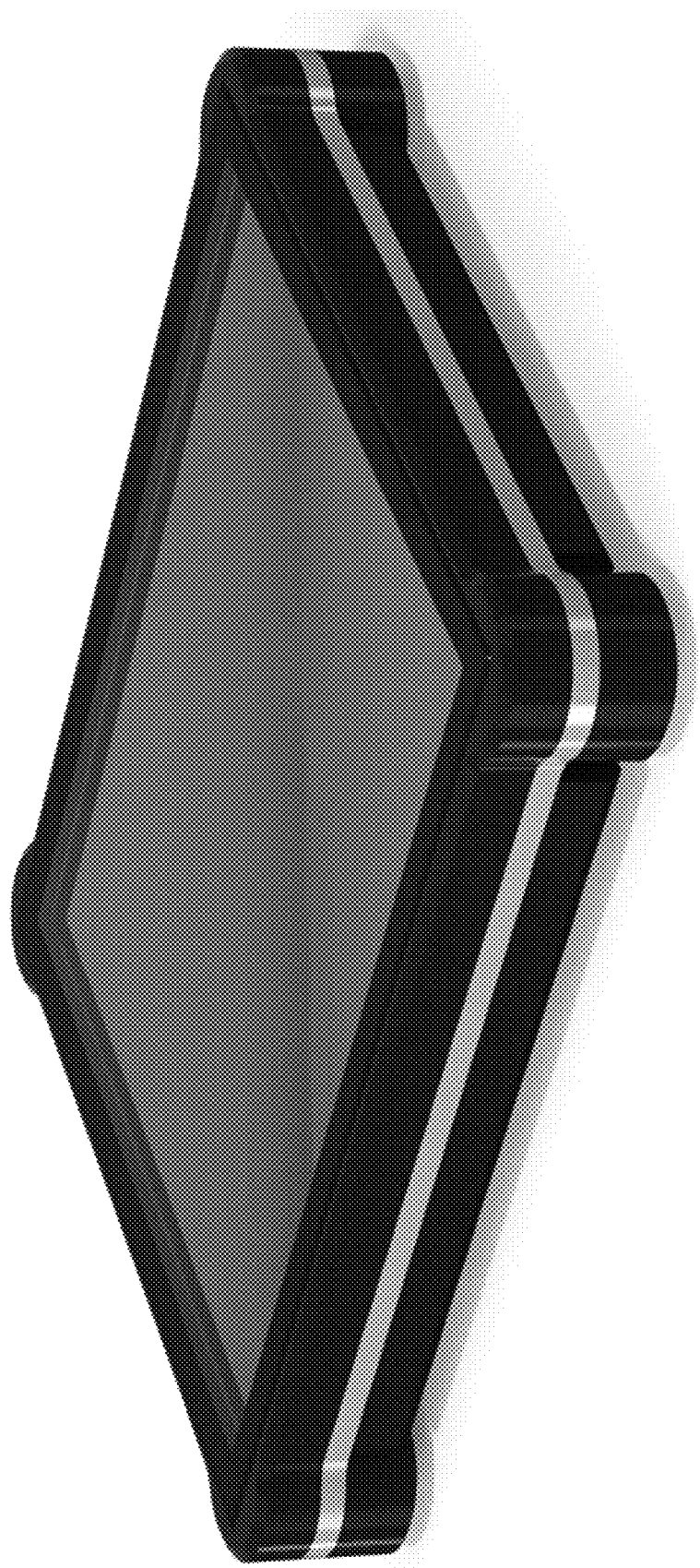
FIG. 1B shows an isometric view of a weighing scale with large-area display, consistent with various aspects of the present disclosure.

FIG. 1B shows an isometric view of a scale with a large-area display, consistent with various aspects of the present disclosure. In this particular embodiment, the scale has a primarily rectangular shape with a bezel around the perimeter of the scale that transfers the weight of a user from a top surface of the scale through load cells in each corner. It is to be understood that the aesthetic design of the scale may take on a plurality of shapes and sizes (based on the needs of the users, e.g., weight requirements, aesthetic preferences, etc.). A feature of the scale is the large-area display that makes up the majority of the top surface of the scale. The display, in some embodiments, presents the user with a myriad of information, such as the results of physiological and biometric test results conducted by the scale, entertainment information (while the scale is conducting tests or a weight measurement), and aesthetic screen savers.

Figure 1C:
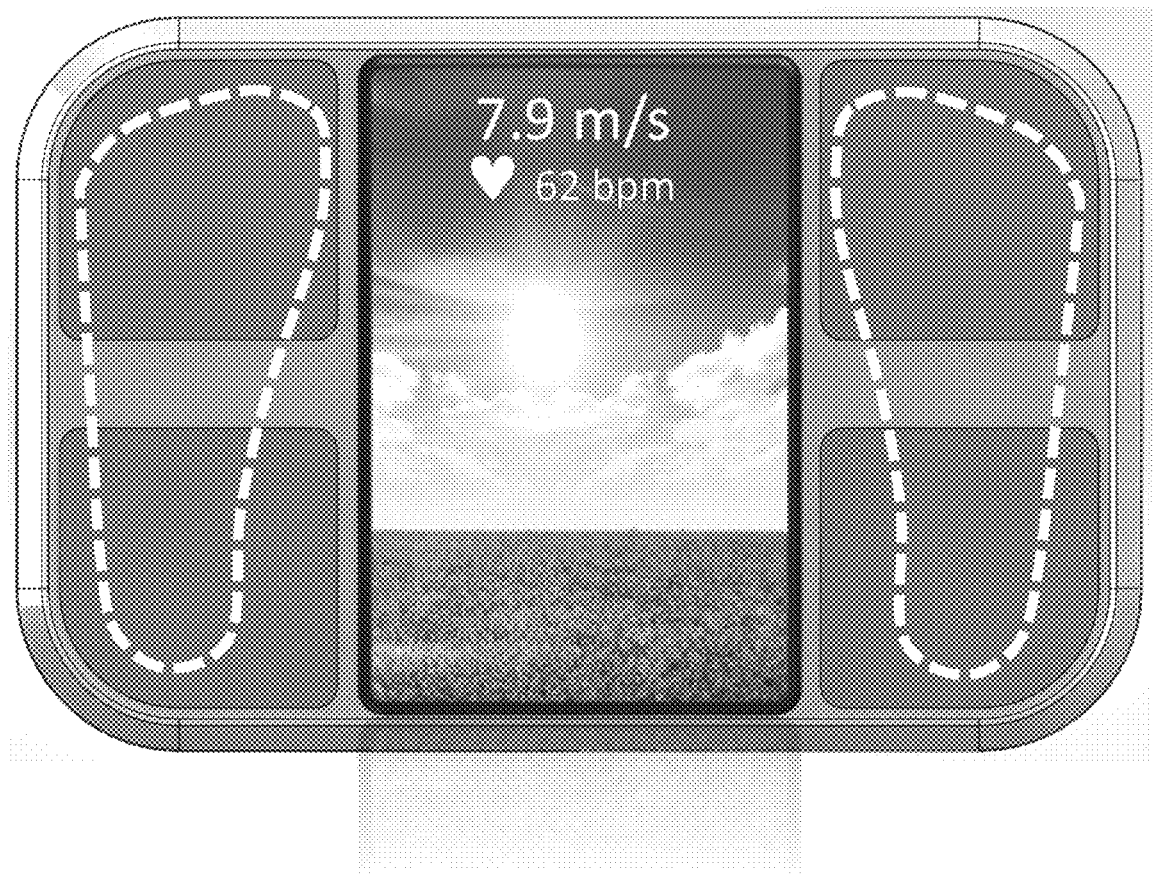
FIG. 1C shows an isometric view of a weighing scale with large-area display, consistent with various aspects of the present disclosure.

In certain specific embodiments of the present disclosure, as shown in FIG. 1C, a large-area display is implemented on the top surface of a scale, where the display is full length in one direction, but not full width. This display size is closer in dimensions to a tablet computing device (such as an iPad). The electrodes (for physiological and biometric sensing) are on the left and right sides of the display. As discussed above in reference to FIGS. 1B and 1n more detail below in reference to FIGS. 6A-D, the display is capable of presenting a myriad of information to the user.

In some embodiments, the apparatus illustrated by FIGS. 1A-1C can be used with a user wearable device. A user wearable device, such as a wearable wrist device, measures physiological data such as heart rate. An example of the wearable wrist device as shown herein is Gear Fit™, available from Samsung. Another example is the Garmin Forerunner 305™ which provides features including: a training assistant that provides athletes (and users) with precise speed, distance and pace data; training center software which allows users to download workout data for detailed analysis; applications for varying types of sports, such as cycling, cross country skiing, and windsurfing; motion-based mapping, GPS and route sharing capabilities as part of the data acquisition. Such wearable devices are useful for sharing heart-based data with the scale apparatus as shown in the Figures.

In some embodiments, the apparatus comprising a platform region, processor circuitry (such as a user-targeted circuitry), and a base unit. The apparatus includes a weighing scale. The base unit integrates the support structure and a display. The support structure includes the platform region and a plurality of forces sensors including sensor circuitry. The platform region is configured and arranged to support a user while the user stands on the platform region. Further, the platform region engages the user with the plurality of force sensors while the user stands on the platform region. The sensor circuitry collects analog signals (e.g., physiological data) from the user. The display is configured and arranged with the support structure for displaying data through the platform region.

The display is configured and arranged with processor circuitry to monitor cardiac physiological parameters while the user is standing on the platform region, and communicate the cardiac physiological parameters to the user. In a number of embodiments, the display configured and arranged with the processor circuitry assesses the fitness of the user based on one or more of the cardiac physiological parameters. Alternatively, an external device assesses the one or more cardiac physiological parameters (e.g., communicated to the external device) and communicates the assessed cardiac physiological parameters to the apparatus using a wireless or wired communication. In various embodiments, the physiological parameters of the user are measured when the user is in a resting state and an exertion state, as discussed further herein.

The apparatus, e.g., scale, has display capabilities, e.g., visual and/or sound, and the measurement devices shown in the Figures (e.g., FIG. 1D) communicate user physiological data wirelessly (and via the Cloud) to and from an external device (e.g., a portable remote devices such as a smart tablets and cell phones). For example, applications (e.g., apps) are provided on the external devices (e.g., smart phones, tablets, etc.) for customization of various user health goals, training regimes, health diagnostics and other modalities, responsive to the communicated user data.

In some embodiments, the apparatus tracks cardiac physiological parameters of the user over time. The apparatus includes interface circuitry driving the display. The interface circuitry is located on the apparatus and/or on an external device. The display outputs a signal indicative of the determined cardiac physiological parameters to the interface circuit. The interface circuit, responsive to the output signal, tracks cardiac physiological parameters of the user over time.

The tracking of cardiac physiological parameters is used to assess a fitness of the user. For example, the cardiac physiological parameters, tracked over time, are compared to prior-assessed user norms (e.g., prior cardiac physiological parameters of the user and/or average value of tracked cardiac physiological parameters) or other baselines/population norms (e.g., average values of a particular demographic population). Feedback to the user can include indications of a change in one or more recovery parameters, a deviation from prior-assessed user norms, other baseline/population norms, and a combination thereof.

Figure 1D:
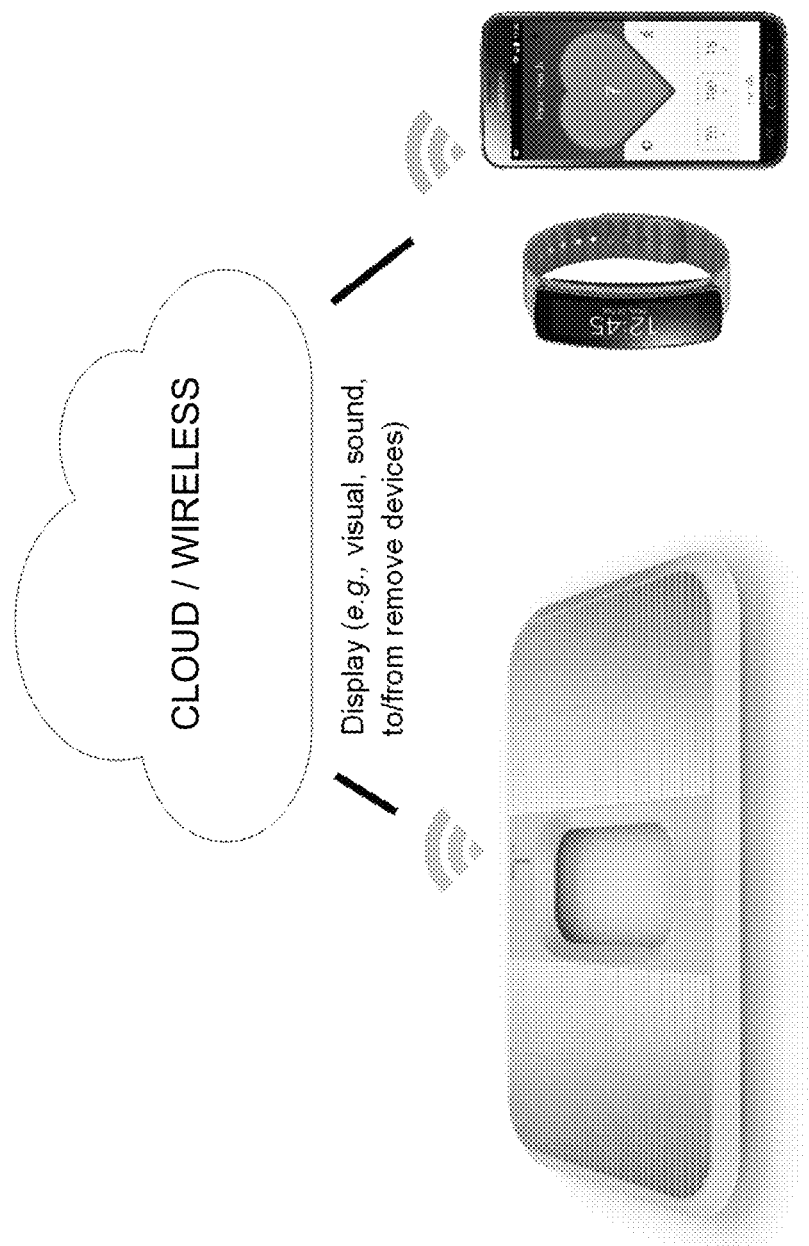
FIG. 1D shows a weighing scale communicating with an external device, consistent with various aspects of the present disclosure

As further illustrated by FIG. 1D, the apparatus, in some embodiments, is in communication with at least one other sensor. Such sensor can include an external device, such as a wrist wearable device, a cell phone, a tablet, etc. The apparatus uses data communicated from the at least one other sensor to monitor the one or more cardiac physiological parameters. For example, the data communicated is used to refine measurements made by the apparatus.

In many embodiments, the apparatus and/or external source compares a user's cardiac physiological parameters to a health metric. Some examples of health metrics include cardiac physiological parameters of an average individual of the same sex, age, height, weight, etc., or cardiac physiological parameters indicative of a level of fitness to which the user wishes to achieve (e.g., run a marathon, or climb Mount Everest). In one specific embodiment, user-targeted circuitry of the apparatus accesses current cardiac physiological parameters of the user and the health metric associated with at least one of a number of the user-specific cardiac physiological parameters that are stored in the data-access circuit (e.g., sex, age, height, and weight of the user). Current cardiac physiological parameters may, for example, be obtained by sensing physiological data of the user and assessing the cardiac physiological parameters of the user, as discussed in more detail below, or by accessing recent physiological parameters of the user that are stored in a data-access circuit. The user-targeted circuitry compares the current cardiac physiological parameters to the stored health metric to determine a fitness level of the user.

In many embodiments, the apparatus (e.g., a scale) determines (and displays) action(s) to encourage improvement of the fitness, after determining the fitness of the user. For example, where a user's determined cardiac physiological parameters are indicative of a lack of cardiovascular fitness, the apparatus suggests that the user add a one mile jog into his or her daily fitness routine. In many embodiments, the user-targeted circuitry transmits (via the data-access circuit) to an external device (e.g., personal electronic device) associated with the user, the cardiac physiological parameters, physiological data, recommended physical regimens, and/or other data indicative of the physical health of the user. In some embodiments, the external device stores such data and/or further analyzes the data in view of other stored data such as data indicative of diet and caloric intake of the user or the current physical regimen of the user. The external device instructs the user to adjust his or her diet and/or physical regimen accordingly. In further embodiments, the external device transmits stored data indicative of the diet and caloric intake of the user, the current physical regimen of the user, or other health related data. The user-targeted circuitry considers such data when determining the physiological parameters of the user to further improve the accuracy of such determined physiological parameters.

Support glass above a display transmits the weight of a user to a bezel along the perimeter of the scale (away from the display), while also transmitting touch-capacitive signals indicative of a user's position and/or movement on the support glass, through the display to scale circuitry. A support frame is attached to the bezel and supports the display within the bezel. The bezel support frame houses load cells equally spaced along the perimeter of the scale. Each load cell outputs an electrical signal indicative of a mass transmitted from the user through the load cell to the scale circuitry (which interprets the electrical signals and presents the weight of the user on the display). A plurality of translucent electrode leads are embedded into the support glass to provide electrical signals to the scale circuitry, and the electrical signals are interpreted by the scale circuitry as being indicative of a condition of a user, with the condition being presented on the display for the user.

Load bearing characteristics of the scale provides both functionality and longevity. The support glass, in conjunction with the bezel and support frame, minimizes the load transfer to the display while still maintaining sufficient conductivity through the support glass to the display to allow for touch-screen functionality. If the support glass is too compliant, under the user's weight, excessive force exerted on the display may cause damage. If the glass is not conductively coupled to the display (e.g., due to a gap there-between), touch-screen functionality of the scale may be challenging or inapplicable. Accordingly, one or more embodiments address such issues with a support frame for a display that allows for minimal compliance, by which the display remains conductively coupled to the support glass while preventing excessive force from being exerted on the display (that would otherwise cause damage).

The apparatus, in various embodiments and as previously discussed, can include a scale and/or methods of using a scale. An example version of a scale is provided by U.S. Pat. No. 8,870,780, and by U.S. Pat. No. 9,011,346, each of which is fully incorporated herein by reference and specifically incorporated with regard to an apparatus that captures a BCG signal while a user stands on the apparatus. Another example version of a scale is provided in U.S. patent application Ser. No. 14/338,266 filed on Jul. 22, 2014, and entitled "Device and Method having Automatic User-Responsive and User-Specific Physiological-Meter Platform." The Appendix, as attached hereto and included as part of the instant patent application, is adapted from this latter patent document (U.S. Ser. No. 14/338,266). This Appendix is also fully incorporated herein by reference for its general teaching and specifically incorporated with regard to an apparatus including impedance-measurement circuitry to determine pulse characteristics and a display which can be oriented based on and/or in response to where the user locates his/her feet on the scale platform as well as other embodiments discussed therein and involving use of the display.

Figure 2C:
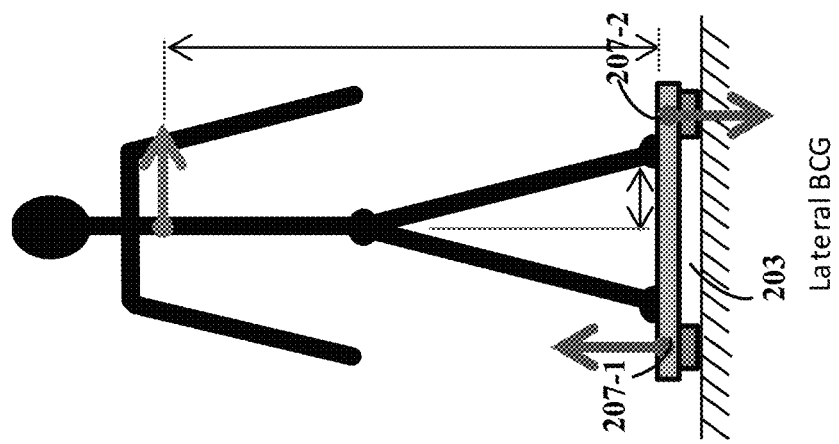
FIG. 2A-2C show an apparatus used to obtain analog signals using force sensors, consistent with various aspects of the present disclosure.
Figure 2B:
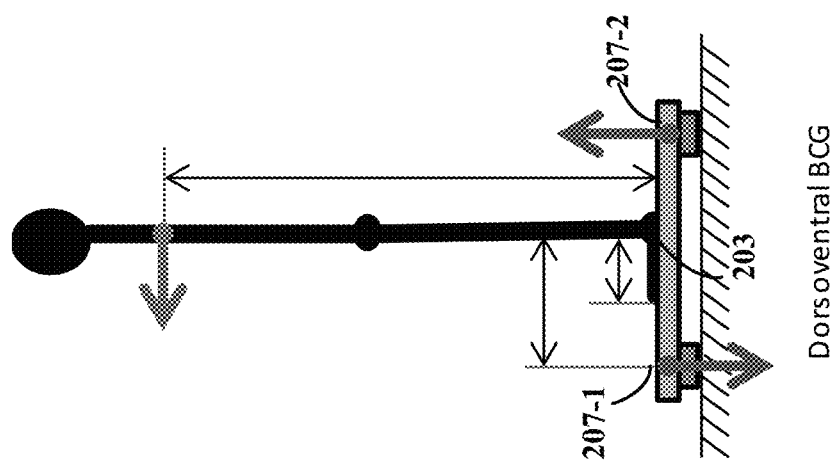
Figure 2A:
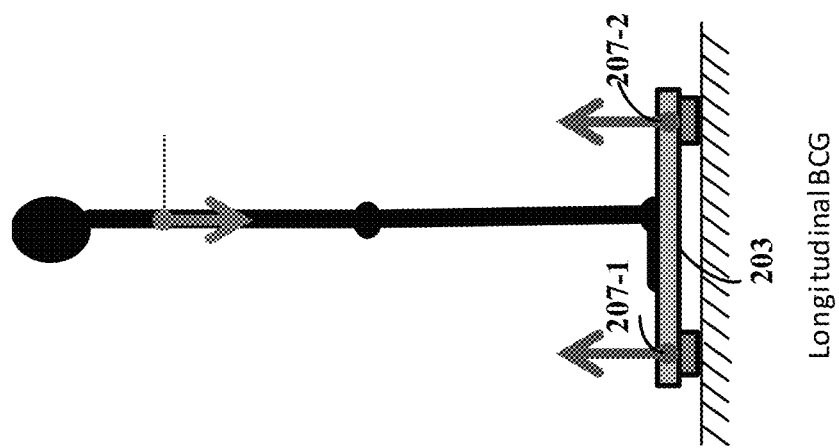

FIG. 2A-2C show an apparatus used to obtain analog signals using force sensors, consistent with various aspects of the present disclosure. As illustrated by FIG. 2A-2C, the force sensors 207-1, 207-2 are located in the corners of the platform region 203 of the apparatus, although the embodiments are not so limited and can include, for example, force sensors located in the center of the platform region 203. The analog signals can be indicative of balance movement (e.g., tilt and lean movement/postural sway) of the user. Using the analog signals, processor circuitry can detect movement of the user while the user is standing on the platform region 203 and/or determine cardiac physiological parameters of the user using the detected movement and the analog signals. For example, using the analog signals (e.g., balance signals) the processor circuitry determines an estimation of forces in three directions from the platform region 203 of the apparatus.

In various embodiments, the cardiac physiological parameter is a BCG parameter. A BCG parameter is mostly generated in the torso of the user. Transfer of the BCG parameter to the apparatus is supported by the legs and the feet of the user. For example, in a lateral direction (e.g., as illustrated by FIG. 2C), the horizontal force at the torso is coupled to the apparatus by the lever defined by the legs and the separation between the feet (e.g., stance). In the dorsoventral direction (e.g., as illustrated by FIG. 2B), the horizontal force is coupled through the leg and the length of the feet. As the transfer of the torso BCG forces depends on the relative geometric factors, as well as mechanical properties of joints and body, the cardiac physiological parameters determined by the processor circuitry may not be an exact representation of the actual BCG parameter of the user. Geometric aspects (e.g., lever effect) may attenuate or amplify the signals. Stiffness of joints can also impact the amplitude, and contribute to distortion. However, the cardiac physiological signals indicative of the cardiac physiological parameter in the three directions remain orthogonal, as little cross-coupling between lateral and dorsoventral axis exists.

FIG. 2A illustrates determining a cardiac physiological signal indicative of a cardiac physiological parameter in a longitudinal direction. A cardiac physiological signal indicative of a cardiac physiological parameter in a longitudinal direction is herein generally referred to as a longitudinal cardiac physiological signal for ease of reference. As illustrated, the longitudinal cardiac physiological signal is transmitted to all of the force sensors 207-1, 207-2.

A processor circuitry determines the longitudinal cardiac physiological signal using analog signals from each of the force sensors. For example, the longitudinal cardiac physiological signal can be extracted, by the processor circuitry, by filtering the analog signals from the force sensors 207-1, 207-2 using a low-pass filter (e.g., 15-30 Hertz (Hz) low-pass filter, in various embodiments also including a 25 Hz low-pass filter) to reduce noise (e.g., high frequency noise).

In various embodiments, the analog signals can be affected by postural sway of the user. For example, at least some of the effect on the analog signals can be mitigated that is attributable to the postural sway of the user while the user stands on the platform region. In some embodiments, the postural sway may not affect and/or correspond to the longitudinal cardiac analog signal. However, in various embodiments, the effect on the analog signals can correspond to the longitudinal cardiac physiological signal, as well as a lateral cardiac physiological signal and a dorsoventral cardiac physiological signal, as discussed further herein and as illustrated by FIGS. 2B and 2C. For example, as may be appreciated, the user may not be standing facing forward (as illustrated by FIG. 2A). To mitigate at least some effect on the analog signals attributable to postural sway of the user, the processor circuitry can estimate and/or remove a baseline wander from the analog signals, as described further herein. Further, the processor circuitry can generate data indicative of the cardiac physiological signals based on said processing of the analog signals and the mitigation of at least some of the effect. The generated data can include, for example, one of a longitudinal cardiac physiological signal, a lateral cardiac physiological signal, and a dorsoventral cardiac physiological signal, and a combination thereof.

FIG. 2B illustrates determining a cardiac physiological signal indicative of a cardiac physiological parameter in a dorsoventral direction. A cardiac physiological signal indicative of a cardiac physiological parameter in a dorsoventral direction is herein generally referred to as a dorsoventral cardiac physiological signal for ease of reference. As illustrated, the dorsoventral cardiac physiological signal is transmitted as a differential force between the force sensors proximal to the toes of the user (e.g., force sensor 207-1) and the force sensors proximal to the heels of the user (e.g., force sensor 207-2) and is transduced through a lever that the body and feet represent.

The processor circuitry determines the dorsoventral cardiac physiological signal by comparing analog signals from force sensors proximal to the toes to analog signals from force sensors proximal to the heels of the user. For example, the dorsoventral cardiac physiological signal can be extracted, by the processor circuitry, by filtering the analog signals from the relevant force sensors by using a low-pass filter to reduce noise and by removing the sway movement. The sway movement can be removed, after the low-pass filter, in various embodiments, by estimating a baseline wander using Savitsky-Golay filter with a $4^{th}$ order polynomial and a frame a period of time (e.g., 1 second resulting in 1001 samples at 1 ksps). The estimated baseline wander is subtracted from the filtered analog signals provided by the relevant force sensors to extract the dorsoventral cardiac physiological signal.

FIG. 2C illustrates determining a cardiac physiological signal indicative of a cardiac physiological parameter in a lateral direction. A cardiac physiological signal indicative of a cardiac physiological parameter in a lateral direction is herein generally referred to as a lateral cardiac physiological signal for ease of reference. As illustrated, the lateral cardiac physiological signal is transmitted as a differential force between the force sensors proximal to a first side (e.g., left side) of the user (e.g., force sensor 207-1) and the force sensors proximal to a second side (e.g., right side) of the user (e.g., force sensor 207-2) and is transduced through a lever that the body and separation between the feet represent.

The processor circuitry determines the lateral cardiac physiological signal by comparing analog signals from force sensors proximal to the first side of the user to analog signals from force sensors proximal to the second side of the user. For example, the lateral cardiac physiological signal can be extracted, by the processor circuitry, by filtering the analog signals from the relevant force sensors by using a low-pass filter to reduce noise and by removing the sway movement. The sway movement can be removed, after the low-pass filter, in various embodiments, by estimating a baseline wander using Savitsky-Golay filter with a $4^{th}$ order polynomial and a frame a period of time (e.g., 1 second resulting in 1001 samples at 1 kilosample per second (ksps)). The estimated baseline wander is subtracted from the filtered analog signals (e.g., low-pass filtered) provided by the relevant force sensors to extract the lateral cardiac physiological signal.

The ability to extract the cardiac physiological signals indicative of a cardiac physiological parameter in multiple directions, as illustrated by FIG. 2A-2C, allows for a number of further determinations related to the physiological health of the user. The extracted cardiac physiological signals can be used to determine a cardiac physiological parameter of the user that is two-dimensional (2D) or three-dimensional (3D). For example, a 2D cardiac physiological parameter can be determined using a subset of the cardiac physiological signals, such as using the longitudinal cardiac physiological signal and one of the dorsoventral cardiac physiological signal and the lateral cardiac physiological signal or using the lateral and dorsoventral cardiac physiological signals. The 2D cardiac physiological parameter can beneficial in instances of noisey cardiac physiological signals or weak cardiac physiological signals indicative of the cardiac physiological parameter in a particular direction. Additionally and/or alternatively, a 3D cardiac physiological parameter can be determined using the longitudinal, dorsoventral, and lateral cardiac physiological signals.

For example, in various embodiments, the relevant cardiac physiological signals can be fused (e.g., summed, multiplied, adaptive filtered, and principal component analyzed) to form a 2D signal represented by the longitudinal and one of the dorsoventral and lateral cardiac physiological signals and/or to form a 3D signal represented by the longitudinal, dorsoventral, and lateral cardiac physiological signals. As an example, for a BCG parameter, a timing of the ejection of the blood can be extracted using a 2D signal or a 3D signal. In some embodiments, the J wave can be located in the longitudinal cardiac physiological signal and then the local minima preceding the J wave can be located in the 2D or 3D signal (accounting for sign). Alternatively, the I wave can be located as a local maxima preceding the J wave in the 2D or 3D signal, which can be determined as the square root of the 2D or 3D signal (e.g., the summed signal). Alternatively, in some embodiments, the I wave can be located as a local maxima preceding the J wave in a torsion or curvature of a curve built from the longitudinal, lateral, and dorsoventral cardiac physiological signals. The torsion and curve can be determined using Frenet-Serret formulations. Further, the 2D or 3D signal (e.g., the magnitude signal) can be used to derive other parameters, such as an estimate of cardiac output.

In various embodiments, a respiration rate of the user and phase can be monitored based on rotation of a BCG parameter/force that is indicative of movement of the heart (and/or rotation of left ventricular aortic tract) during the respiration cycle. Further, upper body posture monitoring can be performed based on rotation of the BCG parameter/force indicative of an angle and orientation of the chest of the user while standing on the apparatus. In some embodiments, the cardiac physiological signals indicative of a cardiac physiological parameter in the multiple directions can be fused (e.g., addition, multiplication, adaptive filtering, and principal component analysis). Due to the orthogonal and synchronous (e.g., correlated) nature of the parameters, fusing the cardiac physiological signals indicative of a cardiac physiological parameter in the multipole directions reinforces the cardiac physiological parameter to improve signal-to-noise and detection. Further, position-independent BCG features can be determined using the apparatus (e.g., scale), such as by using the Frenet-Serret space curve invariants. Such features can include timings, intervals, amplitudes, and rate changes. Although the preceding examples discuss use of the cardiac physiological signals in all of the multiple (e.g., three) directions, embodiments in accordance with the present disclosure are not so limited. For example, various determination can use cardiac physiological signals indicative of a cardiac physiological parameter in two directions, instead of three.

For example, the cardiac physiological parameter can be a 3D curve, such as a 3D curve of a BCG parameter of the user. Another parameter indicative of at least one of respiration and posture of the user, in various embodiments, can be extracted from the 3D curve over a period of time. A parameter indicative of respiration (e.g., a respiration rate) can be extracted from the axis of an ellipsoid defined by the 3D curve (over whole or part of the cardiac cycle). For example, rocking of the axis of the ellipsoid over portions (e.g., 5-10 second) of a period of time can be indicative of the respiration (e.g., as the main direction of blood ejection is twisted when the lungs fill and push the heart on the side). A parameter indicative of posture can be extracted from the axis of the ellipsoid based on the average direction of the axis over multiple respiration cycles. Posture information can be beneficial, in some instances, to verify the user is standing all the way on the scale.

Various other techniques can be used to determine the cardiac physiological parameters which can be model-based and/or via calibrations. For example, a BCG force can be estimated using the detected movements and a geometrical model. In such embodiments, the lengths of the user's torso, legs, and feet are provided to the apparatus (such as, using user input and/or from another apparatus). Based on the specific lengths of the user (torso, legs, feet), the processor circuitry calculates, from the analog signals (e.g., balance forces measured by the scale) obtained by the force sensors, the amplitude of the force of the BCG signal at the torso. That is, an amplitude of force of the 3D cardiac physiological parameter (e.g., 3D BCG parameter) can be determined using input data (e.g., torso length, leg length and foot length) and the cardiac physiological signals indicative of a cardiac physiological parameter in the longitudinal, lateral, and dorsoventral directions. Due to the lever effect of the leg/feet, differential (side-to-side/front-to-back) forces measured by the apparatus, in some embodiments, are larger than the BCG forces. First order estimation can rely (solely) on lengths, assuming stiff joints and torso. A generalized model of the musculoskeletal system can improve the reconstruction by modeling, more realistically, the stiffness and also considering the mass put in motion along the way.

In some embodiments, a generalized model of the transfer of force from the torso to the feet may not be accurate enough or may not be available. In such instances, a secondary sensor, such as an accelerometer, can be placed on the torso of the user. The secondary sensor measures cardiac physiological parameters of the user and/or communicates, using communication circuitry, the cardiac physiological parameters to the processor circuitry of the apparatus. The processor circuitry de-noises the cardiac physiological signal indicative of a cardiac physiological parameter in the multiple directions using the cardiac physiological parameters measured using the secondary sensor. For example, using the secondary sensor, the apparatus estimates a 3D force (which is proportional to acceleration) and extracts a transfer function between each projection of the force at the torso and the differential force obtained by the force sensors of the apparatus for each of the lateral and dorsoventral cardiac physiological signals. This can also be performed for the longitudinal cardiac physiological signal, in some embodiments.

In various embodiments, the secondary sensor is placed on the upper torso and the local seismocardiogram (SCG) component is removed. This can be achieved by low-pass filtering, typically between 15-25 Hertz (Hz). Alternatively, the secondary sensor is placed at a location minimizing the SCG component (e.g., over the spine). Similarly, any location that may be prone to local acceleration from the heart beat (such as over the pulmonary artery) can be avoided. The secondary sensor can be a dedicated device, or any device using a sensitive accelerometer (activity tracker, phone).

Figure 3:
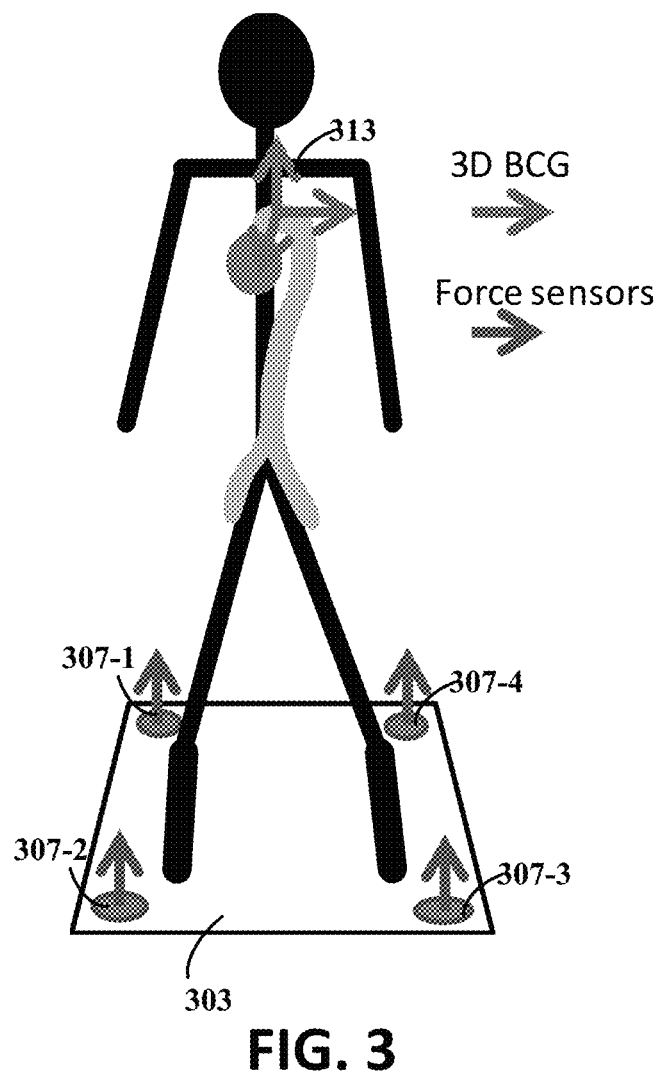
FIG. 3 shows an apparatus used to obtain analog signals for determining a three-dimensional cardiac physiological parameter, consistent with various aspects of the present disclosure.

FIG. 3 shows an apparatus including force sensors 307-1, 307-2, 307-3, 307-4 used to provide analog signals for determining a 3D cardiac physiological parameter 313, consistent with various aspects of the present disclosure. As illustrated by FIG. 3, the 3D cardiac physiological parameter 313, in some embodiments, includes a 3D vector that is formed using the generated data indicative of the cardiac physiological parameters. For example, the generated data can include the cardiac physiological signal indicative of a cardiac physiological parameter in the longitudinal, lateral, and dorsoventral directions. That is, the 3D cardiac physiological parameter 313 can be determined using a combination of the longitudinal, lateral, and dorsoventral cardiac physiological signals.

In various embodiments, the 3D cardiac physiological parameter 313 is analyzed/determined using a variety of modalities. Example modalities to analyze/determine the 3D cardiac physiological parameter can include a sum of all axes, a magnitude of 3D vector, and Frenet-Serret space curve invariants (also known as a subset of the Caftan invariants) performed on the cardiac physiological parameters in the multiple directions.

FIG. 4 shows a graph 417 illustrating a longitudinal cardiac physiological signal, a lateral cardiac physiological signal and a dorsoventral cardiac physiological signal, and also a second graph 419 illustrating a 3D cardiac physiological parameter, consistent with various aspects of the present disclosure.

To determine the cardiac physiological signals, indicative of a cardiac physiological parameters, from the analog signals (e.g., balance signals) provided by the force sensors, in various embodiments, a baseline wander removal is performed using the processor circuitry. The baseline wander removal can include a high-pass filtering, a Savitzky-Golay filtering, a wavelet filter, and/or a quadratic spline, among other techniques.

The graph 419 illustrates the 3D cardiac physiological parameter as a 3D curve. The 3D curve, as previously discussed, can be determined using a combination of the longitudinal, lateral, and dorsoventral cardiac physiological signals. Although FIG. 4 illustrates the 3D cardiac physiological parameter represented as a 3D curve, the embodiments are not so limited. For example, the 3D cardiac physiological parameter can be presented as the combination of the three cardiac physiological parameters in a two-dimensional representation. In some embodiments, the 3D curve can be displayed on a display of the scale and/or another apparatus.

Figure 5:
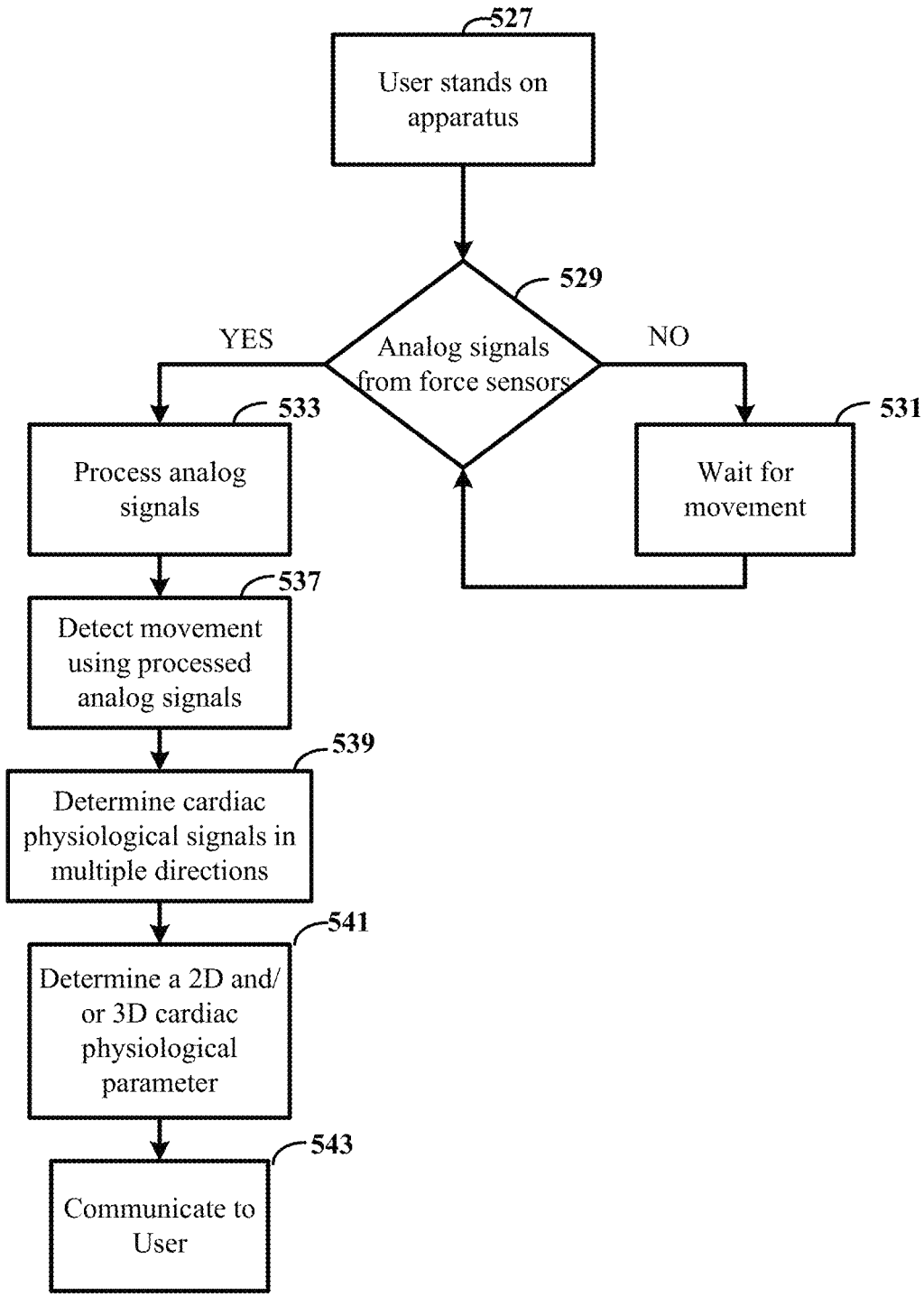
FIG. 5 is a flow chart illustrating an example manner in which cardiac physiological parameters are determined consistent with various aspects of the present disclosure.

FIG. 5 is a flow chart illustrating an example manner in which cardiac physiological parameters are determined consistent with various aspects of the present disclosure. The cardiac physiological parameters can be detected using cardiac physiological signals indicative of the cardiac physiological parameter in multiple directions.

For example, at block 527, a user stands on an apparatus. The apparatus can include an apparatus as illustrated by FIGS. 1A-1D and as described herein. At block 529, a determination is made whether analog signals from the force sensors are received by processor circuitry. In response to not receiving analog signals, at block 531, the process includes waiting for movement.

In response to receiving analog signals, at block 533, the processor circuitry processes the analog signals, and, at block 537, detects movement using the processed analog signals. The movement can include postural sway. As previously discussed, postural sway can include tilt and lean movement relative to a nominal-still position of the user, while the user is standing on the platform region of the apparatus. At block 539, the processor circuitry determines cardiac physiological signals indicative of a cardiac physiological parameter of the user in multiple directions. The multiple directions can include a longitudinal, lateral, and/or a dorsoventral direction, as previously discussed. At block 541, the processor circuitry determines a 2D and/or a 3D cardiac physiological parameter using the cardiac physiological parameters.

In accordance with various embodiments, at block 543, the cardiac physiological parameters is communicated to the user. The communicated parameters can include a 2D cardiac physiological parameter and/or a 3D cardiac physiological parameter, among other parameters and/or signals. In some embodiments, the apparatus can include a display to communicate the data to the user. Alternatively and/or in addition, the apparatus can include communication circuitry configured to communicate with an external device. For example, the apparatus can communicate the cardiac physiological parameters to the external device and the external device can display the data to the user.

The various embodiments illustrated and discussed in connection with FIG. 1A-5 can be used in combination with the embodiments illustrated by FIG. 6A-21C.

Figure 6A:
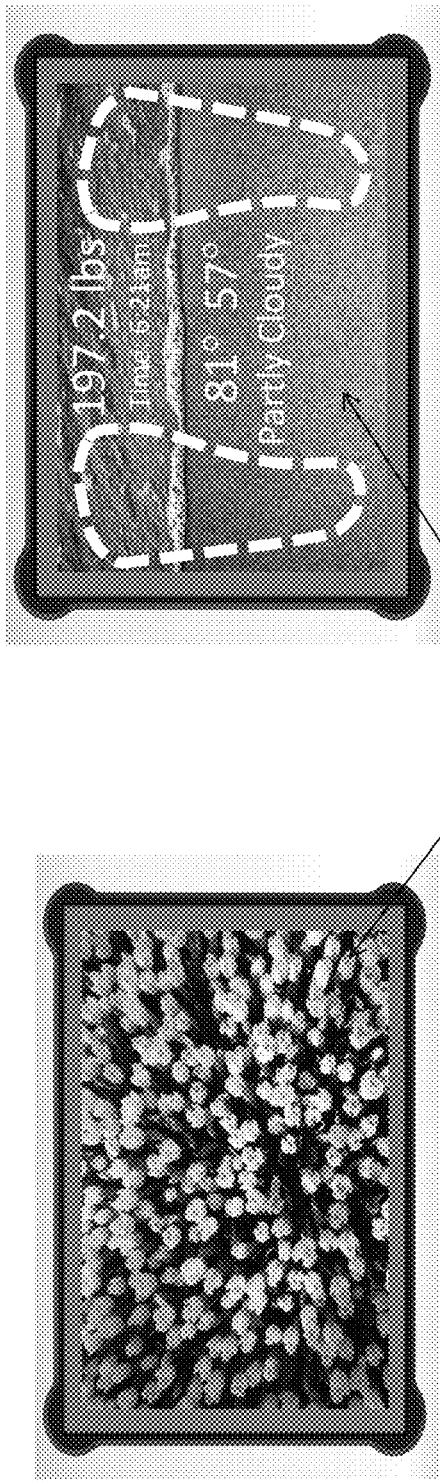
FIGS. 6A-D show top views of a number of weighing scale displays, consistent with various aspects of the present disclosure.

FIG. 6A-D shows top views of a number of scale displays, consistent with various aspects of the present disclosure. FIG. 6A presents an exemplary image that is selected by a user as a "screen saver," and displayed by the scale when not in use. In further embodiments, the scale, when not in use, presents a slide-show of images selected by the user, such as family-photos. In more specific embodiments of the present disclosure, a camera is communicatively coupled to the scale and operates with facial recognition software for identifying the user. Based on the identified user, the scale operates in accordance with user-specific aspects as relate to physiology or preferences such as for a "screen saver." For instance, biometric and physiological tests are conducted, with the test results saved to the identified user's file (and/or the results sent to a user's doctor for further review and analysis), as well as a number of other functionalities, such as playing the user's favorite musical artist and the pertinent information is loaded to the display to present the user with the pertinent information.

Figure 6B:
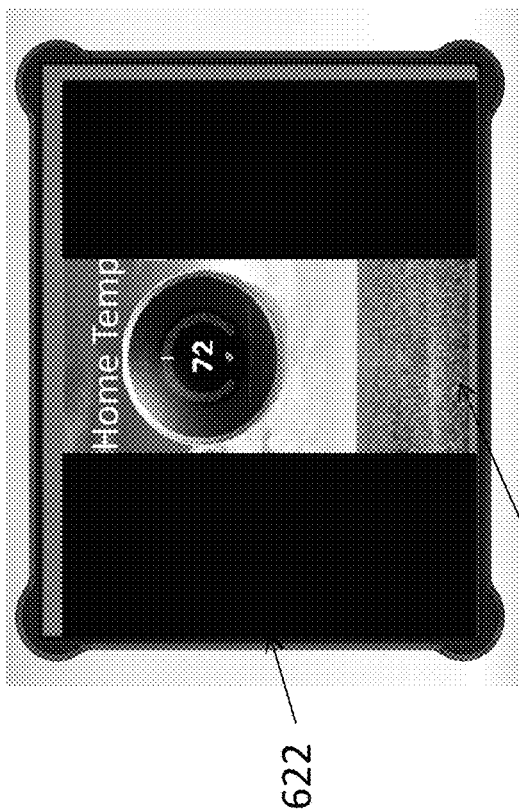
Figure 6C:
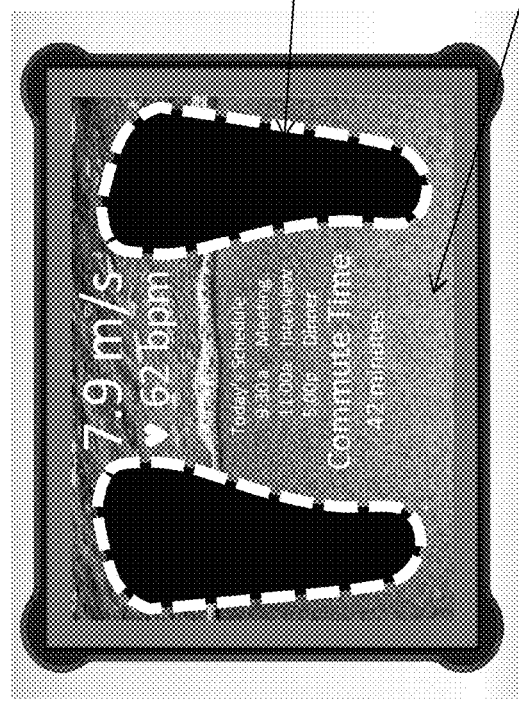
Figure 6D:
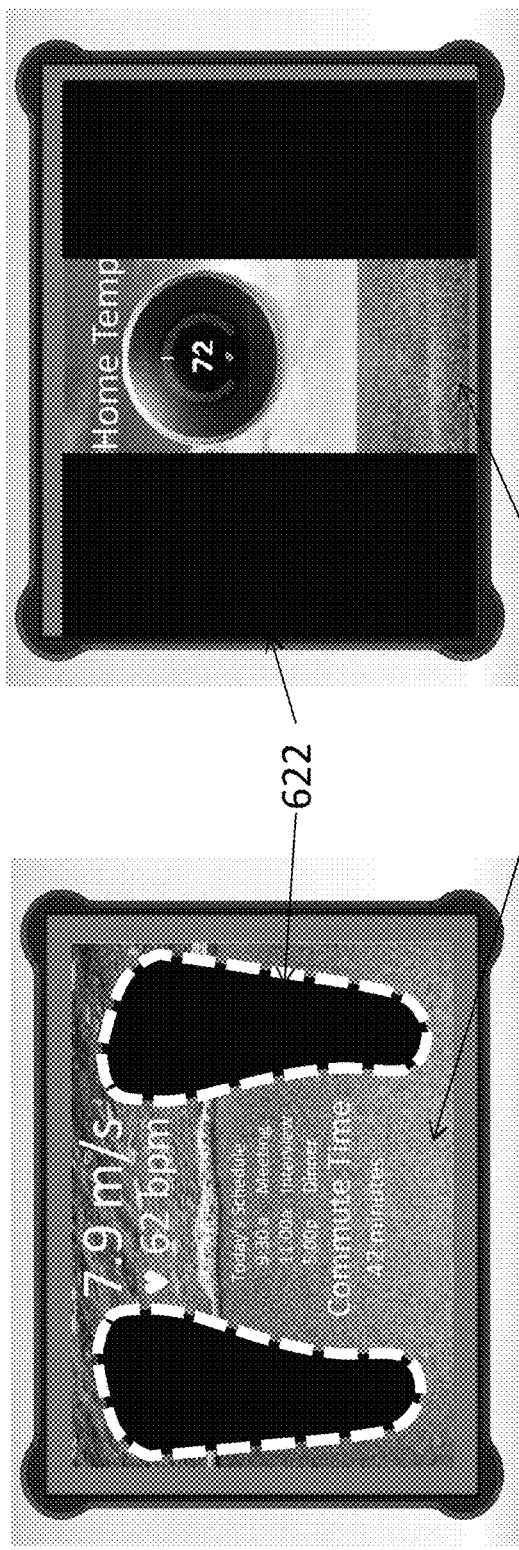

As shown in FIG. 6B, a relaxing ambience is provided to the room where the scale is located, such as by displaying a video of waves lapping over sand. In some embodiments, the scale plays an audio track associated with the video. In FIGS. 6B-D, while the scale conducts tests on the user (e.g., weight measurements, biometric and physiological tests) at a time programmable by the user, and/or other times, the user is able to access other information from the scale such as the user's current weight, pulse rate, and time of day, among other user-configurable information. In further more specific embodiments (as shown in FIGS. 6B-D), the scale displays weather conditions, home climate, commute times, user's daily schedule, personal reminders, or other information as is collected by the scale via a wired and/or wireless connection to the internet, or to a smart device (e.g., a hand-held mobile phone). As shown in FIG. 6D, in implementations of the disclosure directed to smart-homes, a scale user controls (via the touch-screen display) a plurality of other devices throughout the home such as a climate control system, security system, operation of the shower, etc. The electronic communications between the scale and the various devices includes a wireless and/or wired communications.

FIG. 7 shows a scale 700 with large-area display (e.g., for a bathroom), consistent with various aspects of the present disclosure. In the present embodiment, the scale 700 includes circuitry, such as a camera and image processing circuitry. The camera may be directed at the floor below the scale, flush with the top of the scale, or the surrounding area. Based on the images processed (by the image processing circuitry) of the area surrounding the scale, the scale's large-area display depicts an image that mimics the surrounding area when idle. In embodiments where the camera is directed at the surrounding floor, the scale depicts an image indicative of the flooring below the scale or flush with the top of the scale, which minimizes detraction of aesthetics of the scale. In either embodiment discussed above, when the scale is idle, from a glance the scale is effectively camouflaged. In other embodiments, the user and/or another person, such as an interior designer, selects a theme for the display based on the desired look for the room where the scale is placed.

Figure 8A:
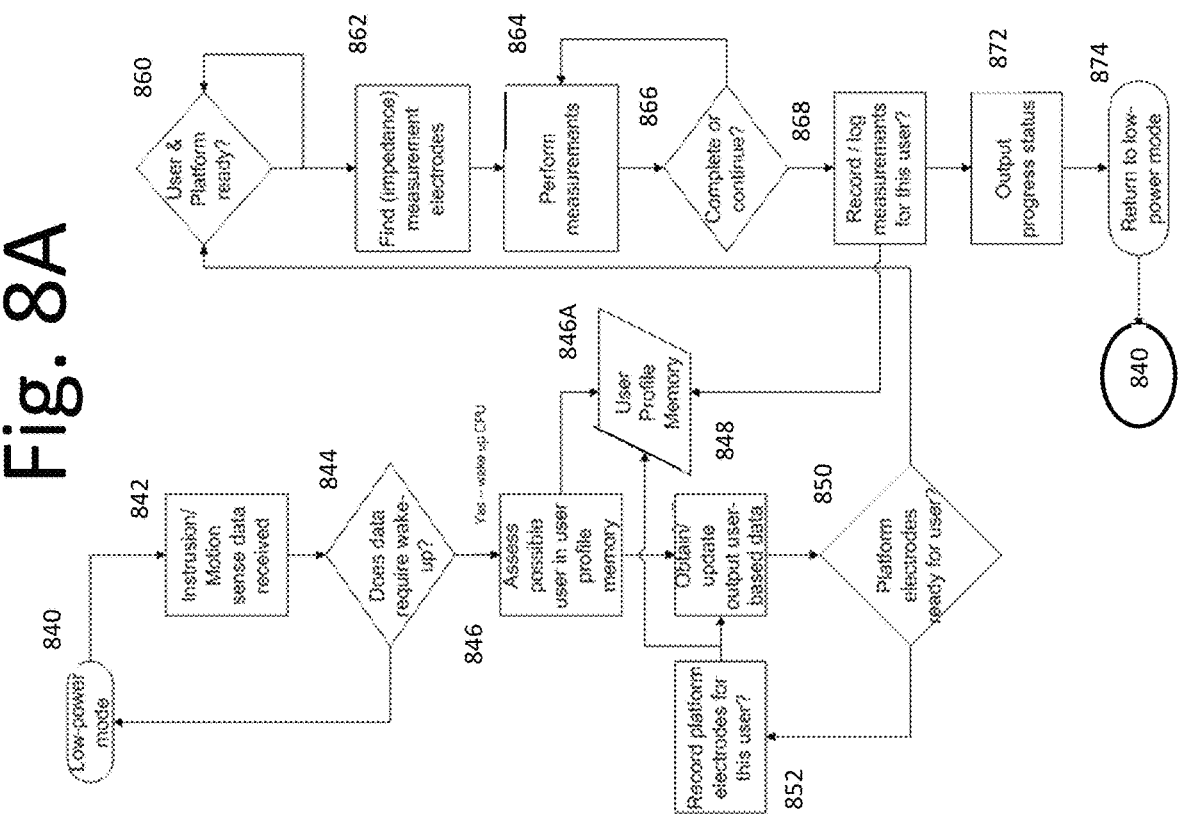
FIG. 8A is a flow chart illustrating an example manner in which a user-specific physiologic meter/scale is programmed to provide features consistent with aspects of the present disclosure.

FIG. 8A is a flow chart depicting an example manner in which a user specific physiologic meter or scale is programmed in accordance with the present disclosure. This flowchart uses a computer processor circuit (or CPU) along with a memory circuit shown herein as user profile memory 846A. The user profile memory is automatically updated by the CPU to coincide with the user's health progress/performance, age, weight, various cardiovascular criteria (e.g., as measured by the PVW), and/or other related conditions. The CPU operates in a low-power consumption mode, which may be in off mode or a low-power sleep mode, and at least one other higher power consumption mode of operation. As exemplary circuits for transitioning between such a low-power and higher power modes, the CPU is integrated with presence and/or motion sense circuits, such as a passive infrared (PIR) circuit and/or gyro PIR circuit. In a typical application, the PIR circuit provides a constant flow of data indicative of amounts of radiation (e.g., body heat or bio thermal) sensed in a field of view directed by the PIR circuit. For instance, the PIR circuit can be installed behind a transparent upper surface of the platform (such as through the display screen of the platform apparatus) and installed at an angle so that the motion of the user, as the user approaches the platform apparatus, is sensed. Radiation from the user, upon reaching a certain detectable level, wakes up the CPU which then transitions from the low-power mode, as depicted in block 840, to a regular mode of operation. In alternative embodiments, the CPU transitions from the low-power mode of operation in response to another remote/wireless input used as an intrusion to awaken the CPU. In other embodiments, motion can be sensed with a single integrated microphone or microphone array, to detect the sounds of a user approaching, or user motion is detected by an accelerometer integrated in the scale.

Accordingly, from block 840, flow proceeds to block 842 where the user or other presence is sensed as data is received at the platform apparatus. At block 844, the circuitry assesses whether the received data qualifies as requiring a wake up. If not, flow turns to block 840. If however, wake up is required, flow proceeds from block 844 to block 846 where the CPU assesses whether a possible previous user has approached the platform apparatus. This assessment is performed by the CPU accessing the user profile memory 846A and comparing data stored therein for one or more such previous users with criteria corresponding to the received data that caused the wake up. Such criteria includes, for example, the time of the day (early morning or late morning), the pace at which the user approached the platform apparatus as sensed by the motion detection circuitry, the height of the user as indicated by the motion sensing circuitry and/or a camera installed and integrated with the CPU, and/or more sophisticated bio-metric data provided by the user and/or automatically by the circuitry in the platform apparatus.

As discussed herein, in various embodiments, such circuitry includes one or more of the following user-specific attributes: foot length, type of foot arch, weight of user, manner and speed at which the user steps onto the platform apparatus, and/or sounds made by the user's motion or by speech. As is also conventional, facial or body-feature recognition is used in connection with the camera and comparisons of images therefrom to images in the user profile memory.

From block 846, flow proceeds to block 848 where the CPU obtains and/or updates user corresponding data in the user profile memory. As a learning program is developed in the user profile memory, each access and use of the platform apparatus is used to expand on the data and profile for each such user. From block 848, flow proceeds to block 850 where a decision is made regarding whether the set of electrodes at the upper surface of the platform is ready for the user, which, in some embodiments, is based on the data obtained from the user profile memory. For example, delays may ensue from the user moving his or her feet about the upper surface of the platform apparatus, as may occur while certain data is being retrieved by the CPU (whether internally or from an external source such as a program or configuration data updates from the Internet cloud) or when the user steps over a certain area configured for providing display information back to the user. If the electrodes are not ready for the user, flow proceeds from block 850 to block 852 to accommodate this delay.

Once the CPU determines that the electrodes are ready for use while the user is standing on the platform surface, flow proceeds to block 860. Stabilization of the user on the platform surface may be ascertained by injecting current through the electrodes via the interleaved arrangement thereof. Where such current is returned via other electrodes for a particular foot and/or foot size, and is consistent for a relatively brief period of time (e.g., a few seconds), the CPU assumes that the user is standing still and ready to use the electrodes and related circuitry.

At block 860, a decision is made that both the user and the platform apparatus are ready for measuring impedance/analog signals and certain segments of the user's body, including at least one foot.

The remaining flow of FIG. 8A includes the application and sensing of current through the electrodes for finding the optimal electrodes (862) and for performing impedance measurements (block 864). These measurements are continued until completed at block 866 and the measurements are recorded and are logged in the user profile memory for this specific user, at block 868. At block 872, the CPU generates output data to provide feedback as to the completion of the measurements. The feedback, in some embodiments, is indicated as a request via the user profile for this user, as an overall report on the progress for the user relative to previous measurements made for this user and that are stored in the user profile memory. In such embodiments, the feedback is shown on the display, through a speaker with co-located apertures in the platform's housing for audible reception by the user, and/or by vibration circuitry which, upon vibration under control of the CPU, the user can sense through one or both feet while standing on the scale. From this output at block 872, flow returns to the low-power mode as indicated at block 874 with the return to the beginning of the flow at block 840.

Although not illustrated by FIG. 8A, the flow, in various embodiments, includes determining cardiac physiological parameters using cardiac physiological signals in multiple directions. For example, as previously discussed, movement of the user can be detected using force sensors located within the platform region of the scale. The movement and analog signals can be used to extract cardiac physiological signals indicative of a cardiac physiological parameter and to determine the cardiac physiological parameters using the cardiac physiological signals. In some embodiments, the cardiac physiological signals indicative of a cardiac physiological parameter are used to determine a 2D and/or a 3D cardiac physiological parameter of the user.

FIG. 8B shows current paths 800 through the body of a user 805 standing on a scale 810 for the IPG trigger pulse and Foot IPG, consistent with various aspects of the present disclosure. Impedance measurements 815 are measured when the user 805 is standing and wearing clothing articles over the feet such as socks or shoes, within the practical limitations of capacitive-based impedance sensing, with energy limits considered safe for human use. The measurements 815 can also be made with non-clothing material placed between the user's bare feet and contact electrodes, such as thin films or sheets of plastic, glass, paper or wax paper, whereby the electrodes operate within energy limits considered safe for human use. The IPG measurements are also sensed in the presence of callouses on the user's feet that normally diminish the quality of the signal.

As shown in FIG. 8B, the user 805 is standing on a scale 810, where the tissues of the user's body is modeled as a series of impedance elements, and where the time-varying impedance elements change in response to cardiovascular and non-cardiovascular movements of the user. ECG and IPG measurements are sensed through the feet. Measuring ECG and IPG measurements is challenging due to small impedance signals with (1) low SNR, and because they are (2) frequently masked or distorted by other electrical activity in the body such as the muscle firings in the legs to maintain balance. The human body is unsteady while standing still, and constant changes in weight distribution occur to maintain balance. As such, cardiovascular signals that are measured with weighing scale-based sensors typically yield signals with poor SNR, such as the Foot IPG and standing BCG. Thus, such scale-based signals use a stable and high quality synchronous timing reference, to segment individual heartbeat-related signals for signal averaging to yield an averaged signal with higher SNR versus respective individual measurements.

The ECG, in accordance with various embodiments, is used as the reference (or trigger) signal to segment a series of heartbeat-related signals measured by secondary sensors (optical, electrical, magnetic, pressure, microwave, piezo, etc.) for averaging a series of heartbeat-related signals together, to improve the SNR of the secondary measurement. The ECG has an intrinsically high SNR when measured with body-worn gel electrodes, or via dry electrodes on handgrip sensors. In contrast, the ECG has a low SNR when measured using foot electrodes while standing on said scale platforms; unless the user is standing perfectly still to eliminate electrical noises from the leg muscles firing due to body motion. As such, ECG measurements at the feet while standing are considered to be an unreliable trigger signal (low SNR). Therefore, it is often difficult to obtain a reliable cardiovascular trigger reference timing when using ECG sensors incorporated in base scale platform devices. Both Inan, et al. (IEEE Transactions on Information Technology in Biomedicine, 14:5, 1188-1196, 2010) and Shin, et al. (Physiological Measurement, 30, 679-693, 2009) have shown that the ECG component of the electrical signal measured between the two feet while standing was rapidly overpowered by the electromyogram (EMG) signal resulting from the leg muscle activity involved in maintaining balance.

The accuracy of cardiovascular information obtained from weighing scale platforms is influenced by measurement time. The number of beats obtained from heartbeat-related signals for signal averaging is a function of measurement time and heart rate. The Mayo Clinic cites that typical resting heart rates range from 60 to 100 beats per minute. Therefore, short signal acquisition periods may yield a low number of beats to average, which may cause measurement uncertainty, also known as the standard error in the mean (SEM). SEM is the standard deviation of the sample mean estimate of a population mean. Where, SE is the standard error in the samples N, which is related to the standard error or the population S.

$$SE = \frac{S}{\sqrt{N}}$$

For example, a five second signal acquisition period may yield a maximum of five to eight beats for ensemble averaging, while a 10 second signal acquisition could yield 10-16 beats. However, the number of beats available for averaging and SNR determination is usually reduced for the following factors; (1) truncation of the first and last ensemble beat in the recording by the algorithm, (2) triggering beats falsely missed by triggering algorithm, (3) cardiorespiratory variability, (4) excessive body motion corrupting the trigger and Foot IPG signal, and (5) loss of foot contact with the measurement electrodes.

Sources of noise can use multiple solutions for overall SNR improvements for the signal being averaged. Longer measurement times increase the number of beats lost to truncation, false missed triggering, and excessive motion. Longer measurement times also reduce variability from cardiorespiratory effects. Therefore, if shorter measurement times (e.g., less than 30 seconds) are used for scale-based sensor platforms, sensing improvements need to tolerate body motion and loss of foot contact with the measurement electrodes.

The human cardiovascular system includes a heart with four chambers, separated by valves that return blood to the heart from the venous system into the right side of the heart, through the pulmonary circulation to oxygenate the blood, which then returns to the left side of the heart, where the oxygenated blood is pressurized by the left ventricles and is pumped into the arterial circulation, where blood is distributed to the organs and tissues to supply oxygen. The cardiovascular or circulatory system is designed to ensure maintenance of oxygen availability and is often the limiting factor for cell survival. The heart normally pumps five to six liters of blood every minute during rest and maximum cardiac output during exercise can increase up to seven-fold, by modulating heart rate and stroke volume. The factors that affect heart rate include the degree of autonomic innervation, fitness level, age and hormones. Factors affecting stroke volume include heart size, fitness level, contractility or pre-ejection period, ejection duration, preload or end-diastolic volume, and afterload or systemic resistance. The cardiovascular system is constantly adapting to maintain a homeostasis (set point) that minimizes the work done by the heart to maintain cardiac output. As such, blood pressure is continually adjusting to minimize work demands during rest.

Each cardiac cycle results in a pulse of blood being delivered into the arterial tree. The heart completes cycles of atrial systole, delivering blood to the ventricles, followed by ventricular systole delivering blood into the lungs and the systemic arterial circulation, where the diastole cycle begins. In early diastole the ventricles relax and fill with blood, then in mid-diastole the atria and ventricles are relaxed and the ventricles continue to fill with blood. In late diastole, the sinoatrial node (the heart's pacemaker) depolarizes then contracts the atria, the ventricles are filled with more blood and the depolarization then reaches the atrioventricular node and enters the ventricular side, beginning the systole phase. The ventricles contract, and the blood is pumped from the ventricles to the arteries.

The ECG is the measurement of the heart's electrical activity and can be described in five phases. The P-wave represents atrial depolarization, the PR interval is the time between the P-wave and the start of the QRS complex. The QRS wave complex represents ventricular depolarization. The QRS complex is the strongest wave in the ECG and is frequently used as the de facto timing reference for the cardiovascular cycle. Atrial repolarization is masked by the QRS complex. The ST interval then follows which represents the period of zero potential between ventricular depolarization and repolarization. The cycle concludes with the T-wave representing ventricular repolarization.

The blood ejected into the arteries creates vascular movements due to the blood's momentum. The blood mass ejected by the heart first travels headward in the ascending aorta and travels around the aortic arch then travels down the descending aorta. The diameter of the aorta increases significantly during the systole phase due to the high compliance (low stiffness) of the aortic wall. Blood traveling in the descending aorta then bifurcates in the iliac branch, which then transitions into a stiffer arterial region due to the muscular artery composition of the leg arteries. The blood pulsation continues down the leg and foot. All along the way, the arteries branch into arteries of smaller diameter until reaching the capillary beds where the pulsatile blood flow turns into steady blood flow, delivering oxygen to the tissues. The blood then returns to the venous system terminating in the vena cava, where blood returns to the right atrium of the heart for the subsequent cardiac cycle.

Surprisingly, high quality simultaneous recordings of the Leg IPG and Foot IPG are attainable in a practical manner (e.g., a user operating the device correctly simply by standing on the impedance body scale foot electrodes), and is used to obtain reliable trigger fiducial timings from the Leg IPG signal. This acquisition is less sensitive to motion-induced noise from the Leg EMG than often compromises Leg ECG measurements. Furthermore, interleaving the two Kelvin electrode pairs for a single foot results in a design that is insensitive to foot placement within the boundaries of the overall electrode area. As such, the user is no longer constrained to comply with accurate foot placement on conventional single foot Kelvin arrangements, which are prone to introducing motion artifacts into the IPG signal, or result in a loss of contact if the foot is slightly misaligned. Interleaved designs begin when one or more electrode surfaces cross over a single imaginary boundary line separating an excitation and sensing electrode pair. The interleaving is configured to maintain uniform foot surface contact area on the excitation and sensing electrode pair, regardless of the positioning of the foot over the combined area of the electrode pair.

Various aspects of the present disclosure include a weighing scale platform (e.g., scale 110) of an area sufficient for an adult of average size to stand comfortably still and minimize postural swaying. The nominal scale length (same orientation as foot length) is 12 inches and the width is 12 inches. The width can be increased to be consistent with the feet at shoulder width or slightly broader (e.g., 14 to 18 inches, respectively).

Figure 9:
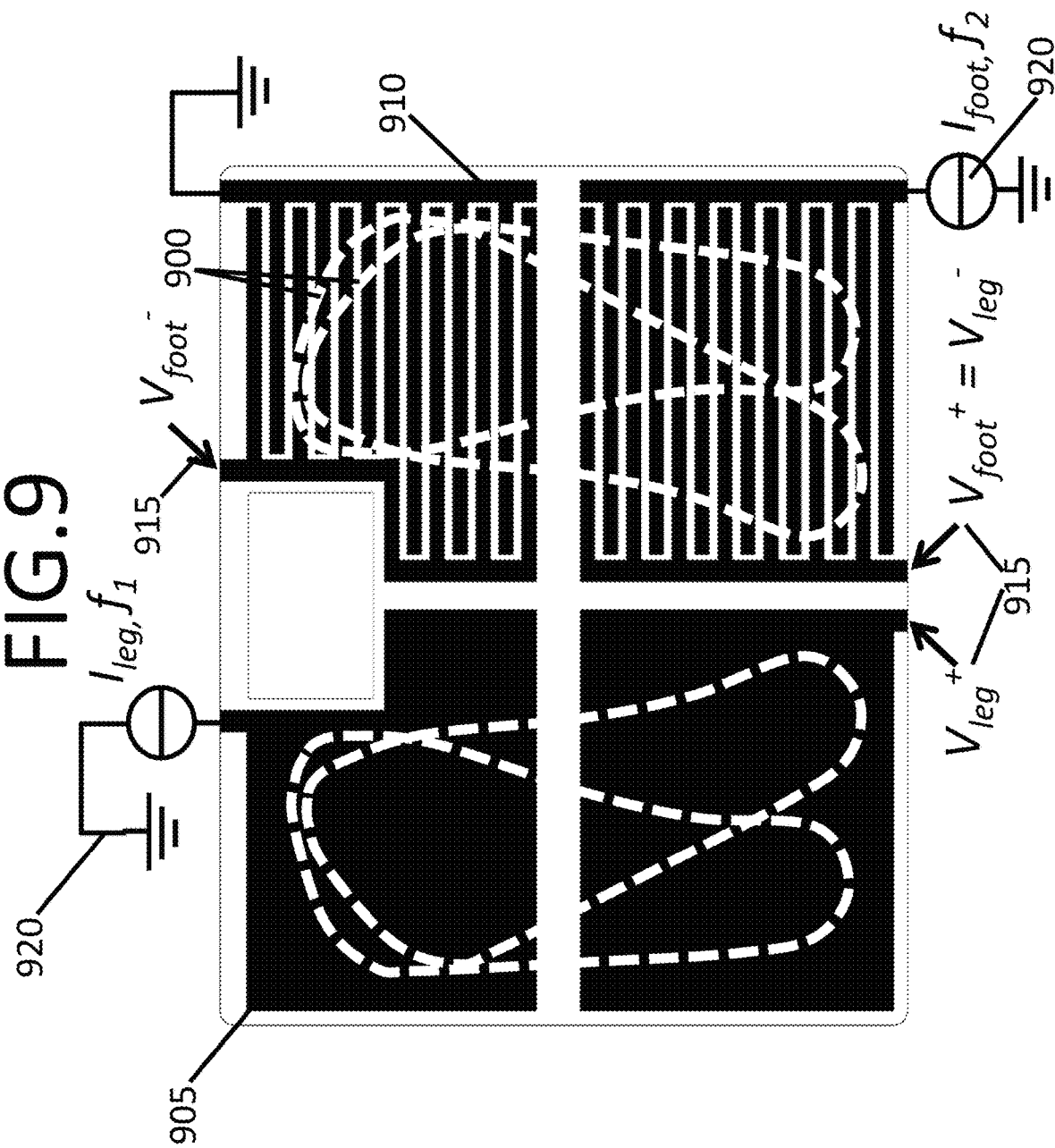
FIG. 9 shows an example of the insensitivity to foot placement on scale electrodes with multiple excitation and sensing current paths, consistent with various aspects of the present disclosure.

FIG. 9 shows an example of the insensitivity to foot placement 900 on scale electrode pairs 905/910 with multiple excitation paths 920 and sensing current paths 915, consistent with various aspects of the present disclosure. An aspect of the platform is that it has a thickness and strength to support a human adult of at least 200 pounds without fracturing. Another aspect of the device platform is comprised of at least six electrodes, where the first electrode pair 905 is solid and the second electrode pair 910 is interleaved. Another aspect is that the first and second interleaved electrode pairs 905/910 are separated by a distance of at least 40+/−5 millimeters, where the nominal separation of less than 40 millimeters has been shown to degrade the single Foot IPG signal. Another key aspect is the electrode patterns are made from materials with low resistivity such as stainless steel, aluminum, hardened gold, ITO, index matched ITO (IMITO), carbon printed electrodes, conductive tapes, silver-impregnated carbon printed electrodes, conductive adhesives, and similar materials with resistivity lower than 300 ohms/sq. In the certain embodiments, the resistivity is below 150 ohms/sq. The electrodes are connected to the electronic circuitry in the scale by routing the electrodes around the edges of the scale to the surface below, or through at least one hole in the scale (e.g., a via hole).

Suitable electrode arrangements for dual Foot IPG measurements can be realized in other embodiments. In certain embodiments, the interleaved electrodes are patterned on the reverse side of a thin piece (e.g., less than 2 mm) of high-ion-exchange (HIE) glass, which is attached to a scale substrate and used in capacitive sensing mode. In certain embodiments, the interleaved electrodes are patterned onto a thin piece of paper or plastic which are rolled up or folded for easy storage. In certain embodiments, the interleaved electrodes are integrated onto the surface of a tablet computer for portable IPG measurements. In certain embodiments, the interleaved electrodes are patterned onto a kapton substrate that is used as a flex circuit.

In certain embodiments, the scale area has a length of 10 inches with a width of eight inches for a miniature scale platform. Alternatively, the scale may be larger (up to 36 inches wide) for use in bariatric class scales. In certain embodiments, the scale platform with interleaved electrodes is incorporated into a floor tile that is incorporated into a room such as a bathroom. In certain embodiments, the scale folds in half with a hinge for improved portability and storage. Alternatively, the scale platform is comprised of two separable halves, one half for the left foot and the other half for the right foot, for improved portability and storage. In certain embodiments for ambulatory measurements, the interleaved excitation and sensing electrode pairs are incorporated into a shoe insert for the detection of heart rate and a corresponding pulse arrival time (PAT). Alternatively, the interleaved excitation and sensing electrode pairs are incorporated into a pair of socks, to be worn for the detection of heart rate and a corresponding PAT.

In some embodiments, the leg and foot impedance measurements are simultaneously carried out using a multi-frequency approach, in which the leg and foot impedances are excited by currents modulated at two different frequencies, and the resulting voltages are selectively measured using a synchronous demodulator. This homodyning approach is used to separate signals (in this case, the voltage drop due to the imposed current) with accuracy and selectivity.

This measurement configuration is based on a four-point configuration in order to minimize the impact of the contact resistance between the electrode and the foot, a practice well-known in the art of impedance measurement. In this configuration the current is injected from a set of two electrodes (the "injection" and "return" electrodes), and the voltage drop resulting from the passage of this current through the resistance is sensed by two separate electrodes (the "sense" electrodes), usually located in the path of the current. Since the sense electrodes are not carrying any current (by virtue of their connection to a high-impedance differential amplifier), the contact impedance does not significantly alter the sensed voltage.

In order to sense two distinct segments of the body (the legs and the foot), two separate current paths are defined by way of electrode positioning. Therefore two injection electrodes are used, each connected to a current source modulated at a different frequency. The injection electrode for leg impedance is located under the plantar region of the left foot, while the injection electrode for the Foot IPG is located under the heel of the right foot. Both current sources share the same return electrode located under the plantar region of the right foot. This is an illustrative example; other configurations may be used.

The sensing electrodes can be localized so as to sense the corresponding segments. Leg IPG sensing electrodes are located under the heels of each foot, while the two foot sensing electrodes are located under the heel and plantar areas of the right foot. The inter-digitated nature of the right foot electrodes ensures a four-point contact for proper impedance measurement, irrespective of the foot position, as already explained.

Figure 10A:
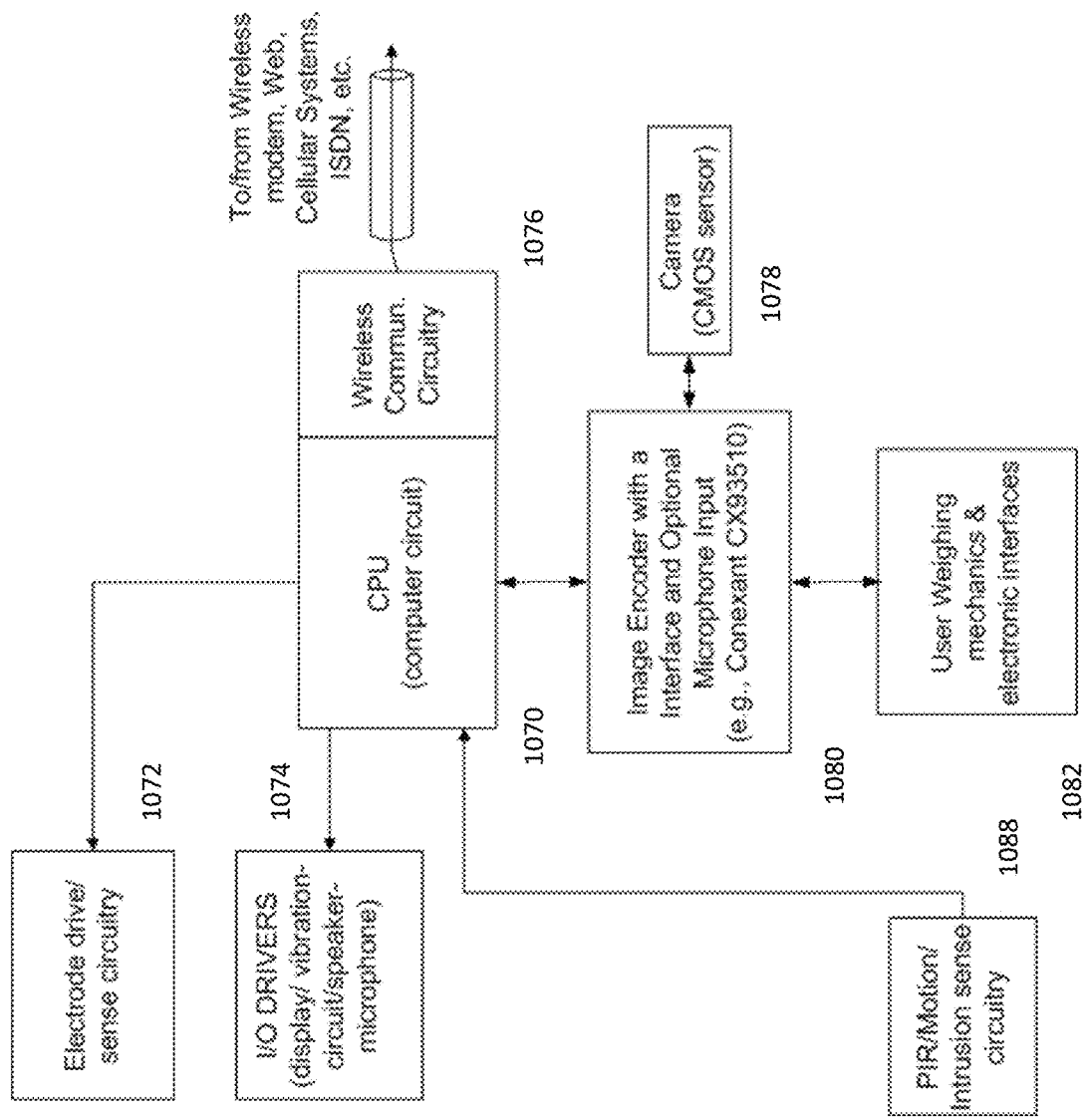
FIG. 10A depicts an example block diagram of circuitry for operating core circuits and modules, including, for example, those of FIGS. 11A-11B, used in various specific embodiments of the present disclosure.

FIG. 10A depicts an example block diagram of circuitry for operating core circuits and modules of the scale, used in various specific embodiments of the present disclosure. Consistent with yet further embodiments of the present disclosure, FIG. 10A depicts an example block diagram of circuitry for operating core circuits and modules, including, for example, the operation of a CPU with the related and more specific circuit blocks/modules in FIGS. 10A-10B. As shown in the center of FIG. 10A, the main computer circuit 1070 is shown with other previously-mentioned circuitry in a generalized manner without showing some of the detailed circuitry such as for amplification and current injection/sensing (1072). The computer circuit 1070 can be used as a control circuit with an internal memory circuit for causing, processing and/or receiving sensed input signals as at block 1072. As discussed, these sensed signals are responsive to injection current and/or these signals are sensed at least for initially locating positions of the foot or feet on the platform area, by less complex grid-based sense circuitry surrounding the platform area as is conventional in capacitive touch-screen surfaces which, in certain embodiments, the platform area includes.

As noted, the memory circuit is used not only for the user profile memory, but also to provide configuration and/or program code and/or other data such as user-specific data from another authorized source such as from a user monitoring his/her logged data and/or profile from an external device, such as a remote desk-top. The external device communicates with and access such data via a wireless communication circuit 1076 via a wireless modem, router, ISDN channel, cellular systems, Bluetooth and/or other broadband pathway or private channel. For example, the wireless communication circuit 1076 provides an interface between an application on the user's cellular telephone/tablet (e.g., phablet, IPhone and/or IPad) and the platform apparatus, wherefrom the IPhone output/input interface for the platform (scale) apparatus including, for example, an output display, speaker and/or microphone, and vibration circuitry;

each of these I/O aspects and components being discussed herein in connection with other example embodiments.

A camera 1078 and image encoder circuit 1080 (with compression and related features) can also be incorporated as an option. As discussed above, the weighing scale components, as in block 1082, are also optionally included in the housing which encloses and/or surrounds the platform apparatus.

For long-lasting battery life in the platform apparatus (batteries not shown), at least the CPU 1070, the wireless communication circuit 1076, and other current draining circuits are inactive unless and until activated in response to the intrusion/sense circuitry 1088. As shown, one specific implementation employs a Conexant chip (e.g., CX93510) to assist in the low-power operation. This type of circuitry is specifically designed for motion sensors configured with a camera for visual verification and image and video monitoring applications (such as by supporting JPEG and MJPEG image compression and processing for both color and black and white images). When combined with an external CMOS sensor, the chip retrieves and stores compressed JPEG and audio data in an on-chip memory circuit (e.g., 256 KB/128 KB frame buffer) so as to alleviate the necessity of external memory. The chip uses a simple register set via the microprocessor interface and allows for wide flexibility in terms of compatible operation with another microprocessor.

In one specific embodiment, a method of using the platform with the plurality of electrodes concurrently contacting a limb of the user, includes operating such to automatically obtain measurement signals from the plurality of electrodes. As noted above, these measurement signals may be through less-complex (e.g., capacitive grid-type) sense circuitry. Before or while obtaining a plurality of measurement signals by operating the circuitry, the signal-sense circuitry 1088 is used to sense wireless-signals indicative of the user approaching the platform and, in response, cause the CPU circuitry 1070 to transition from a reduced power-consumption mode of operation and at least one higher power-consumption mode of operation. After the circuitry is operating in the higher power-consumption mode of operation, the CPU accesses the user-corresponding data stored in the memory circuit and thereafter causes a plurality of impedance signals to be obtained by using the plurality of electrodes while they are contacting the user via the platform; therefrom, the CPU generates signals corresponding to cardiovascular timings of the user.

This method employs the signal-sense circuit as a passive infrared detector and with the CPU programmed (as a separate module) to evaluate whether radiation from the passive infrared detector is indicative of a human. For example, in response to a sensed levels of radiation that corresponds to a live being that has a size which is less than a person of a three-foot height, and/or not being sensed as moving for more than a couple seconds, the sensed levels of radiation is assessed as being a non-human.

Accordingly, in response to user be recognized as human, the CPU is activated and begins to the discernment process of which user might be approaching. This is performed by the CPU accessing the user-corresponding data stored in the memory circuit (the user profile memory). If the user is recognized based on parameters such as discussed above (e.g., time of morning, speed of approach, etc.), the CPU also selects one of a plurality of different types of user-discernible visual/audible/tactile information and for presenting the discerned user with visual/audible/tactile information that was retrieved from the memory as being specific to the user. For example, user-selected visual/audible data is outputted for the user. Also, responsive to the motion detection indication, the camera is activated to capture at least one image of the user while the user is approaching the platform (and/or while the user is on the platform to log confirmation of the same user with the measured impedance information). As shown in block 1074 of FIG. 10A, where a speaker is also integrated with the CPU, the user can simply command the platform apparatus to start the process and activation accordingly proceeds.

In another such method, the circuitry of FIG. 10A is used with the plurality of electrodes being interleaved and engaging the user, as a combination weighing scale (via block 1082) and a physiologic user-specific impedance-measurement device. By using the impedance signals and obtaining at least two impedance signals between one foot of the user and another location of the user, the interleaved electrodes assist the CPU in providing measurement results that indicate one or more of the following user-specific attributes as being indicative or common to the user: foot impedance, foot length, and type of arch, and wherein one or more of the user-specific attributes are accessed, by being read or stored, in the memory circuit and identified as being specific to the user. This information, in some embodiments, is later retrieved by the user, medical and/or security personnel, according to a data-access authorization protocol as might be established upon initial configuration for the user.

Figure 10B:
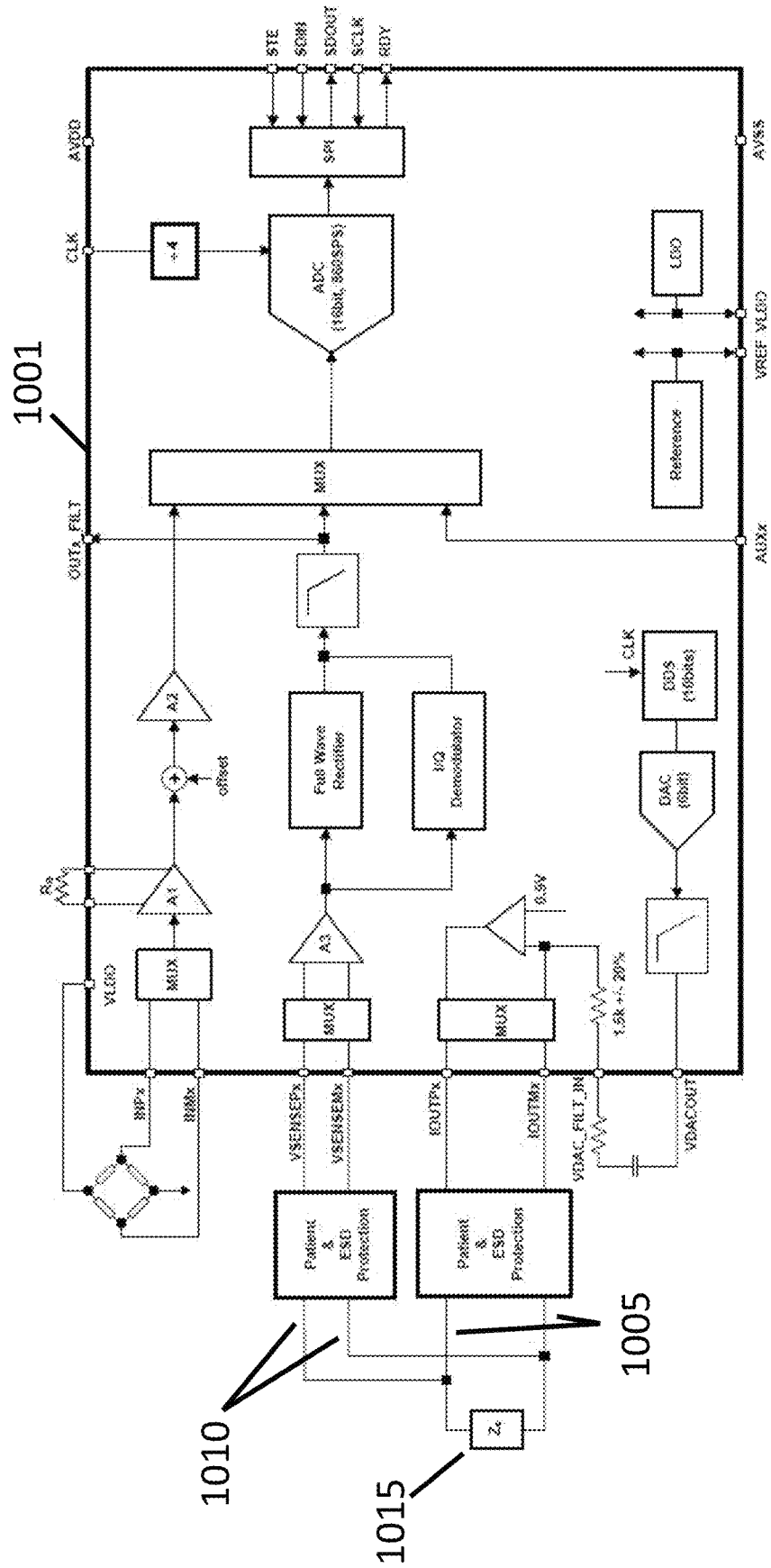
FIG. 10B shows an exemplary block diagram depicting the circuitry for interpreting signals received from electrodes.

FIG. 10B shows an exemplary block diagram depicting the circuitry for interpreting signals received from electrodes. The input electrodes 1005 transmit various electrical signals through the patient's body (depending on the desired biometric and physiological test to be conducted) and output electrodes 1010 receive the modified signal as affected by a user's electrical impedance 1015. Once received by the output electrodes 1010, the modified signal is processed by processor circuitry 1001 based on the selected test. Signal processing conducted by the processor circuitry 1001 is discussed in more detail below (with regard to FIGS. 11A-

B). In certain embodiments of the present disclosure, the circuitry within 1001 is provided by Texas Instruments part #AFE4300.

Figure 11A:
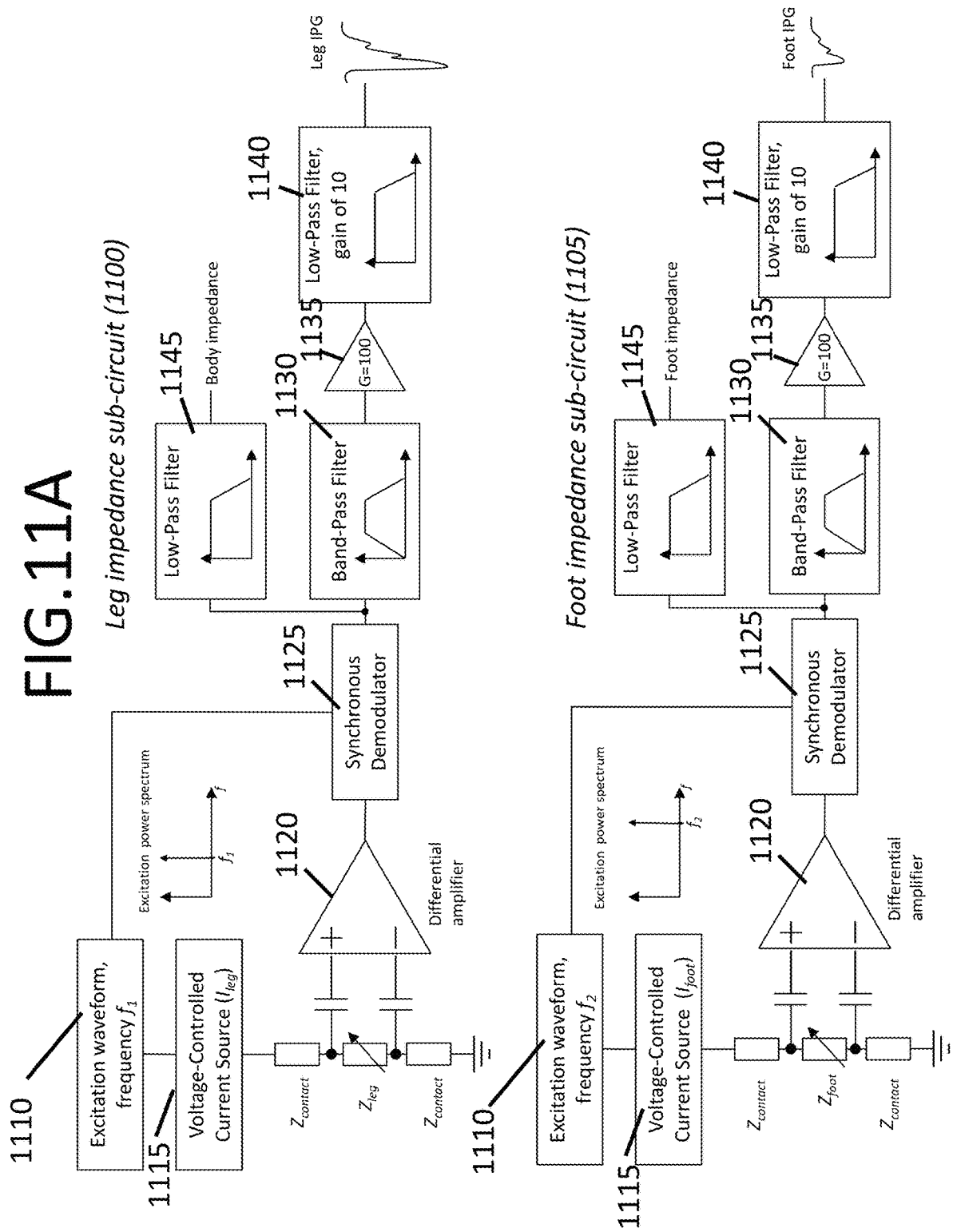
FIGS. 11A-11B show example block diagrams depicting the circuitry for sensing and measuring the cardiovascular time-varying IPG raw signals and steps to obtain a filtered IPG waveform, consistent with various aspects of the present disclosure.
Figure 11B:
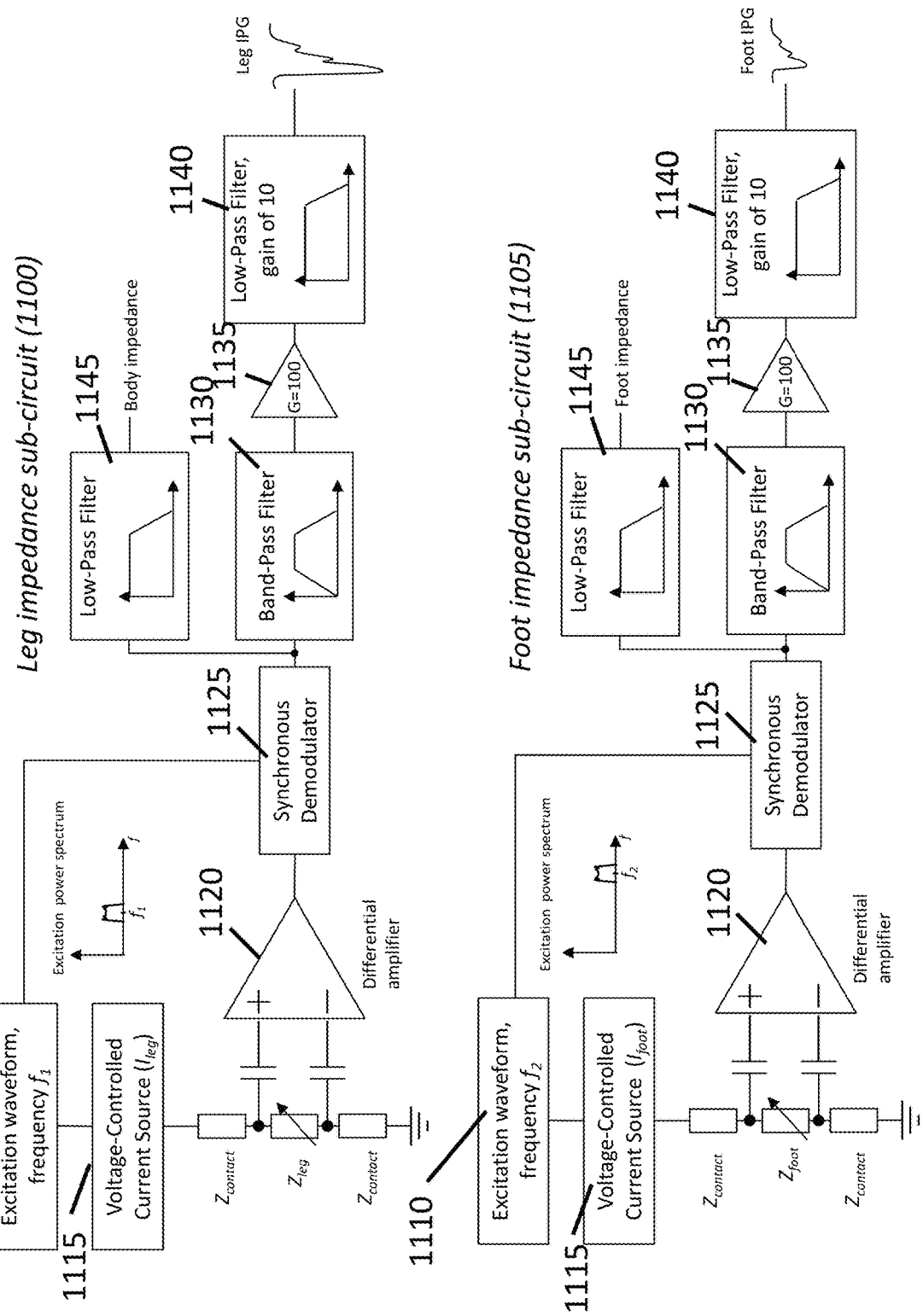

FIGS. 11A-11B show example block diagrams depicting the circuitry for sensing and measuring the cardiovascular time-varying IPG raw signals and steps to obtain a filtered IPG waveform, consistent with various aspects of the present disclosure. The example block diagrams shown in FIGS. 11A-11B are separated into a leg impedance sub-circuit 1100 and a foot impedance sub-circuit 1105.

Excitation is provided by way of an excitation waveform circuit 1110. The excitation waveform circuit 1110 provides an excitation signal by way of various types of frequency signals (as is shown in FIG. 11A) or, more specifically, a square wave signal (as shown in FIG. 11B). As is shown in FIG. 11B, the square wave signal is a 5 V at a frequency between 15,625 Hz and 1 MHz is generated from a quartz oscillator (such as an ECS-100AC from ECS International, Inc.) divided down by a chain of toggle flip-flops (e.g. a CD4024 from Texas Instruments, Inc.), each dividing stage providing a frequency half of its input (i.e., 1 Mhz, 500 kHz, 250 kHz, 125 kHz, 62.5 kHz, 31.250 kHz and 15.625 kHz). This (square) wave is then AC-coupled, scaled down to the desired amplitude and fed to a voltage-controlled current source circuit 815. The generated current is passed through a decoupling capacitor (for safety) to the excitation electrode, and returned to ground through the return electrode (grounded-load configuration). Amplitudes of 1 and 4 mA peak-to-peak are typically used for Leg and Foot IPGs, respectively. The voltage drop across the segment of interest (legs or foot) is sensed using an instrumentation differential amplifier (e.g., Analog Devices AD8421) 820. The sense electrodes on the scale are AC-coupled to the input of the differential amplifier 820 (configured for unity gain), and any residual DC offset is removed with a DC restoration circuit (as exemplified in Burr-Brown App Note Application Bulletin, SBOA003, 1991, or Burr-Brown/Texas Instruments INA118 datasheet).

The signal is then demodulated with a synchronous demodulator circuit 1125. The demodulation is achieved in this example by multiplying the signal by 1 or −1 synchronously with the current excitation. Such alternating gain is provided by an operational amplifier and an analog switch (SPST), such as an ADG442 from Analog Devices). More specifically, the signal is connected to both positive and negative inputs through 10 kOhm resistors. The output is connected to the negative input with a 10 kOhm resistor as well, and the switch is connected between the ground and the positive input. When open, the gain of the stage is unity. When closed (positive input grounded), the stage acts as an inverting amplifier of the gain −1. Alternatively, other demodulators such as analog multipliers or mixers can be used.

Once demodulated, the signal is band-pass filtered (0.4-80 Hz) with a first-order band-pass filter circuit 1130 before being amplified with a gain of 100 with a non-inverting amplifier circuit 1135 (e.g., using an LT1058 operational amplifier from Linear Technologies). The amplified signal is further amplified by 10 and low-pass filtered (cut-off at 30 Hz) using a low-pass filter circuit 1140 such as 2-pole Sallen-Key filter stage with gain. The signal is then ready for digitization and further processing. In certain embodiments, the amplified signal is passed through an additional low-pass filter circuit 1145 to determine body or foot impedance.

In certain embodiments, the generation of the excitation voltage signal, of appropriate frequency and amplitude, is carried out by a microcontroller, such as MSP430 (Texas Instruments, Inc.). The voltage waveform is generated using the on-chip timers and digital input/outputs or pulse width modulation (PWM) peripherals, and scaled down to the appropriate voltage through fixed resistive dividers, active attenuators/amplifiers using on-chip or off-chip operational amplifiers, as well as programmable gain amplifiers or programmable resistors. Alternatively, the waveforms is directly generated by on- or off-chip digital-to-analog converters (DACs).

In certain embodiments, the shape of the excitation is not square, but sinusoidal. Such configuration reduces the requirements on bandwidth and slew rate for the current source and instrumentation amplifier. Harmonics, potentially leading to higher electromagnetic interference (EMI), are also reduced. Such excitation also reduce electronics noise on the circuit itself. Lastly, the lack of harmonics from sine wave excitation may provide a more flexible selection of frequencies in a multi-frequency impedance system, as excitation waveforms have fewer opportunities to interfere between each other. Due to the concentration of energy in the fundamental frequency, sine wave excitation are also more power-efficient.

In certain embodiments, the shape of the excitation is not square, but trapezoidal. The trapezoidal waves (or square waves whose edges have been smoothed out by a limited bandwidth or slew rate) provide an advantage in term of EMI and electronic noise due to the reduced harmonics.

To further reduce potential EMI, other strategies may be used, such as by dithering the square wave signal (i.e., introducing jitter in the edges following a fixed or random pattern) which leads to so-called spread spectrum signals, in which the energy is not localized at one specific frequency (or a set of harmonics), but rather distributed around a frequency (or a set of harmonics). An example of a spread-spectrum circuit suitable for Dual-IPG measurement is shown in FIG. 11B. Because of the synchronous demodulation scheme, phase-to-phase variability introduced by spread-spectrum techniques does not affect the impedance measurement. Such a spread-spectrum signal can be generated by, but not limited to, specialized circuits (e.g., Maxim MAX31C80, SiTime SiT9001), or generic microcontrollers (see Application Report SLAA291, Texas Instruments, Inc.). These spread-spectrum techniques can be combined with clock dividers to generate lower frequencies as well.

As may be clear to one skilled in the art, these methods of simultaneous measurement of impedance in the leg and foot are used for standard Body Impedance Analysis (BIA), with the aim of extracting relative content of total water, free-water, fat mass and others. Impedance measurements for BIA are typically done at frequencies ranging from kilohertz up to several megahertz. The multi-frequency measurement methods described above are readily used for such BIA, provided the circuit is modified so that the DC component of the impedance is not canceled by the instrumentation amplifier (no DC restoration circuit used). The high-pass filter can be implemented after the instrumentation amplifier, enabling the measurement of the DC component used for BIA. This multi-frequency technique can also be combined with traditional sequential measurements often used for BIA, in which the impedance is measured at several frequencies sequentially. These measurements can be repeated in several body segments for segmental BIAs, using a switch matrix to drive the current into the desired body segments.

Figure 12:
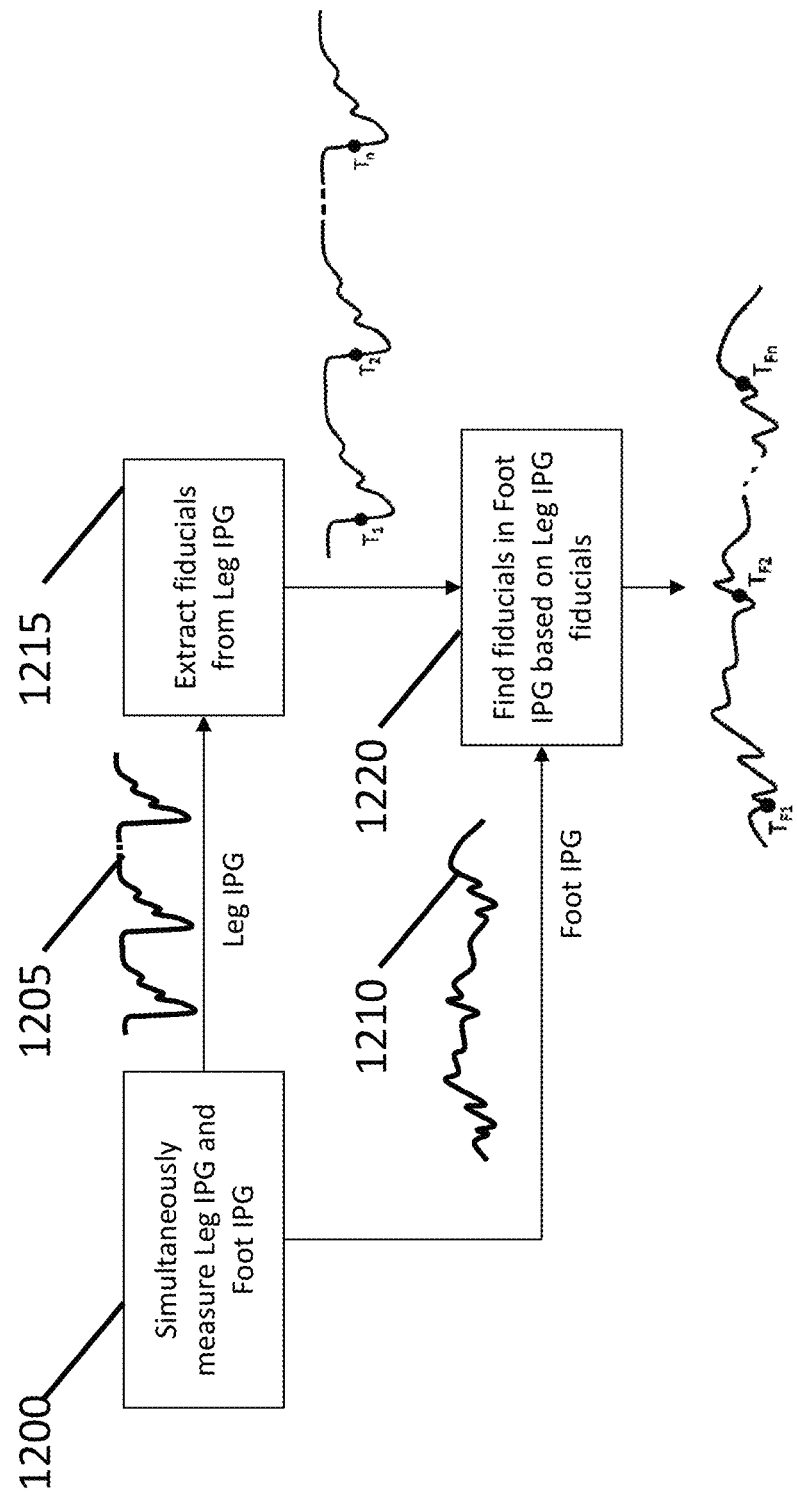
FIG. 12 shows an example block diagram depicting signal processing steps to obtain fiducial references from the individual Leg IPG "beats," which are subsequently used to obtain fiducials in the Foot IPG, consistent with various aspects of the present disclosure.
Figure 16A:
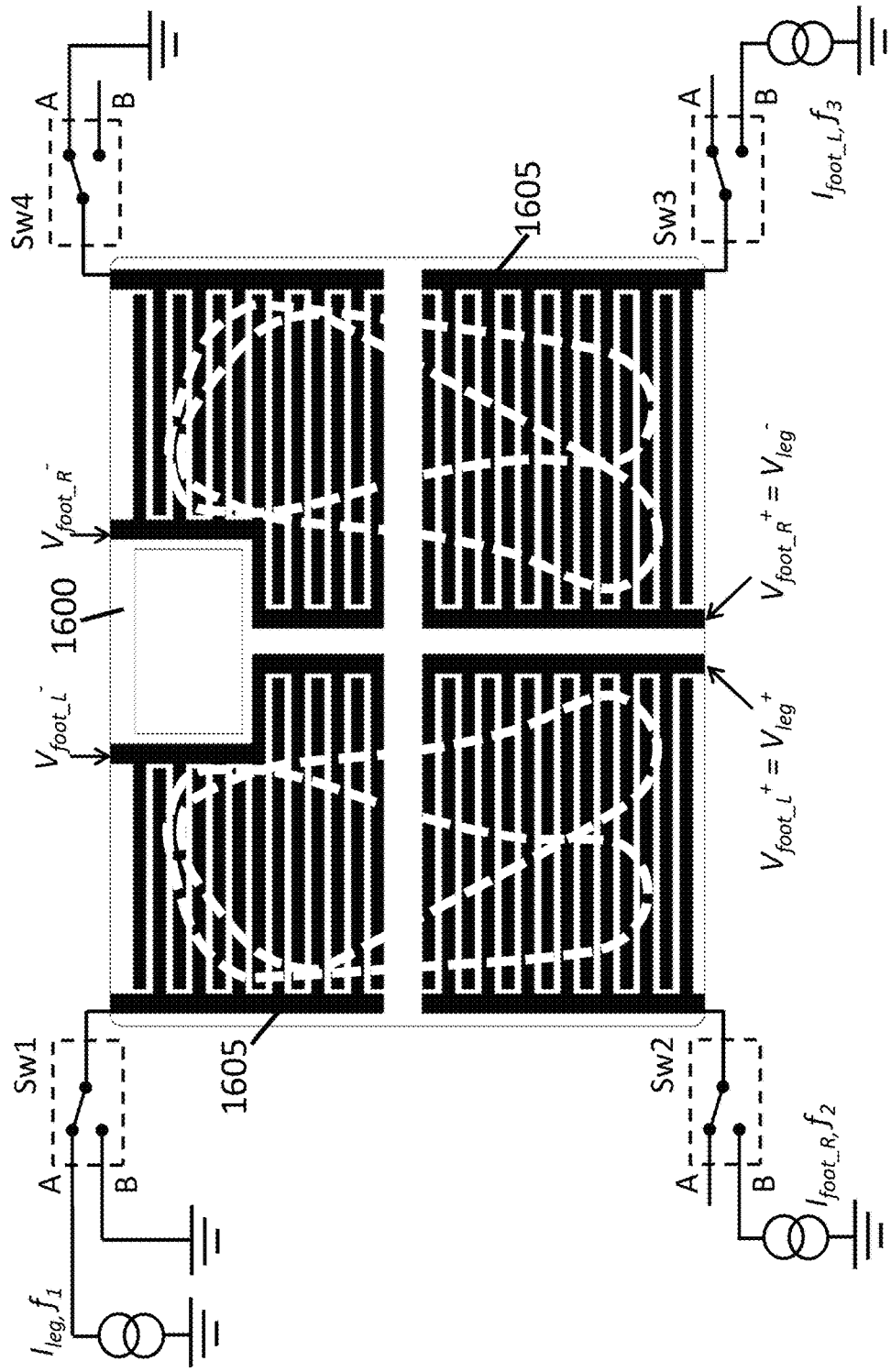
FIG. 16A shows another example of a scale with interleaved foot electrodes to inject and sense current from one foot to another foot, and to measure Foot IPG signals in both feet, consistent with various aspects of the present disclosure.
Figure 17A:
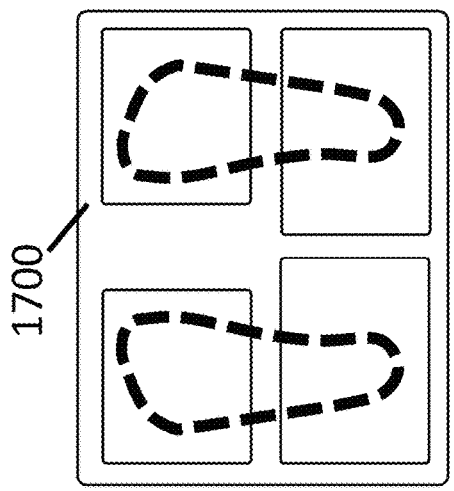
FIGS. 17A-D show an example breakdown of a scale with interleaved foot electrodes to inject and sense current from one foot to another foot, and within one foot, consistent with various aspects of the present disclosure.
Figure 17B:
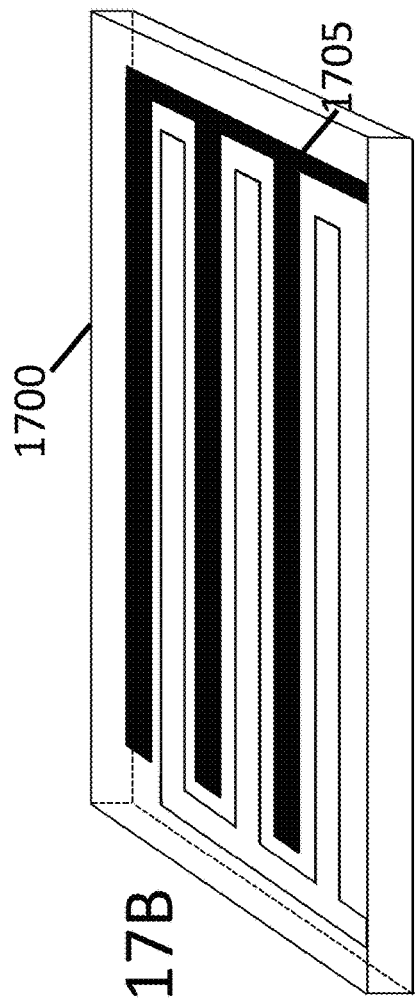
Figure 17C:
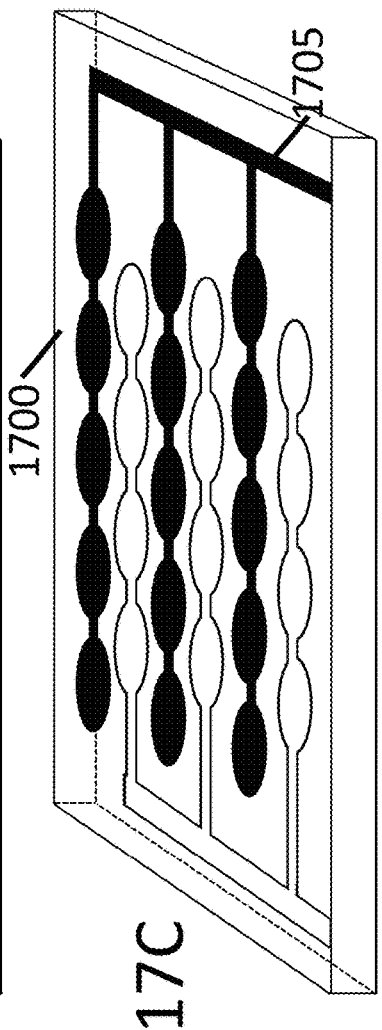
Figure 17D:
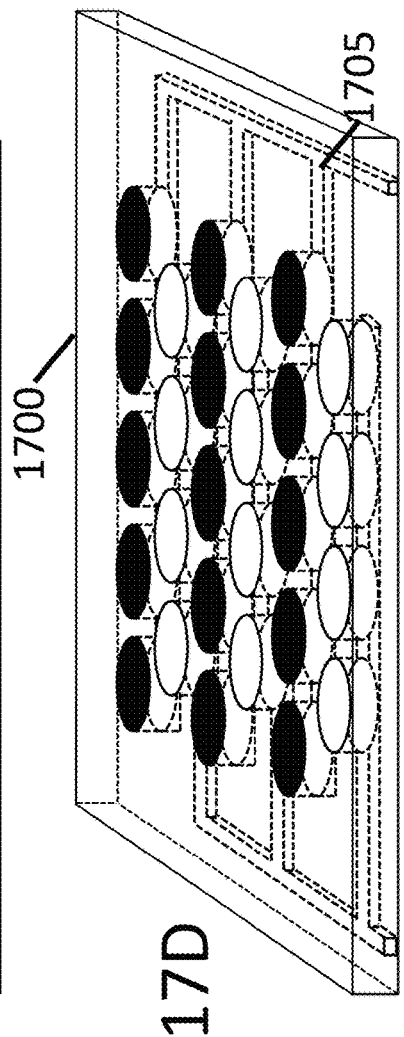

While FIG. 12 shows a circuit and electrode configuration suitable to measure two different segments (legs and one foot), this approach is not readily extendable to more segments due to the shared current return electrode (ground). To overcome this limitation, and in particular to provide simultaneous measurements in both feet, the system is augmented with analog switches to provide time-multiplexing of the impedance measurements in the different segments. This multiplexing includes a one-time sequencing (each segment is measured once), or interleaved at a high-enough frequency so that the signal is simultaneously measured on each segment. The minimum multiplexing rate for proper reconstruction is twice the bandwidth of the measured signal, based on signal processing theory, which equals to about 100 Hz for the impedance signal considered here. The rate also allows for the signal path to settle in between switching, usually limiting the maximum multiplexing rate. Referring to FIG. 16A, as an example, one cycle starts the measurement of the leg impedance and left foot impedances (similarly to previously described, sharing a common return electrode), but then follow with a measurement of the right foot after reconfiguring the switches. Typical switch configurations for the various measurements are shown in the table which follows.

|  | Switch #1 (Sw1) | Switch #2 (Sw2) | Switch #3 (Sw3) | Switch #4 (Sw4) |
| --- | --- | --- | --- | --- |
| Legs | A | A or B | A or B | A |
| Right Foot | A | A or B | B | A |
| Left Foot | B | B | A or B | B |

Since right and left feet are measured sequentially, in some embodiments, a unique source (at the same frequency) is used to measure both, providing that the current source is not connected to the two feet simultaneously through the switches, in which case the current would be divided between two paths. Another example embodiment includes a fully-sequential measurement, using a single current source (at a single frequency) successively connected to the three different injection electrodes, with the proper switch configuration sequence (no split current path).

In certain embodiments, the measurement of various body segments, and in particular the legs, right foot and left foot, is achieved simultaneously due to as many floating current sources as segments to be measured, running at separate frequency so they can individually be demodulated. Such configuration is exemplified in FIG. 16B for three segments (legs, right and left feet). Such configuration provides true simultaneous measurements without the added complexity of time-multiplexing/demultiplexing, and associated switching circuitry. An example of such floating current source can be found in Plickett, et al., Physiological Measurement, 32 (2011). Another approach to floating current sources is the use of transformer-coupled current sources (as depicted in FIG. 16C). Using transformers to inject current into the electrodes enables the use of simpler, grounded-load current sources on the primary, while the electrodes are connected to the secondary. Turn ratio is typically 1:1, and since frequencies of interest for impedance measurement are typically in the 10-1000 kHz (occasionally 1 kHz for BIA), relatively small transformers are used. In order to limit the common mode voltage of the body, one of the electrodes in contact with the foot is grounded.

While certain embodiments presented in the above specification use current sources for excitation, it should be clear to a person skilled in the art that the excitation can also be performed by a voltage source, where the resulting injection current is monitored by a current sense circuit so that impedance is derived by the ratio of the sensed voltage (on the sense electrodes) over the sensed current (injected in the excitation electrodes).

It should be noted that broadband spectroscopy methods can also be used for measuring impedances at several frequencies. Such technique has a lower EMI and simultaneous measurement of impedances at numerous frequencies. These methods typically use a chirp signal, a noise signal or an impulse signal to excite the load (impedance) at many frequencies simultaneously, while sampling the resulting response at high frequency so as to allow the computation (usually in the frequency domain) of the impedance over the desired frequency range. Combined with time-multiplexing and current switching described above, multi-segment broadband spectroscopy can be readily achieved.

Various aspects of the present disclosure are directed toward robust timing extraction of the blood pressure pulse in the foot which is achieved by means of a two-step processing. In a first step, the usually high-SNR Leg IPG is used to derive a reference (trigger) timing for each heart pulse. In a second step, a specific timing in the lower-SNR Foot IPG is extracted by detecting its associated feature within a restricted window of time around the timing of the Leg IPG. Such guided detection leads to a naturally more robust detection of foot timings.

FIG. 12 shows an example block diagram depicting signal processing steps to obtain fiducial references from the individual Leg IPG "beats," which are subsequently used to obtain fiducials in the Foot IPG, consistent with various aspects of the present disclosure. In the first step, as shown in block 1200, the Leg IP and the Foot IPG are simultaneously measured. As shown at 1205, the Leg IPG is low-pass filtered at 20 Hz with an 8-pole Butterworth filter, and inverted so that pulses have an upward peak. The location of the pulses is determined by taking the derivative of this signal, integrating over a 100 ms moving window, zeroing the negative values, removing the large artifacts by zeroing values beyond 15× the median of the signal, zeroing the values below a threshold defined by the mean of the signal, and searching for local maxima. Local maxima closer than a defined refractory period of 300 ms to the preceding ones are dismissed. The result is a time series of pulse reference timings.

As is shown in 1210, the foot IPG is low-pass filtered at 25 Hz with an 8-pole Butterworth filter and inverted (so that pulses have an upward peak). Segments starting from the timings extracted (1215) from the Leg IPG (reference timings) and extending to 80% of the previous pulse interval, but no longer than one second, are defined in the Foot IPG. This defines the time windows where the Foot IPG is expected to occur, avoiding misdetection outside of these windows. In each segment, the derivative of the signal is computed, and the point of maximum positive derivative (maximum acceleration) is extracted. The foot of the IPG signal is computed using an intersecting tangent method, where the fiducial (1220) is defined by the intersection between a first tangent to the IPG at the point of maximum positive derivative and a second tangent to the minimum of the IPG on the left of the maximum positive derivative within the segment.

The time series resulting from this two-step extraction is used in conjunction with another signal to facilitate additional processing. In the present disclosure, these timings are used as reference timings to improve the SNR of BCG signals to subsequently extract intervals between a timing of the BCG (typically the I-wave) and the Foot IPG for the purpose of computing the PWV, as previously disclosed in U.S. 2013/0310700 (Wiard). In certain embodiments, the timings of the Leg IPG are used as reference timings to improve the SNR of BCG signals, and the foot IPG timings are used to extract intervals between timing fiducials of the improved BCG (typically the I-wave) and the Foot IPG for the purpose of computing the PTT and the (PWV).

In certain embodiments, the processing steps include an individual pulse SNR computation after individual timings are extracted, either in Leg IPG or Foot IPG. Following the computation of the SNRs, pulses with a SNR below a threshold value are eliminated from the time series, in order to prevent propagating noise in subsequent processing steps. The individual SNRs are computed in a variety of methods known to a person skilled in the art. For instance, an estimated pulse is computed by ensemble averaging segments of signal around the pulse reference timing. The noise associated with each pulse is defined as the difference between the pulse and the estimated pulse. The SNR is the ratio of the root-mean-square (RMS) value of the estimated pulse over the RMS value of the noise for that pulse.

In certain embodiments, the time interval between the Leg IPG pulses, (as detected by the above-mentioned methods), and the Foot IPG pulses, also detected by the above-mentioned methods, is extracted. The Leg IPG measuring a pulse occurring earlier in the legs is compared to the pulse from the Foot IPG, the interval between these two being related to the propagation speed in the lower body, i.e., the peripheral vasculature. This provides complementary information to the interval extracted between the BCG and the Foot IPG, for instance, and can be used to decouple central versus peripheral vascular properties. It is also complementary to information derived from timings between the BCG and the Leg ICG.

Figure 13:
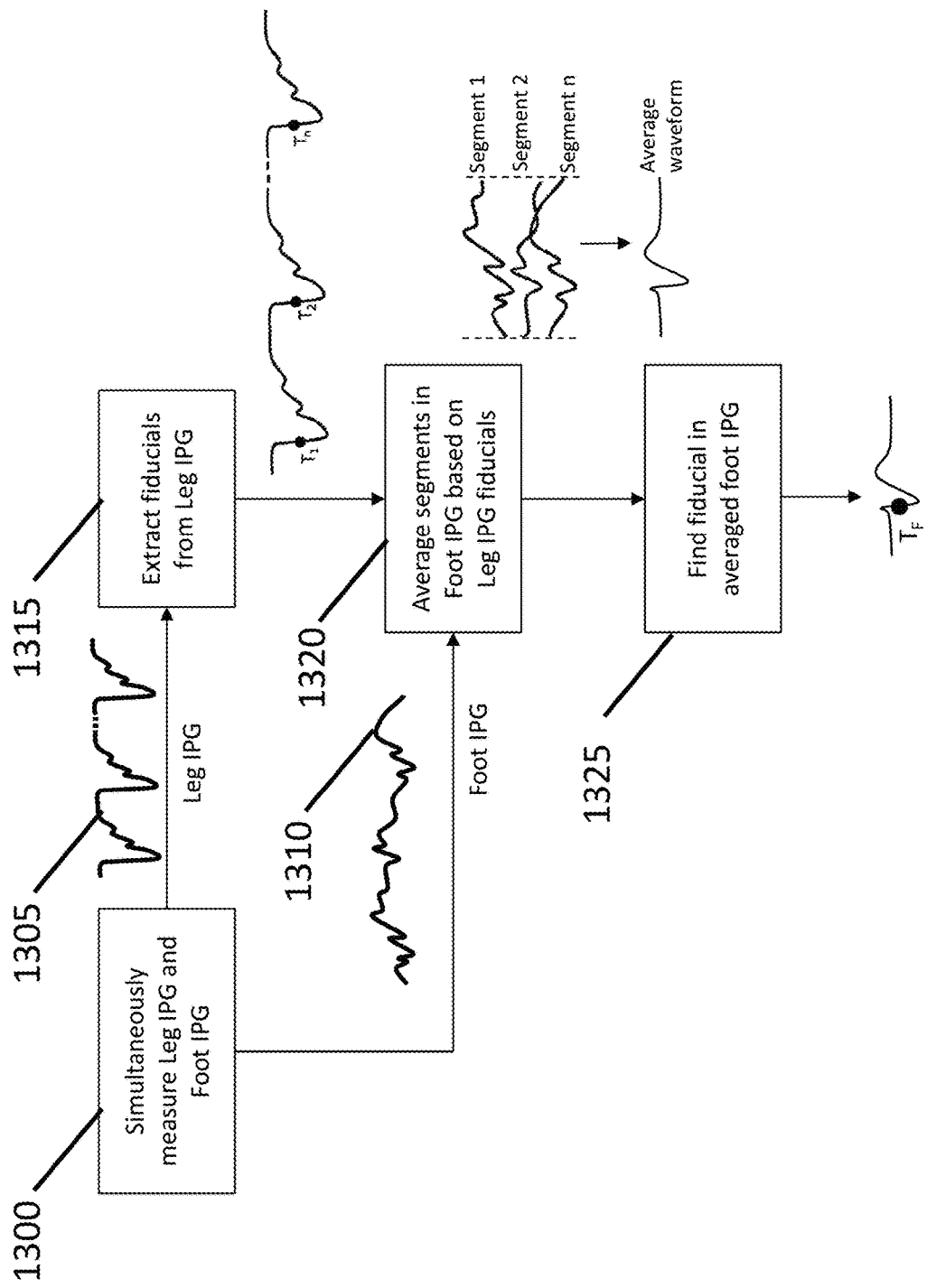
FIG. 13 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure.

In FIG. 13, the Leg IP and the Foot IPG are simultaneously measured (1300), the Leg IPG is low-pass filtered (1305), the foot IPG is low-pass filtered (1310), and segments starting from the timings are extracted (1315) from the Leg IPG (reference timings). The segments of the Foot IPG extracted based on the Leg IPG timings are ensemble-averaged (1320) to produce a higher SNR Foot IPG pulse. From this ensemble-averaged signal, the start of the pulse is extracted using the same intersecting tangent approach as described earlier. This approach enables the extraction of accurate timings in the Foot IPG even if the impedance signal is dominated by noise. These timings are used together with timings extracted from the BCG for the purpose of computing the PTT and (PWV). Timings derived from ensemble-averaged waveforms and individual waveforms are both extracted, for the purpose of comparison, averaging and error-detection.

Specific timings that can be extracted from the IPG pulses (from either leg or foot) are related (but not limited) to the peak of the pulse, to the minimum preceding the peak, or to the maximum second derivative (maximum rate of acceleration) preceding the point of maximum derivative. An IPG pulse and the extraction of a fiducial (1325) in the IPG can also be performed by several other signal processing methods, including (but not limited to) template matching, cross-correlation, wavelet-decomposition, or short window Fourier transform.

In certain embodiments, a dual-Foot IPG is measured, allowing the detection of blood pressure pulses in both feet. Such information is used for diagnostic of peripheral arterial diseases (PAD) by comparing the relative PATs in both feet to look for asymmetries. It is be used to increase the robustness of the measurement by allowing one foot to have poor contact with electrodes (or no contact at all). SNR measurements are used to assess the quality of the signal in each foot, and to select the best signal for downstream analysis. Timings extracted from each foot are compared and set to flag potentially inaccurate PWV measurements due to arterial peripheral disease, in the event these timings are different by more than a defined threshold. Alternatively, timings from both feet are pooled to increase the overall SNR if their difference is below a defined threshold.

In certain embodiments, a PWV is measured, where the IPG is augmented by the addition of BCG sensing into the weighing scale to determine characteristic fiducials between the BCG and Leg IPG trigger, or the BCG and Foot IPG. The BCG sensors are comprised typically of the same strain gage set used to determine the bodyweight of the user. The load cells are typically wired into a bridge configuration to create a sensitive resistance change with small displacements due to the ejection of the blood into the aorta, where the circulatory or cardiovascular force produce movements within the body on the nominal order of 1-3 Newtons. BCG forces can be greater than or less than the nominal range in cases such as high or low cardiac output.

Figure 14:
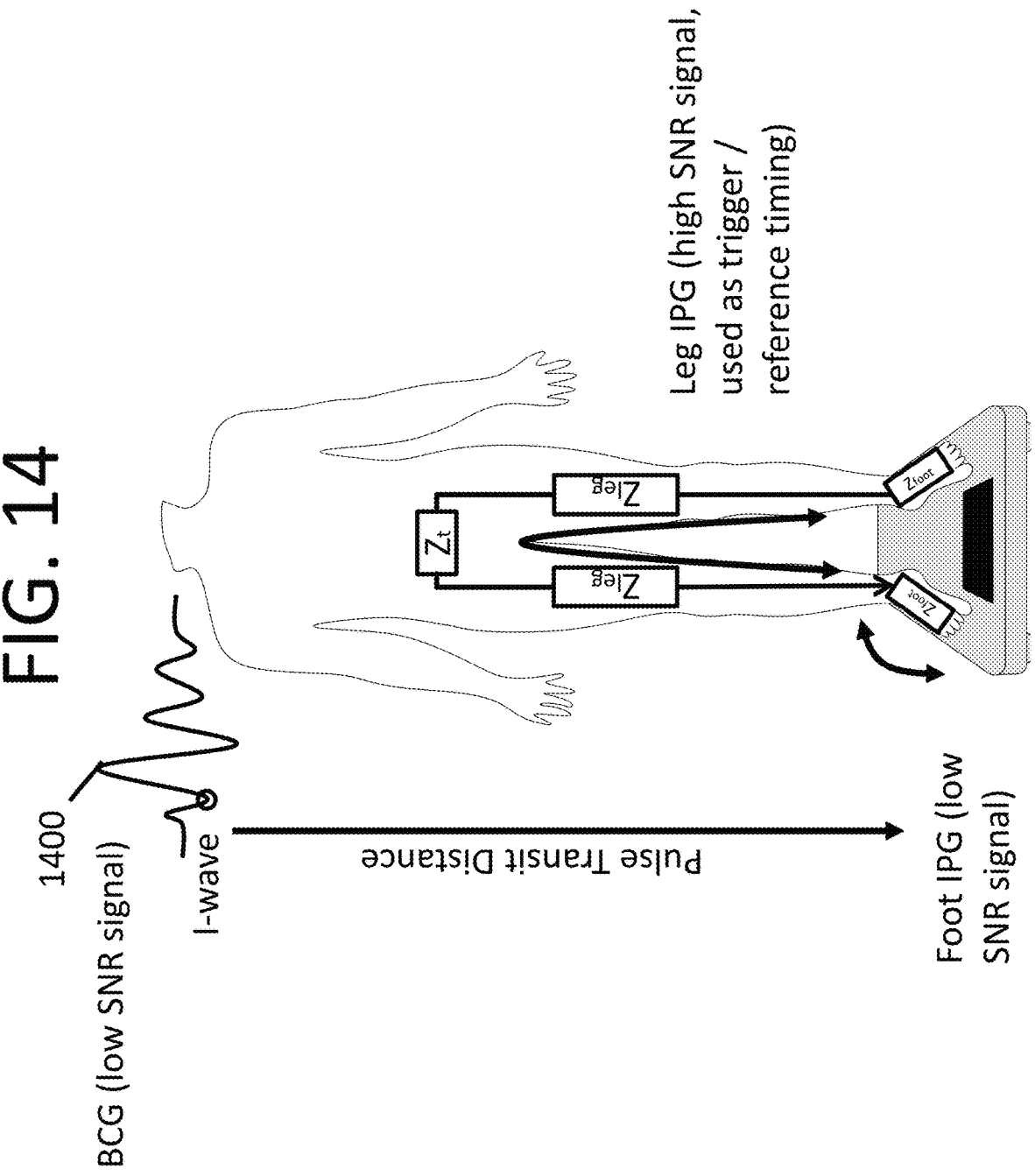
FIG. 14 shows an example configuration for obtaining the pulse transit time (PTT), using the first IPG as the triggering pulse for the Foot IPG and ballistocardiogram (BCG), consistent with various aspects of the present disclosure.

FIG. 14 shows an example configuration to obtain the PTT, using the first IPG as the triggering pulse for the Foot IPG and BCG, consistent with various aspects of the present disclosure. The I-wave of the BCG 1400 as illustrated normally depicts the headward force due to cardiac ejection of blood into the ascending aorta which can be used as a timing fiducial indicative of the pressure pulse initiation of the user's proximal aorta relative to the user's heart. The J-wave is also indicative of timings in the systole phase and also incorporates information related to the strength of cardiac ejection and the ejection duration. The K-Wave also provides systolic and vascular information of the user's aorta. In some embodiments, the characteristic timings of these and other BCG waves are used as fiducials that are related to fiducials of the IPG signals of the present disclosure.

FIG. 15 shows another example of a scale 1500 with interleaved foot electrodes 1505 to inject and sense current from one foot to another foot, and within one foot, consistent with various aspects of the present disclosure. FIG. 16A-16C shows various examples of a scale 1600 with interleaved foot electrodes 1605 to inject and sense current from one foot to another foot, and measure Foot IPG signals in both feet, consistent with various aspects of the present disclosure. FIGS. 17A-D shows an example breakdown of a scale 1700 with interleaved foot electrodes 1705 to inject and sense current from one foot to another foot, and within one foot, consistent with various aspects of the present disclosure.

Figure 18:
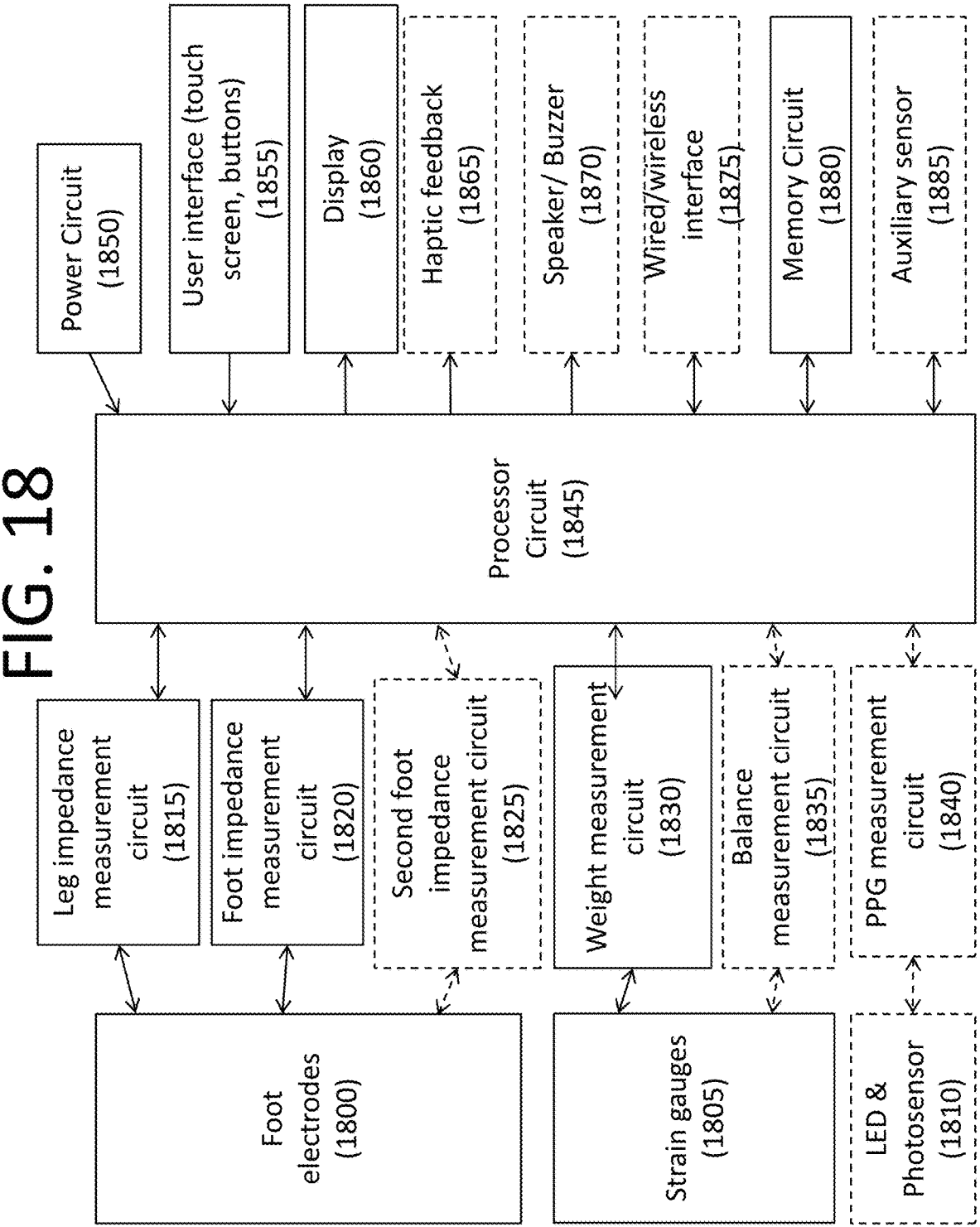
FIG. 18 shows an example block diagram of circuit-based building blocks, consistent with various aspects of the present disclosure.

FIG. 18 shows an example block diagram of circuit-based building blocks, consistent with various aspects of the present disclosure. The various circuit-based building blocks shown in FIG. 18, in accordance with some embodiments, are implemented in connection with the various aspects discussed herein. In the example shown, the block diagram includes foot electrodes 1800 that collects the IPG signals. Further, the block diagram includes strain gauges 1805, and an LED/photosensor 1810. The foot electrodes 1800 is configured with a leg impedance measurement circuit 1815, a foot impedance measurement circuit 1820, and an optional second foot impedance measurement circuit 1825. The leg impedance measurement circuit 1815, the foot impedance measurement circuit 1820, and the optional second foot impedance measurement circuit 1825 report the measurements collected to a processor circuit 1845.

The processor circuit 1845 also collects data from a weight measurement circuit 1830 and an optional balance measurement circuit 1835 that are configured with the strain gauges 1805. For example, in accordance with various embodiments, the strain gauges can obtain analog signals in response to movement of the user. The processor circuit and/or the balance measurement circuit can detect movement based on the analog signals and determine physiological parameters in one or more directions using the movement and the analog signals. Further, an optional photoplethysmogram (PPG) measurement circuit 1840, which collects data from the LED/photosensor 1810, provides data to the processor circuit 1845.

The processor circuit 1845 is powered via a power circuit 1850. Further, the processor circuit 1845 also collects user input data from a user interface 1855 that can include a touch screen and/or buttons. The data collected/measured by the processor circuit 1845 is shown to the user via a display 1860. Additionally, the data collected/measured by the processor circuit 1845 is stored in a memory circuit 1880. Further, the processor circuit 1845 can optionally control a haptic feedback circuit 1865, a speaker or buzzer 1870, a wired/wireless interface 1875, and an auxiliary sensor 1885.

Figure 19:
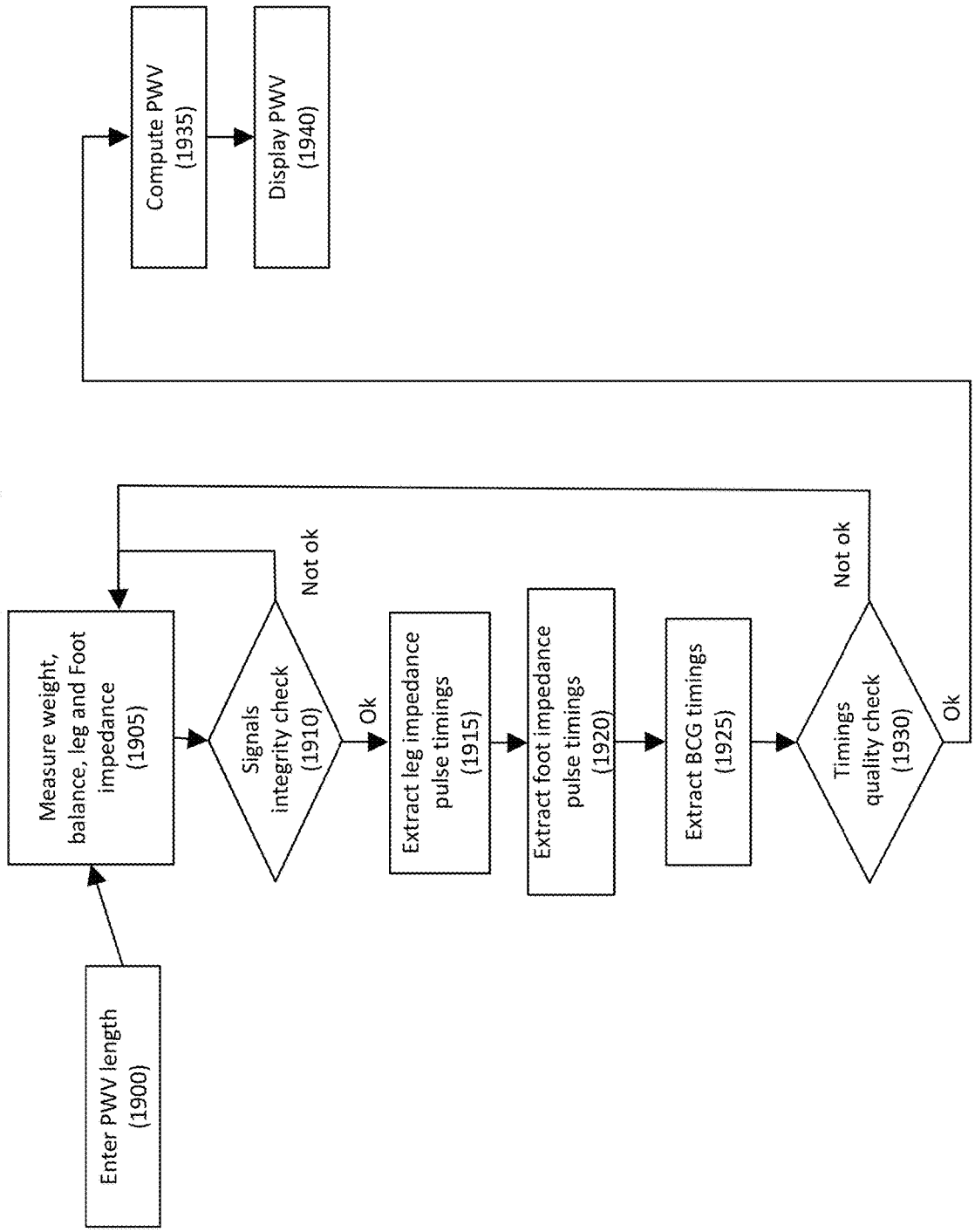
FIG. 19 shows an example flow diagram, consistent with various aspects of the present disclosure.

FIG. 19 shows an example flow diagram, consistent with various aspects of the present disclosure. As shown in block 1900, a PWV length is entered. As is shown in block 1905, a user's weight, balance, leg, and foot impedance are measured (as is consistent with various aspects of the present disclosure). As is shown at block 1910, the integrity of signals is checked (e.g., signal to noise ratio). If the signal integrity check is not met, the user's weight, balance, leg, and foot impedance are measured again (block 1905). If the signals integrity check is met, the leg impedance pulse timings are extracted (as is shown at block 1915). As is shown at block 1920, foot impedance and pulse timings are extracted, and as is shown at block 1925, BCG timings are extracted. As is shown at block 1930, a timings quality check is performed. If the timings quality check is not validated, the user's weight, balance, leg and foot impedance are again measured (block 1905). If the timings quality check is validated, the PWV is calculated (as is shown at block 1935). Finally, as is shown at block 1940, the PWV is displayed to the user.

Figure 20:
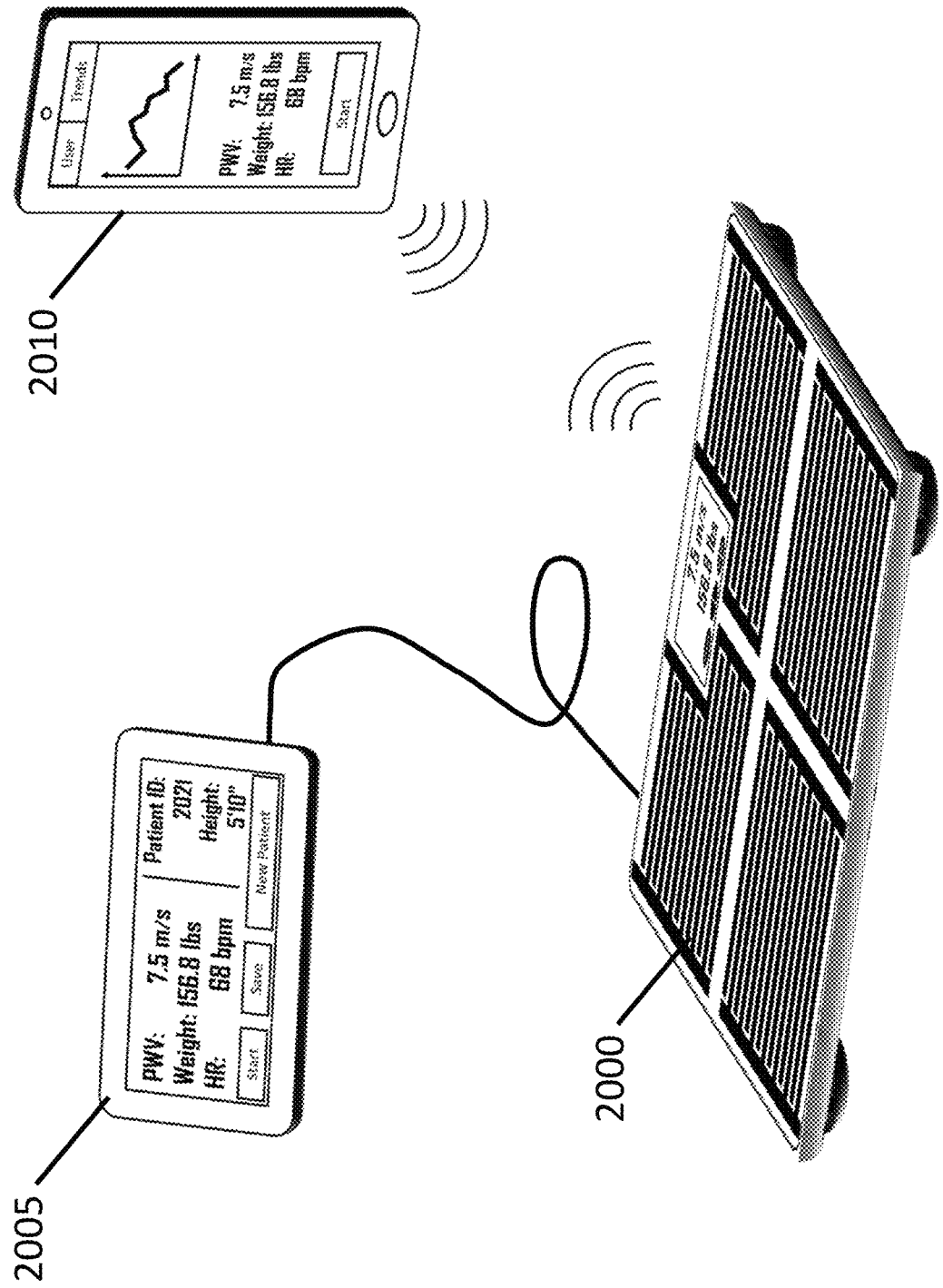
FIG. 20 shows an example scale communicatively coupled to a wireless device, consistent with various aspects of the present disclosure.

FIG. 20 shows an example scale 2000 communicatively coupled to a wireless device, consistent with various aspects of the present disclosure. As described herein, a display 2005 displays the various aspects measured by the scale 2000. The scale can also wirelessly broadcast the measurements to a wireless device 2010.

Figure 21B:
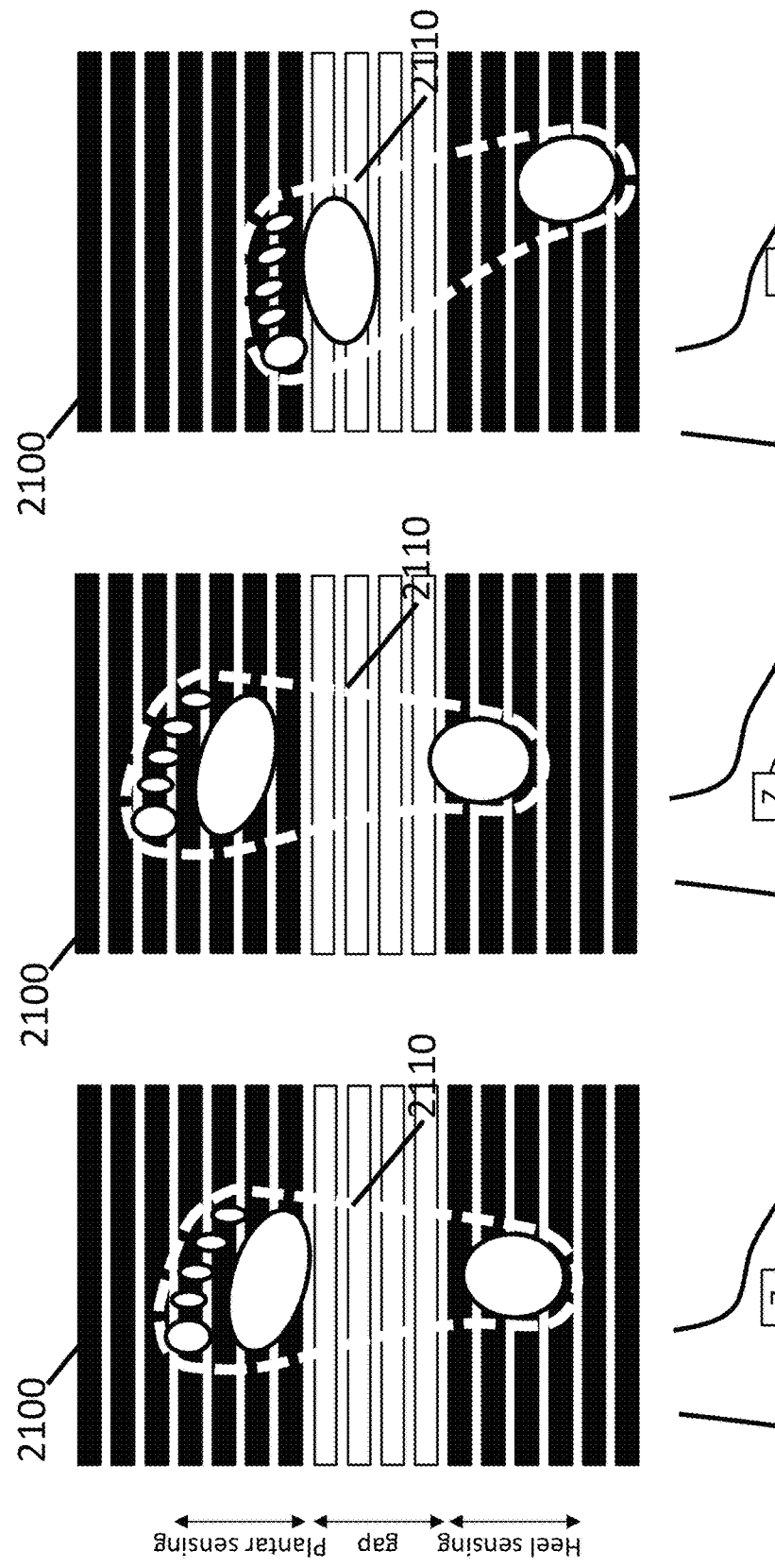

FIGS. 21A-C show example impedance as measured through different parts of the foot based on the foot position, consistent with various aspects of the present disclosure. For instance, example impedance measurement configurations are implemented using a dynamic electrode configuration for measurement of foot impedance and related timings, consistent with various aspects of the present disclosure. Dynamic electrode configuration are implemented using independently-configurable electrodes to optimize the impedance measurement. As shown in FIG. 21A, interleaved electrodes 2100 are connected to an impedance processor circuit 2105 to determine foot length, foot position, and/or foot impedance. As is shown in FIG. 21B, an impedance measurement is determined regardless of foot position 2110 based on measurement of the placement of the foot across the electrodes 2100. This is based in part in the electrodes 2100 that are engaged (blackened) and in contact with the foot (based on the foot position 2110), which is shown in FIG. 21C.

More specifically regarding FIG. 21A, the configuration includes connection/de-connection of the individual electrodes 2100 to the impedance processor circuit 2105, their configuration as current-carrying electrodes (injection or return), sense electrodes (positive or negative), or both. The configuration can either be preset based on user information, or updated at each measurement (dynamic reconfiguration) to optimize a given parameter (impedance SNR, measurement location). The system, for instance, algorithmically determines which electrodes under the foot to use in order to obtain the highest SNR in the pulse impedance signal. Such optimization algorithm includes iteratively switching configurations and measuring the resulting impedance, then selecting the best-suited configuration. Alternatively, the system first, through a sequential impedance measurement between each individual electrode 2100 and another electrode in contact with the body (such as an electrode in electrode pair on the other foot), determines which electrodes are in contact with the foot. By determining the two most apart electrodes, the foot size is determined. Heel location is determined in this manner, as can other characteristics such as foot arch type. These parameters, in some embodiments, are used to determine programmatically (in an automated manner by CPU/logic circuitry) which electrodes are selected for current injection and return (as well as sensing if a Kelvin connection issued) in order to obtain the best foot IPG.

In various embodiments involving the dynamically reconfigurable electrode array 2100/2105, an electrode array set is selected to measure the same portion (or segment) of the foot, irrespective of the foot location on the array. FIG. 21B illustrates the case of several foot positions on a static array (a fixed set of electrodes are used for measurement at the heel and plantar/toe areas, with a fixed gap of an inactive electrode or insulating material between them). Depending on the position of the foot, the active electrodes are contacting the foot at different locations, thereby sensing a different volume (or segment) of the foot. If the IPG is used by itself (e.g., for heart measurement), such discrepancies may be non-consequential. However, if timings derived from the IPG are referred to other timings (e.g., R-wave from the ECG, or specific timing in the BCG), such as for the calculation of a PTT or PWV, the small shifts in IPG timings due to the sensing of slightly different volumes in the foot (e.g., if the foot is not always placed at the same position on the electrodes) introduces an error in the calculation of the interval. Such location variations can occur in the day-to-day use of the scale. With respect to FIG. 21B for instance, the timing of the peak of the IPG from the foot placement on the right (sensing the toe/plantar region) is later than from the foot placement on the left, which senses more of the heel volume (the pulse reaches first the heel, then the plantar region). Factors influencing the magnitude of these discrepancies include foot shape (flat or not) and foot length.

Various embodiments address challenges relating to foot placement. FIG. 21C shows an example embodiment involving dynamic reconfiguration of the electrodes to reduce such foot placement-induced variations. As an example, by sensing the location of the heel first (as described above), only a subset of electrodes under the heel are activated, and another subset of electrodes separated by a fixed distance (2100). The other electrodes (e.g., unused electrodes) are left disconnected. The sensed volume is therefore the same, producing consistent timings. The electrode configuration leading to the most consistent results are informed by the foot impedance, foot length, the type of arch (all of which can be measured by the electrode array as shown above), but also by the user ID (foot information can be stored for each user, then looked up based on automatic user recognition or manual selection (e.g., in a look-up-table stored for each user in a memory circuit accessible by the CPU circuit in the scale)).

Accordingly, in certain embodiments, the impedance-measurement apparatus measures impedance using a plurality of electrodes contacting one foot and with at least one other electrode (typically many) at a location distal from the foot. The plurality of electrodes (contacting the one foot) is arranged on the platform and in a pattern configured to inject current signals and sense signals in response thereto, for the same segment of the foot so that the timing of the pulse-based measurements does not vary simply because the user placed the one foot at a slightly different position on the platform or scale. Thus, in FIG. 21A, the foot-to-electrode locations for the heel are different locations than that shown in FIGS. 21B and 21C. As this different foot placement occurs from day to day for the user, the timing and related impedance measurements are the same (internal) segment of the foot. By having the computer processor circuit inject current and sense responsive signals to first locate the foot on the electrodes (e.g., sensing where positions of the foot's heel plantar regions and/or toes), the pattern of foot-to-electrode locations permits the foot to move laterally, horizontally and both laterally and horizontally via the different electrode locations, while collecting impedance measurements relative to the same segment of the foot.

The BCG/IPG system, in some embodiments, is used to determine the PTT of the user, by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. In certain embodiments, the BCG/IPG system is used to determine the PWV of the user, by identification of the characteristic length representing the length of the user's arteries, and by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. The system of the present disclosure and alternate embodiments is suitable for determining the arterial stiffness (or arterial compliance) and/or cardiovascular risk of the user regardless of the position of the user's feet within the bounds of the interleaved electrodes. In certain embodiments, the weighing scale system incorporates the use of strain gage load cells and six or eight electrodes to measure a plurality of signals including: bodyweight, BCG, body mass index, fat percentage, muscle mass percentage, and body water percentage, heart rate, heart rate variability, PTT, and PWV measured simultaneously or synchronously when the user stands on the scale to provide a comprehensive analysis of the health and wellness of the user.

In other certain embodiments, the PTT and PWV are computed using timings from the Leg IPG or Foot IPG for arrival times, and using timings from a sensor located on the upper body (as opposed to the scale measuring the BCG) to detect the start of the pulse. Such sensor may include an impedance sensor for impedance cardiography, a hand-to-hand impedance sensor, a photoplethysmogram on the chest, neck, head, arms or hands, or an accelerometer on the chest (seismocardiograph) or head.

Communication of the biometric information is another aspect of the present disclosure. The biometric results from the user are stored in the memory on the scale and displayed to the user via a display on the scale, audible communication from the scale, and/or the data is communicated to an external device such as a computer, smart phone, or tablet computing device. The communication occurs directly to the external device with a wired connection, or is sent to the external device through wireless communication protocols such as Bluetooth or WiFi. Computations such as signal analyses described therein may be carried out locally on the scale, in a smartphone or computer, or in a remote processor (cloud computing).

Other aspects of the present disclosure are directed toward apparatuses or methods that include the use of at least two electrodes that contact feet of a user. Further, circuitry is provided to determine a pulse arrival time at the foot based on the recording of two or more impedance signals from the set of electrodes. Additionally, a second set of circuitry is provided to extract a first pulse arrival time from a first impedance signal and use the first pulse arrival time as a timing reference to extract and process a second pulse arrival time in a second impedance signal.

As illustrated herein, various circuit-based building blocks and/or modules may be implemented to carry out one or more of the operations and activities described herein shown in the block-diagram-type figures. In such contexts, these building blocks and/or modules represent circuits that carry out one or more of these or related operations/activities. For example, in certain of the embodiments discussed above (such as the pulse circuitry modularized as shown in FIGS. 11A-B), one or more blocks/modules are discrete logic circuits or programmable logic circuits configured and arranged for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible form, a memory (circuit). As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Based upon the above discussion and illustrations, those skilled in the art will readily recognize that various modifications and changes may be made to the present disclosure without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Such modifications do not depart from the true spirit and scope of the present disclosure, including that set forth in the following claims.

What is claimed is:

1. An apparatus comprising:
a platform region configured and arranged with an area for a user to stand;
a plurality of force sensors, including sensor circuitry configured and arranged within the platform region to provide a plurality of analog signals responsive to the user standing on the platform region and to engage the user with the plurality of force sensors while the user stands on the platform region, wherein the analog signals include an indication of force differences against the platform due to postural sway or movement of the user; and
processor circuitry configured and arranged to determine cardiac physiological parameters of the user corresponding to cardiac movements including movements between heart beats of the user's heart, by:
processing the analog signals from the sensor circuitry, the analog signals being indicative of the cardiac physiological parameters and of postural sway or movement of the user while the user stands on the platform region;
mitigating at least some effect on the analog signals attributable to the postural sway or movement of the user while the user stands on the platform region; and
generating data indicative of the cardiac physiological parameters based on the analog signals indicative of the cardiac physiological parameters and the postural sway or the movement and the mitigating of at least some of the effect on the analog signals attributable to postural sway of the user while the user stands on the platform region, wherein the data generated includes at least one of the cardiac physiological parameters in a lateral direction or a dorsoventral direction, wherein the analog signals provide indications of tilt and lean movement of the user and wherein generating the data includes using the analog signals to extract a cardiac physiological signal indicative of a first cardiac physiological parameter in the lateral direction and a second cardiac physiological signal indicative of the cardiac physiological parameter in the dorsoventral direction.

2. The apparatus of claim 1, wherein the tilt and lean movement is relative to a nominal-still position of the user.

3. The apparatus of claim 1, wherein the postural sway or movement of the user includes balance movement of the user corresponding to the user shifting weight while standing on the platform region.

4. The apparatus of claim 1, wherein generating the data includes extracting at least two cardiac physiological signals from the analog signals, the cardiac physiological signals selected from the group consisting of: a lateral ballistocardiogram (BCG), a dorsoventral BCG signal, a longitudinal BCG signal, and a combination thereof.

5. The apparatus of claim 1, wherein a cardiac physiological parameter of the user is a three-dimensional cardiac physiological parameter determined using cardiac physiological signals indicative of the cardiac physiological parameter in three directions.

6. The apparatus of claim 1, wherein a cardiac physiological parameter of the user is a two-dimensional cardiac physiological parameter determined using cardiac physiological signals indicative of the cardiac physiological parameter in two directions, wherein at least one of the cardiac physiological parameters is determined using the analog signals indicative of the postural sway or the movement.

7. The apparatus of claim 1, further including:
a support structure including the platform region and said sensor circuitry,
wherein the sensor circuitry further includes electrodes configured and arranged to contact the user, and the sensor circuitry is further configured and arranged to obtain a plurality of impedance signals via the electrodes and to determine additional cardiac physiological parameters of the user using the plurality of impedance signals.

8. The apparatus of claim 1, wherein the processor circuitry is further configured and arranged to detect the postural sway or the movement of the user, including detecting lateral movement and dorsoventral movement, by comparing analog signals from the force sensors and the cardiac physiological parameters determined includes a cardiac physiological parameter determined using a lateral cardiac physiological signal indicative of the cardiac physiological parameter in the lateral direction and a cardiac physiological signal indicative of the cardiac physiological parameter in the dorsoventral direction.

9. The apparatus of claim 8, wherein the processor circuitry is further configured and arranged to determine the cardiac physiological signal indicative of the cardiac physiological parameter in the lateral direction by comparing analog signals via the sensor circuitry, or from a first subset of the plurality of force sensors, associated with a first foot of the user standing on the platform region to analog signals also via the sensor circuitry, or from a second subset of the plurality of force sensors, associated with a second foot of the user.

10. The apparatus of claim 8, wherein the processor circuitry is further configured and arranged to determine the cardiac physiological signal indicative of the cardiac physiological parameter in the dorsoventral direction by comparing analog signals via the sensor circuitry associated with a first portion of feet of the user standing on the platform region to analog signals also via the sensor circuitry associated with a second portion of the feet of the user.

11. An apparatus comprising:
a platform region configured and arranged with an area for a user to stand;
a support structure including the platform region and including a plurality of force sensors having sensor circuitry configured and arranged to provide a plurality of analog signals responsive to the user standing on the platform region and while the user is standing on the platform region, the platform region being configured and arranged to engage the user with the plurality of force sensors while the user stands on the platform region; and
processor circuitry configured and arranged to determine cardiac physiological parameters of the user corresponding to cardiac movements including movements between heart beats of the user's heart, by:
processing the analog signals from the sensor circuitry, the analog signals being indicative of postural sway or movement of the user while the user stands on the platform region;
mitigating at least some effect on the analog signals attributable to the postural sway or movement of the user while the user stands on the platform region, the postural sway or movement including at least one of tilt and lean movement of the user relative to a nominal-still position of the user; and generating data indicative of the cardiac physiological parameters based on said processing of the analog signals indicative of the postural sway or the movement from the sensor circuitry and the mitigating of at least some of the effect on the analog signals attributable to postural sway or movement of the user while the user stands on the platform region, wherein the data generated includes the cardiac physiological parameters corresponding to one of or two directions that are orthogonal to one another and corresponding to the postural sway or movement of the user in respectively orthogonal directions.

12. The apparatus of claim 11, further including a secondary sensor configured and arranged to measure cardiac physiological parameters of the user, wherein the processor circuitry is further configured and arrange to de-noise the cardiac physiological parameters using the cardiac physiological parameters measured by the secondary sensor, wherein the analog signals are indicative of differential electrical resistance, as indicated by the sensor circuitry, due to the postural sway or movement of the user, and the processing circuitry is configured and arranged to generate the data indicative of the cardiac physiological parameters based on the analog signal.

13. The apparatus of claim 11, wherein the processor circuitry configured and arranged to mitigate at least some effect on the analog signals attributable to postural sway or movement of the user and generate the data indicative of the cardiac physiological parameters, includes removing a baseline wander from the analog signals to obtain at least one cardiac physiological signal indicative of a cardiac physiological parameter.

14. The apparatus of claim 11, further including the plurality of force sensors, wherein the plurality of force sensors include four force sensors configured and arranged in the corners of the platform region and wherein the plurality of force sensors are configured and arranged to detect differential forces between sides of the apparatus on an order of 0.05 Newtons applied to a side of the apparatus.

15. The apparatus of claim 11, wherein the plurality of force sensors are configured and arranged at a center of the platform region.

16. The apparatus of claim 1, wherein generating the data includes extracting a cardiac physiological signal indicative of the cardiac physiological parameter in the lateral direction using the analog signals indicative of the postural sway or movement.

17. The apparatus of claim 1, wherein generating the data includes extracting a cardiac physiological signal indicative of the cardiac physiological parameter in the dorsoventral direction using the analog signals indicative of the postural sway or movement.

* * * * *